United States Patent
Law et al.

(10) Patent No.: US 10,813,904 B2
(45) Date of Patent: Oct. 27, 2020

(54) SMALL MOLECULE ANTICANCER AGENTS

(71) Applicant: University of Florida Research Foundation, Incorporated, Gainesville, FL (US)

(72) Inventors: Brian Keith Law, Gainesville, FL (US); Ronald K. Castellano, Gainesville, FL (US); Renan B. Ferreira, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/487,304

(22) PCT Filed: Feb. 21, 2018

(86) PCT No.: PCT/US2018/018979
§ 371 (c)(1),
(2) Date: Aug. 20, 2019

(87) PCT Pub. No.: WO2018/156600
PCT Pub. Date: Aug. 30, 2018

(65) Prior Publication Data
US 2020/0054592 A1    Feb. 20, 2020

Related U.S. Application Data

(60) Provisional application No. 62/461,734, filed on Feb. 21, 2017.

(51) Int. Cl.
| | | |
|---|---|---|
| *A61K 31/22* | (2006.01) | |
| *A61K 31/517* | (2006.01) | |
| *C07C 323/64* | (2006.01) | |
| *A61K 39/395* | (2006.01) | |

(52) U.S. Cl.
CPC ............ *A61K 31/22* (2013.01); *A61K 31/517* (2013.01); *A61K 39/3955* (2013.01); *C07C 323/64* (2013.01)

(58) Field of Classification Search
CPC .. A61K 31/22; A61K 31/517; A61K 39/3955; C07C 323/64
USPC .......................................................... 514/518
See application file for complete search history.

(56) References Cited

U.S. PATENT DOCUMENTS 7,674,861 B1   3/2010  York et al.

FOREIGN PATENT DOCUMENTS

WO    WO 2016/025747 A1    2/2016

OTHER PUBLICATIONS

Fraguas et al., Developmental Biology, 2011, 354, 87-101 (Year: 2011).*
International Search Report and Written Opinion dated May 2, 2018, in connection with PCT/US2018/018979.
Pubmed Compound Summary for CID 361202, "UALYKJIOBAAHMN-UHFFFAOYSA-N", U.S. National Library of Medicine. Mar. 26, 2005; https://pubchem.ncbi.nlm.nih.gov/compound/361202. pp. 1-11.
Pubmed Compound Summary for CID 90661289, "VTAGTCCODJQQNHUHFFFAOYSA-M", U.S. National Library of Medicine. Mar. 11, 2015; https://pubchem.ncbi.nlm.nih.gov/compound/90661289. pp. 1-19.
Pubmed Compound Summary for CID 90673305, "GRWLRHBLOQCHRSUHFFFAOYSA-M", U.S. National Library of Medicine. Mar. 11, 2015; https://pubchem.ncbi.nlm.nih.gov/compound/90673305. pp. 1-11.

* cited by examiner

*Primary Examiner* — Yevgeny Valenrod
(74) *Attorney, Agent, or Firm* — Wolf, Greenfield & Sacks, P.C.

(57) ABSTRACT

The invention relates to methods of treating cell proliferative disorders. The invention further relates to pharmaceutical compositions for treating cell proliferative disorders, especially cancer.

20 Claims, 34 Drawing Sheets

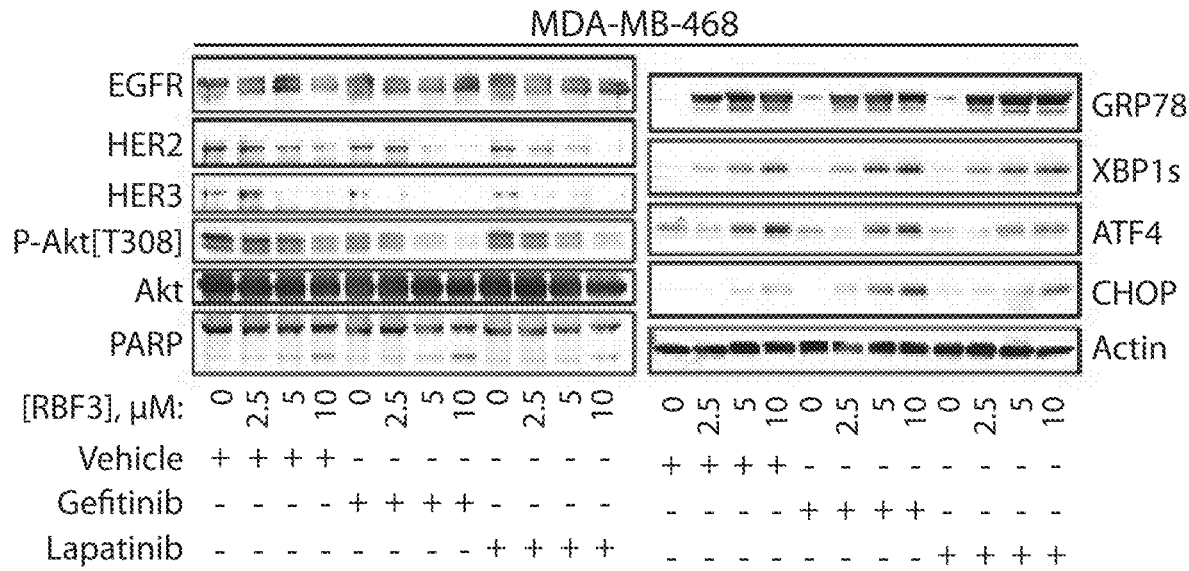
Fig. 4A
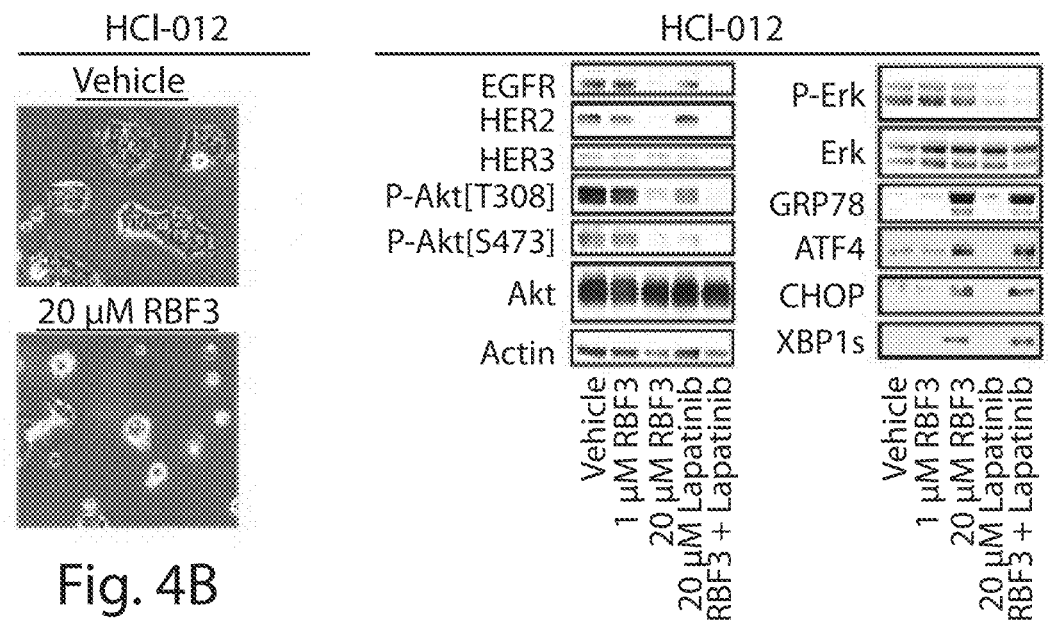
Fig. 4B
Fig. 4C

A. Bn-DDA:

SMALL MOLECULE ANTICANCER AGENTS

CROSS-REFERENCE TO RELATED APPLICATIONS

This Application is a national stage filing under 35 U.S.C. 371 of International Patent Application Serial No. PCT/US2018/018979, filed Feb. 21, 2018, which claims priority to U.S. Provisional Application No. 62/461,734, filed Feb. 21, 2017, which applications are incorporated herein by reference in their entirety.

STATEMENT OF GOVERNMENT SUPPORT

This invention was made with government support under Grant Nos. W81XWH-15-1-0199 and W81XWH-15-1-0200 awarded by the US Army Medical Research Acquisition (USAMRAA). The government has certain rights in the invention. This invention was funded in whole or in part by Bankhead-Coley Cancer Research Program Technology Transfer Feasibility Grant 4BF02.

BACKGROUND OF THE INVENTION

The Epidermal Growth Factor Receptor (EGFR) family members EGFR, Human Epidermal growth factor Receptor-2 (HER2), and Human Epidermal growth factor Receptor-3 (HER3) are well established as proto-oncogenes that play key roles in the initiation and progression of human cancers [Arslan, M. A., Kutuk, O., and Basaga, H. (2006) Protein kinases as drug targets in cancer Curr Cancer Drug Targets 6, 623-634; Yan, M., Parker, B. A., Schwab, R., and Kurzrock, R. (2014) HER2 aberrations in cancer: Implications for therapy Cancer Treat Rev 40, 770-780; Foley, J., Nickerson, N. K., Nam, S., Allen, K. T., Gilmore, J. L., Nephew, K. P., and Riese, D. J., 2nd. (2010) EGFR signaling in breast cancer: bad to the bone Semin Cell Dev Biol 21, 951-960]. EGFR is frequently mutationally activated in lung cancer and is the target of the FDA-approved drugs Cetuximab, Panitumumab, and Erlotinib. Although EGFR is rarely mutated in breast cancers, the wild type protein is frequently overexpressed in breast tumors, and EGFR has been suggested to be a therapeutic target in triple-negative (Estrogen Receptor-, Progesterone Receptor-, and HER2-negative) breast cancers [Park, H. S., Jang, M. H., Kim, E. J., Kim, H. J., Lee, H. J., Kim, Y. J., Kim, J. H., Kang, E., Kim, S. W., Kim, I. A., and Park, S. Y. (2014) High EGFR gene copy number predicts poor outcome in triple-negative breast cancer Mod Pathol].

HER2 is a transmembrane tyrosine kinase overexpressed in approximately 20-25% of human breast tumors [Gori S, Montemurro F, Spazzapan S, Metro G, Foglietta J, et al. (2012) Retreatment with trastuzumab-based therapy after disease progression following lapatinib in HER2-positive metastatic breast cancer. Ann Oncol 23: 1436-1441], usually as a result of gene amplification. HER2 has no known ligands and signals by forming heterodimers with the ligand-dependent receptor tyrosine kinases and HER2 family members EGFR and HER3. HER2 drives mammary tumorigenesis by activating several pathways that promote cell proliferation and survival including the PI3K/Akt/mTORC1 and Ras/Raf/MEK/Erk cascades.

Breast tumors are screened for expression of HER2 and patients with HER2-positive tumors are treated with chemotherapy combined with either the HER2-specific monoclonal antibody Trastuzumab, Trastuzumab+Pertuzumab, the HER2/EGFR tyrosine kinase activity inhibitor Lapatinib, or Trastuzumab+Lapatinib [Baselga J, Tripathy D, Mendelsohn J, Baughman S, Benz C C, et al. (1996) Phase II study of weekly intravenous recombinant humanized anti-p185HER2 monoclonal antibody in patients with HER2/neu-overexpressing metastatic breast cancer. J Clin Oncol 14:737-744; Vogel C L, Cobleigh M A, Tripathy D, Gutheil J C, Harris L N, et al. (2002) Efficacy and safety of trastuzumab as a single agent in first-line treatment of HER2-overexpressing metastatic breast cancer. J Clin Oncol 20: 719-726]. While these agents are effective in treating HER2-positive cancers, tumor resistance is a common problem. In fact, primary resistance to Trastuzumab as a monotherapy against metastatic breast cancer has been observed in 66-88% of patients [Cobleigh M A, Vogel C L, Tripathy D, Robert N J, Scholl S, et al. (1999) Multinational study of the efficacy and safety of humanized anti-HER2 monoclonal antibody in women who have HER2-overexpressing metastatic breast cancer that has progressed after chemotherapy for metastatic disease. J Clin Oncol 17: 2639-2648; Slamon D J, Leyland-Jones B, Shak S, Fuchs H, Paton V, et al. (2001) Use of chemotherapy plus a monoclonal antibody against HER2 for metastatic breast cancer that overexpresses HER2. N Engl J Med 344: 783-792; Piccart-Gebhart M J, Procter M, Leyland-Jones B, Goldhirsch A, Untch M, et al. (2005) Trastuzumab after adjuvant chemotherapy in HER2-positive breast cancer. N Engl J Med 353: 1659-1672]. While combining Trastuzumab with the taxanes Paclitaxel or Docetaxel improves patient outcomes [1], 15% of patients fail this therapy as well [Gayle S S, Castellino R C, Buss M C, Nahta R (2013) MEK inhibition increases lapatinib sensitivity via modulation of FOXM1. Curr Med Chem 20: 2486-2499]. Likewise, resistance to Lapatinib is a significant problem and investigating the mechanisms responsible for resistance to Trastuzumab and Lapatinib are areas of intense research [Wetterskog D, Shiu K K, Chong I, Meijer T, Mackay A, et al. (2014) Identification of novel determinants of resistance to lapatinib in ERBB2-amplified cancers. Oncogene 33: 966-976; Fabi A, Merola R, Ferretti G, Di Benedetto A, Antoniani B, et al. (2013) Epidermal growth factor receptor gene copy number may predict lapatinib sensitivity in HER2-positive metastatic breast cancer. Expert Opin Pharmacother 14: 699-706; Blumenthal G M, Scher N S, Cortazar P, Chattopadhyay S, Tang S, et al. (2013) First FDA approval of dual anti-HER2 regimen: pertuzumab in combination with trastuzumab and docetaxel for HER2-positive metastatic breast cancer. Clin Cancer Res 19: 4911-4916]. The HER2-specific monoclonal antibody Pertuzumab blocks HER2 dimerization with EGFR or HER3 and is FDA-approved for use in combination with Trastuzumab and Docetaxel. Unfortunately, >30% of patients experience cardiotoxicity [Ogiso H, Ishitani R, Nureki O, Fukai S, Yamanaka M, et al. (2002) Crystal structure of the complex of human epidermal growth factor and receptor extracellular domains. Cell 110: 775-787] or other serious side effects including anaphylaxis/hypersensitivity reactions with this combination therapy. Thus, although targeted therapeutics are available for the treatment of HER2-positive breast cancer, many patients still die from metastatic disease due to primary or acquired resistance, and these therapies are still associated with adverse reactions.

HER2 overexpression in breast cancer is associated with poor prognosis, but the advent of HER2-targeted antibodies such as Trastuzumab (Herceptin) and Pertuzumab, and ER2/EGFR tyrosine kinase inhibitors such as Lapatinib, have revolutionized the treatment of HER2-positive breast cancer. Unfortunately, 66-88% of HER2-positive tumors exhibit primary resistance to Trastuzumab as a monotherapy

[Baselga, J., Tripathy, D., Mendelsohn, J., Baughman, S., Benz, C. C., Dantis, L., Sklarin, N. T., Seidman, A. D., Hudis, C. A., Moore, J., Rosen, P. P., Twaddell, T., Henderson, I. C., and Norton, L. (1996) Phase II study of weekly intravenous recombinant humanized anti-p185HER2 monoclonal antibody in patients with HER2/neu-overexpressing metastatic breast cancer J Clin Oncol 14, 737-744; Vogel, C. L., Cobleigh, M. A., Tripathy, D., Gutheil, J. C., Harris, L. N., Fehrenbacher, L., Slamon, D. J., Murphy, M., Novotny, W. F., Burchmore, M., Shak, S., Stewart, S. J., and Press, M. (2002) Efficacy and safety of trastuzumab as a single agent in first-line treatment of HER2-overexpressing metastatic breast cancer J Clin Oncol 20, 719-726; Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J. (1999) Multinational study of the efficacy and safety of humanized anti-HER2 monoclonal antibody in women who have HER2-overexpressing metastatic breast cancer that has progressed after chemotherapy for metastatic disease J Clin Oncol 17, 2639-2648]. Further, standard Trastuzumab-centered regimens include either a Taxane or an Anthracycline to provide acceptable anti-cancer efficacy, but 15% of patients acquire resistance to these combination therapies as well [Piccart-Gebhart, M. J., Procter, M., Leyland-Jones, B., Goldhirsch, A., Untch, M., Smith, I., Gianni, L., Baselga, J., Bell, R., Jackisch, C., Cameron, D., Dowsett, M., Barrios, C. H., Steger, G., Huang, C. S., Andersson, M., Inbar, M., Lichinitser, M., Lang, I., Nitz, U., Iwata, H., Thomssen, C., Lohrisch, C., Suter, T. M., Ruschoff, J., Suto, T., Greatorex, V., Ward, C., Straehle, C., McFadden, E., Dolci, M. S., and Gelber, R. D. (2005) Trastuzumab after adjuvant chemotherapy in HER2-positive breast cancer N Engl J Med 353, 1659-1672]. These regimens are associated with significant side effects including cardiotoxicity and anaphylaxis [McKeage, K., and Perry, C. M. (2002) Trastuzumab: a review of its use in the treatment of metastatic breast cancer overexpressing HER2 Drugs 62, 209-243]. Clearly, additional therapies are needed to reduce the toxicity of HER2-targeted therapies and to overcome drug resistance.

A large number of resistance mechanisms to Trastuzumab and Lapatinib have been described [Vu, T., and Claret, F. X. (2012) Trastuzumab: updated mechanisms of action and resistance in breast cancer Front Oncol 2, 62; Hutchinson, L. (2010) Targeted therapies: Activated PI3K/AKT confers resistance to trastuzumab but not lapatinib Nat Rev Clin Oncol 7, 424; Wang, Y. C., Morrison, G., Gillihan, R., Guo, J., Ward, R. M., Fu, X., Botero, M. F., Healy, N. A., Hilsenbeck, S. G., Phillips, G. L., Chamness, G. C., Rimawi, M. F., Osborne, C. K., and Schiff, R. (2011) Different mechanisms for resistance to trastuzumab versus lapatinib in HER2-positive breast cancers—role of estrogen receptor and HER2 reactivation Breast Cancer Res 13, R121; Gayle, S. S., Arnold, S. L., O'Regan, R. M., and Nahta, R. (2012) Pharmacologic inhibition of mTOR improves lapatinib sensitivity in HER2-overexpressing breast cancer cells with primary trastuzumab resistance Anticancer Agents Med Chem 12, 151-162]. Many of these mechanisms involve the ability of these three proteins to function in a partially redundant manner. For example, when Trastuzumab inactivates HER2, EGFR and HER3 can still heterodimerize and drive mitogenic and survival signaling [Narayan, M., Wilken, J. A., Harris, L. N., Baron, A. T., Kimbler, K. D., and Maihle, N. J. (2009) Trastuzumab-induced HER reprogramming in "resistant" breast carcinoma cells Cancer Res 69, 2191-2194]. Likewise, Pertuzumab blocks HER2 dimerization with EGFR or HER3, but does not preclude EGFR/HER3 dimerization and signaling. Lapatinib blocks the kinase activity of both HER2 and EGFR. While HER3 has very little intrinsic tyrosine kinase activity [Kol, A., Terwisscha van Scheltinga, A. G., Timmer-Bosscha, H., Lamberts, L. E., Bensch, F., de Vries, E. G., and Schroder, C. P. (2014) HER3, serious partner in crime: therapeutic approaches and potential biomarkers for effect of HER3-targeting Pharmacol Ther 143, 1-11; Gullick, W. J. (1996) The c-erbB3/HER3 receptor in human cancer Cancer Surv 27, 339-349], it can serve as a substrate for c-Met and activate PI3K-dependent signaling in the absence of EGFR and HER2 function [Engelman, J. A., Zejnullahu, K., Mitsudomi, T., Song, Y., Hyland, C., Park, J. O., Lindeman, N., Gale, C. M., Zhao, X., Christensen, J., Kosaka, T., Holmes, A. J., Rogers, A. M., Cappuzzo, F., Mok, T., Lee, C., Johnson, B. E., Cantley, L. C., and Janne, P. A. (2007) MET amplification leads to gefitinib resistance in lung cancer by activating ERBB3 signaling Science 316, 1039-1043; Minuti, G., Cappuzzo, F., Duchnowska, R., Jassem, J., Fabi, A., O'Brien, T., Mendoza, A. D., Landi, L., Biernat, W., Czartoryska-Arlukowicz, B., Jankowski, T., Zuziak, D., Zok, J., Szostakiewicz, B., Foszczynska-Kloda, M., Tempinska-Szalach, A., Rossi, E., and Varella-Garcia, M. (2012) Increased MET and HGF gene copy numbers are associated with trastuzumab failure in HER2-positive metastatic breast cancer Br J Cancer 107, 793-799; Chen, C. T., Kim, H., Liska, D., Gao, S., Christensen, J. G., and Weiser, M. R. (2012) MET activation mediates resistance to lapatinib inhibition of HER2-amplified gastric cancer cells Mol Cancer Ther 11, 660-669]. Therefore, an improved agent for the treatment of HER2-dependent breast cancer would inactivate EGFR, HER2, and HER3 in parallel, be effective in the treatment of cancer as a single agent, and be mechanistically complementary with the HER2-targeted monoclonal antibodies and tyrosine kinase inhibitors.

Examination of the extracellular domains of EGFR, HER2, and HER3 [Garrett T P, McKern N M, Lou M, Elleman T C, Adams T E, et al. (2003) The crystal structure of a truncated ErbB2 ectodomain reveals an active conformation, poised to interact with other ErbB receptors. Mol Cell 11: 495-505; Cho H S, Mason K, Ramyar K X, Stanley A M, Gabelli S B, et al. (2003) Structure of the extracellular region of HER2 alone and in complex with the Herceptin Fab. Nature 421: 756-760; Cho H S, Leahy D J (2002) Structure of the extracellular region of HER3 reveals an interdomain tether. Science 297: 1330-1333; Field L, Khim Y H (1972) Organic disulfides and related substances. 33. Sodium 4-(2-acetamidoethyldithio)butanesulfinate and related compounds as antiradiation drugs. J Med Chem 15: 312-315] reveals a complicated pattern of structural repeats that are held in place by disulfide bonds. Agents capable of disrupting disulfide bonds may preferentially destabilize the structures of HER2, EGFR, and HER3 and inhibit their oncogenic functions. Optimal disulfide bond disrupting agents (DDAs) would target extracellular disulfide bonds, be charged at physiological pH to minimize entry into cells in order to reduce off-target effects, and would employ chemistry that does not affect nucleic acids. DDAs meeting these criteria are expected to be toxic to cancer cells that depend on HER2 for proliferation and survival, but to be well tolerated by normal tissues. Herein we describe the identification of a class of molecules that fulfill these criteria.

SUMMARY OF THE INVENTION

In one aspect, the invention provides a compound of Formula I, or salt, solvate, hydrate or prodrug thereof:

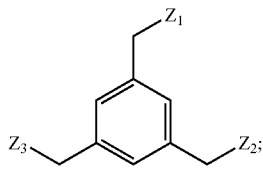

Formula I wherein,
each X is independently S or Se;
each Y is independently S or Se;
each Z is independently S or Se;
each $Z_1$, $Z_2$, and $Z_3$ is independently

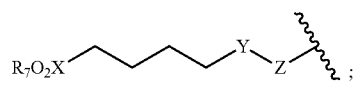

and
each $R_7$ is independently H, Na, K, optionally substituted alkyl, optionally substituted aryl, or optionally substituted arylalkyl.

In another aspect, the invention provides a compound of Formula II, or salt, solvate, hydrate or prodrug thereof:

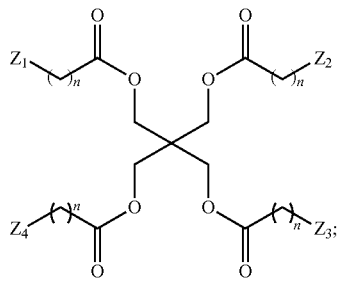

Formula II wherein,
each X is independently S or Se;
each Y is independently S or Se;
each Z is independently S or Se;
each $Z_1$, $Z_2$, $Z_3$, and $Z_4$ is independently

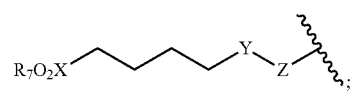

each $R_7$ is independently H, Na, K, optionally substituted alkyl, optionally substituted aryl, or optionally substituted arylalkyl; and
each n is independently 0, 1, 2 or 3.

In another aspect, the invention provides a compound of Formula III, or salt, solvate, hydrate or prodrug thereof:

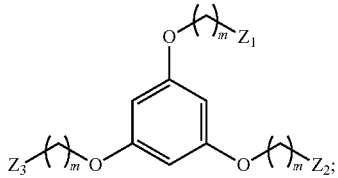

Formula III wherein,
each X is independently S or Se;
each Y is independently S or Se;
each Z is independently S or Se;
each $Z_1$, $Z_2$, and $Z_3$, is independently

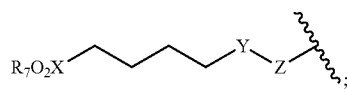

each $R_7$ is independently H, Na, K, optionally substituted alkyl, optionally substituted aryl, or optionally substituted arylalkyl; and
each m is independently 1, 2, 3, 4, 5, 6, 7, 8, 9, or 10.

In another aspect, the invention provides a compound of Formula IV, or salt, solvate, hydrate or prodrug thereof:

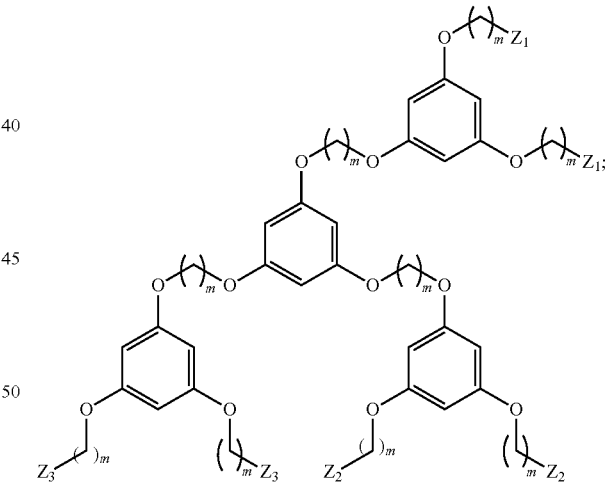

Formula IV wherein,
each X is independently S or Se;
each Y is independently S or Se;
each Z is independently S or Se;
each $Z_1$, $Z_2$, and $Z_3$, is independently

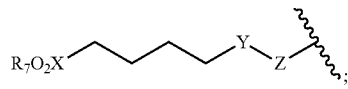

each $R_7$ is independently H, Na, K, optionally substituted alkyl, optionally substituted aryl, or optionally substituted arylalkyl; and each m is independently 1, 2, 3, 4, 5, 6, 7, 8, 9, or 10.

In another aspect, the invention provides a compound of Formula I, II, III, or IV, or salt, solvate, hydrate or prodrug thereof:

wherein, X is S; Y is S; and Z is S.

In another aspect, the invention provides a compound of Formula I, II, III, or IV, or salt, solvate, hydrate or prodrug thereof:

wherein, X is S; Y is S; Z is S; and $R_7$ is K or Na.

In another aspect, the invention provides a compound of Formula II, or salt, solvate, hydrate or prodrug thereof:

wherein, n is 1; X is S; Y is S; Z is S; and $R_7$ is K or Na.

In another aspect, the invention provides a compound of Formula III, or salt, solvate, hydrate or prodrug thereof:

wherein, m is 5; X is S; Y is S; Z is S; and $R_7$ is K or Na.

In another aspect, the invention provides a compound of Formula IV, or salt, solvate, hydrate or prodrug thereof:

wherein, m is 1; X is S; Y is S; Z is S; and $R_7$ is K or Na.

In another aspect, the invention provides a compound of Formula III, or salt, solvate, hydrate or prodrug thereof:

wherein, m is 5; X is S; Y is S; Z is S; and $R_7$ is Na.

In another aspect, the invention provides a compound of Formula IV, or salt, solvate, hydrate or prodrug thereof:

wherein, m is 1; X is S; Y is S; Z is S; and $R_7$ is Na.

In one aspect, the invention provides a method of treating a subject suffering from or susceptible to a cell proliferative disorder. The method includes administering to a subject in need thereof a therapeutically effective amount of a compound of Formula I, or salt, solvate, hydrate or prodrug thereof:

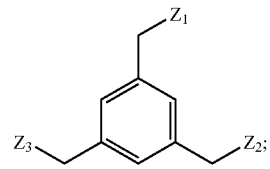

Formula I wherein,
each X is independently S or Se;
each Y is independently S or Se;
each Z is independently S or Se;
each $Z_1$, $Z_2$, and $Z_3$ is independently

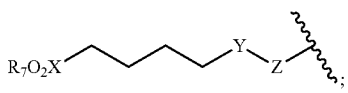

and each $R_7$ is independently H, Na, K, optionally substituted alkyl, optionally substituted aryl, or optionally substituted arylalkyl. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR. In a further aspect, the method includes administration of an additional therapeutic agent (e.g., EGFR inhibitors, HER2 inhibitors, trastuzumab, pertuzumab, gefitinib, lapatinib, other anticancer agents cited herein).

In one aspect, the invention provides a method of treating a subject suffering from or susceptible to a cell proliferative disorder. The method includes administering to a subject in need thereof a therapeutically effective amount of a compound of Formula II, or salt, solvate, hydrate or prodrug thereof:

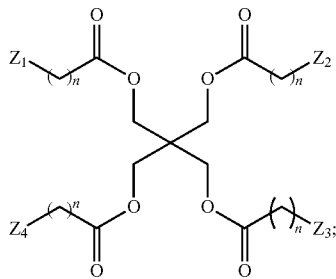

Formula II wherein,
each X is independently S or Se;
each Y is independently S or Se;
each Z is independently S or Se;
each $Z_1$, $Z_2$, $Z_3$, and $Z_4$ is independently

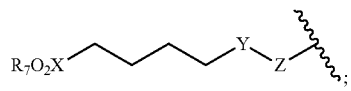

each $R_7$ is independently H, Na, K, optionally substituted alkyl, optionally substituted aryl, or optionally substituted arylalkyl; and each n is independently 0, 1, 2 or 3.

In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR. In a further aspect, the method includes administration of an additional therapeutic agent (e.g., EGFR inhibitors, HER2 inhibitors, trastuzumab, pertuzumab, gefitinib, lapatinib, other anticancer agents cited herein).

In one aspect, the invention provides a method of treating a subject suffering from or susceptible to a cell proliferative disorder. The method includes administering to a subject in need thereof a therapeutically effective amount of a compound of Formula I, II, III, or IV, or salt, solvate, hydrate or prodrug thereof. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR. In a further aspect, the method includes administration of an additional therapeutic agent (e.g., EGFR inhibitors, HER2 inhibitors, trastuzumab, pertuzumab, gefitinib, lapatinib, other anticancer agents cited herein).

In another aspect, the invention provides a method of inhibiting cancer cell metastasis. The method includes administering to a subject in need thereof a therapeutically effective amount of a compound of Formula I, II, III, or IV, or salt, solvate, hydrate or prodrug thereof. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR. In a further aspect, the method includes administration of an additional therapeutic agent (e.g., EGFR inhibitors, HER2 inhibitors, trastuzumab, pertuzumab, gefitinib, lapatinib, other anticancer agents cited herein).

In another aspect, the invention provides a kit for treating a cell proliferative disorder in a subject. The kit includes a compound of Formula I, II, III, or IV, or salt, solvate, hydrate or prodrug thereof. In certain embodiments, the cell proliferation disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR. In a further aspect, the kit includes an additional therapeutic agent (e.g., EGFR inhibitors, HER2 inhibitors, trastuzumab, pertuzumab, gefitinib, lapatinib, other anticancer agents cited herein).

In certain embodiments, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. The kit includes a compound of Formula I, II, III, or IV, or salt, solvate, hydrate or prodrug thereof. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of inhibiting EGFR, HER2, and/or HER3. The method includes administering a therapeutically effective amount of a compound of Formula I, II, III, or IV, or salt, solvate, hydrate or prodrug thereof. In another aspect, the compound inhibits or is capable of inhibiting at least two of EGFR, HER2, and HER3. In another aspect, the compound inhibits or is capable of inhibiting all three of EGFR, HER2, and HER3. In a further aspect, the method includes administration of an additional therapeutic agent (e.g., EGFR inhibitors, HER2 inhibitors, trastuzumab, pertuzumab, gefitinib, lapatinib, other anticancer agents cited herein).

In another aspect, the invention provides a compound that is:

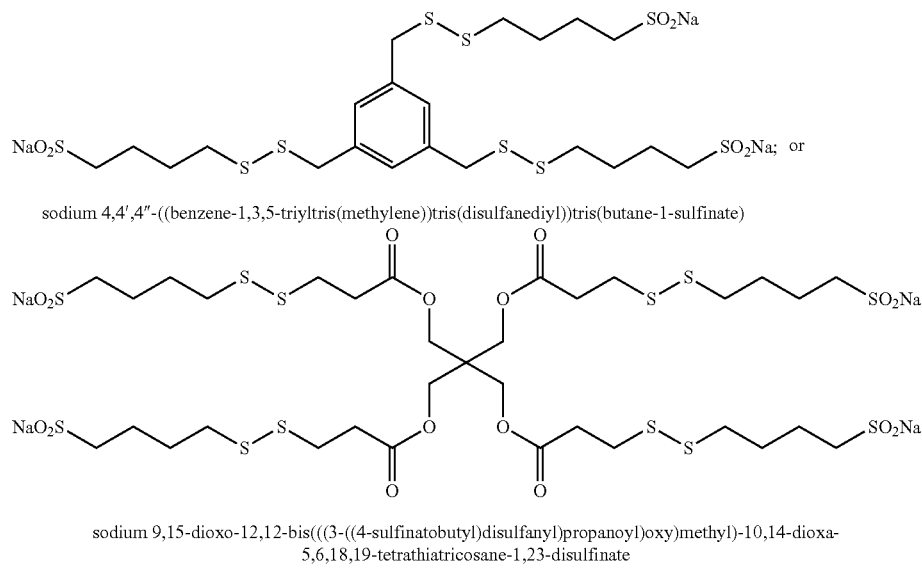

sodium 4,4',4''-((benzene-1,3,5-triyltris(methylene))tris(disulfanediyl))tris(butane-1-sulfinate)

sodium 9,15-dioxo-12,12-bis(((3-((4-sulfinatobutyl)disulfanyl)propanoyl)oxy)methyl)-10,14-dioxa-5,6,18,19-tetrathiatricosane-1,23-disulfinate or salt, solvate, hydrate or prodrug thereof.

Other aspects and embodiments of the invention are disclosed infra.

BRIEF DESCRIPTION OF THE DRAWINGS

The present invention is further described below with reference to the following non-limiting examples and with reference to the following figures, in which:

FIG. 1A. The specified cell lines were treated with the indicated RBF3 concentrations for 24 hours and analyzed for the ER stress marker GRP78 by immunoblot (left panel). The right panel indicates the status of EGFR or HER2 expression and DDA sensitivity. FIG. 1B. Proliferation of MDA-MB-468 cells treated for 24 hours with the indicated concentrations of RBF3 in the presence or absence of 20 ng/ml EGF as assessed by tritiated thymidine incorporation. Results are presented as the mean±standard deviation of triplicate determinations. FIG. 1C. DDA sensitive or resistant cell lines were treated for 24 hours with increasing concentrations of RBF3 and extracts were analyzed by immunoblot for markers related to ER stress. FIG. 1D. The time course of RBF3 responses in MDA-MB-468 cells was compared with that of the ER stress inducers tunicamycin (500 ng/ml) and thapsigargin (400 nM) by immunoblot analysis. FIG. 1E. Luciferase reporter assays measuring the impact of ectopically expressed ATF6 and 20 µM RBF3 on the activity of an ATF6-responsive promoter construct. Results are normalized to micrograms of protein extract assayed, and are presented as the mean±standard deviation of triplicate determinations. FIG. 1F. Extracts from HEK 293 cells transiently transfected as indicated and treated with or without 20 μM RBF3 for 24 hours were analyzed by immunoblot.

FIG. 2A. MDA-MB-468 or BT474 cells were treated for 8 hours with 20 μM RBF3, 20 μM Cycloheximide (CHX), or 5 μg/ml Puromycin either alone or in the indicated combinations and cell extracts were analyzed by immunoblot. FIG. 2B. MDA-MB-468 or BT474 cells were treated for 24 hours with 20 μM RBF3 or 20 μM CHX in the indicated combinations and cell extracts were analyzed by immunoblot. FIG. 2C. MDA-MB-468 cells were treated with RBF3 and/or CHX as indicated for 2, 4, 8, or 16 hours and cell extracts were prepared and analyzed by immunoblot. FIG. 2D. MDA-MB-468 or BT474 cells were treated for 24 hours with 20 μM RBF3 combined with increasing concentrations of CHX and cell extracts were analyzed by immunoblot. FIG. 2E. The indicated T47D stable cell lines were treated for 24 hours with 20 ng/ml EGF, 20 μM NSC624205, or EGF+NSC624205 and cell extracts were analyzed by immunoblot. FIG. 2F. Vector control or EGFR overexpressing T47D cells were treated with 20 μM RBF3 for 18 hours and cell extracts were analyzed by immunoblot. FIG. 2G. Vector control or EGFR overexpressing T47D cells were treated with vehicle or 20 μM RBF3 for 15 (left panel) or 24 (right panel) hours and cell extracts were analyzed by immunoblot.

FIG. 3A. MDA-MB-468 and BT474 cells were treated for 24 hours with 20 μM RBF3, 100 μM 2-Aminoethoxydiphenyl Borate (2-APB), or 4 mM 2-deoxyglucose (2-DOG) in the indicated combinations and cell extracts were analyzed by immunoblot. FIG. 3B. MDA-MB-468 cells were treated for 24 hours with 20 μM RBF3, 400 nM thapsigargin, 500 ng/ml tunicamycin or dithiothreitol (DTT) at the indicated concentrations and cell extracts were analyzed by immunoblot. The effects of these same treatments on the splicing of the mRNA coding for XBP1s was assessed by reverse transcription of mRNA followed by DNA amplification (RT-PCR). FIG. 3C. BT474 cells were treated for 24 hours with 20 μM RBF3, 400 nM thapsigargin, 500 ng/ml tunicamycin, or DTT at the indicated concentrations, and cell extracts were analyzed by immunoblot. The effects of these same treatments on the splicing of the mRNA coding for XBP1s was assessed by reverse transcription of mRNA followed by DNA amplification (RT-PCR). FIG. 3D. Wild type or eIF2α [S51A] double knock-in mutant MEFs were treated for 24 hours with 20 μM RBF3, 400 nM thapsigargin, 500 ng/ml tunicamycin, 5 mM DTT, or vehicle and cell extracts were prepared and analyzed by immunoblot.

FIG. 4A-4I. DDAs may be useful in combination therapies for combating resistance to mTORC 1-, EGFR-, or HER2- targeted agents. FIG. 4A. MDA-MB-468 cells were treated for 24 hours with RBF3 alone at the indicated concentrations, or RBF3 combined with 2.5 μM Gefitinib or 2.5 μM Lapatinib, and cell extracts were prepared and analyzed by immunoblot. FIG. 4B. Micrographs of the HCI-012 cell line after a 24 hour treatment with vehicle or 20 μM RBF3. FIG. 4C. Immunoblot analysis of HCI-012 cell extracts after the indicated 24 hour treatments. FIG. 4D. Micrographs of HCC1954 cells after 24 hour treatments with 20 μM RBF3, 100 nM rapamycin, 20 μM Lapatinib, or the indicated drug combinations. FIG. 4E. Immunoblot analysis of HCC1954 cells treated as in FIG. 4D. FIG. 4F. Viability of HCC1954 cells after 24 hours of the indicated treatments using the MTT assay. Results are presented as the mean±standard deviation of triplicate determinations. FIG. 4G. Immunoblot analysis of BxPC3 pancreatic cancer cell extracts after a 24 hour treatment with 20 μM RBF3, 20 μM Lapatinib, or the two drugs combined. FIG. 4H. Extracts from TSC2-Ang1 cells treated with 20 μM RBF3, 100 nM rapamycin, or RBF3+ rapamycin were analyzed by immunoblot. FIG. 4I. Micrographs of TSC2-Ang1 cells treated as in FIG. 4H. White arrows denote cells undergoing division. Black arrows indicate cell death.

FIG. 5A. Structure of bivalent DDA RBF3 and novel trivalent (Bn-DDA) and tetravalent (PEMP-DDA) DDAs. FIG. 5B. Immunoblot analyses of MDA-MB-468 cells treated with the indicated concentrations of DDAs for 24 hours. The results in FIG. 5B were replicated a total of three times, and quantified with respect to changes in EGFR levels, Akt phosphorylation on Thr308, PARP cleavage (cPARP), and GRP78 expression in FIGS. 5C, 5D, 5E, and 5F, respectively. Statistically significant differences are denoted with P-values. FIG. 5G. MTT assays performed on cells treated with the indicated concentrations of DDAs for 72 hours. FIG. 5H. Structural alterations to the parent cyclic, monovalent DDA, DTDO. I. Extracts from MDA-MB-468 cells treated with the DTDO or its derivatives for 24 hours at the specified concentrations were analyzed by immunoblot.

FIG. 6A. Immunoblot analyses of BT474 cells treated with the indicated concentrations of DDAs for 24 hours. The results in FIG. 6A were replicated a total of three times, and quantified with respect to changes in HER2 levels and PARP cleavage (cPARP) in FIGS. 6B and 6C, respectively. Statistically significant differences are denoted with P-values. FIG. 6D. MTT assays performed on cells treated with the indicated concentrations of DDAs for 72 hours.

FIG. 7A. Cardiomyocytes differentiated from iPSCs were treated as indicated for 24 hours and photographed (left panel). Cardiomyocytes treated in parallel were subjected to immunoblot analysis with the indicated antibodies (top right panel), and MTT cell viability assays (bottom right panel). FIG. 7B. Photomicrographs of MCF10/DCIS cells treated for 24 hours as indicated. Higher magnification insets show ongoing cell division.

FIG. 8A. DDAs function to suppress tumor cell division and survival through mechanisms involving suppression of Akt phosphorylation, downregulation of EGFR (HER1), HER2, and HER3, and activation of UPR. Overexpression of EGFR or HER2 potentiates each of these mechanisms. FIG. 8B. At normal expression levels, EGFR and HER2 are folded efficiently and do not induce ER stress (upper panel). Overexpression of EGFR or HER2 cooperates with DDA treatment, which blocks disulfide bond formation and protein folding, to activate UPR (lower panel). Red asterisks denote ER stress markers examined experimentally in FIGS. 1A-6D.

FIG. 11A. Micrograph of a Hematoxylin and Eosin (H&E)-stained section of a xenograft tumor derived from the HCI-012 cell line growing in a mouse mammary fat pad. FIG. 11B. HCI-012 cells growing in Conditional Cell Reprogramming (CCR) Medium (left panel) or incubated in 10% FBS-DMEM (center and right panels). Note that when not grown in CCR medium the HCI-012 cells begin to senesce and die.

FIG. 12A. Bn-DDA, FIG. 12B. PEMP-DDA, FIG. 12C. cis-DAcDTDO, FIG. 12D. trans-DAcDTDO, FIG. 12E. cis-DHDTDO, FIG. 12F. trans-DHDTO.

DETAILED DESCRIPTION OF THE INVENTION

Definitions

Figure 1A:
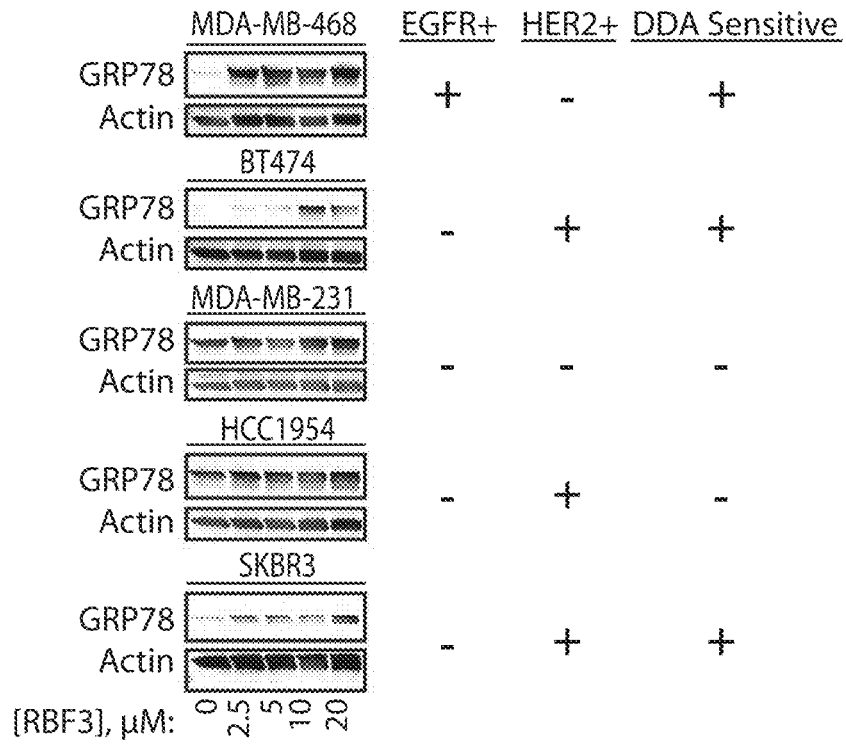
FIGS. 1A-1F. DDA responsiveness parallels activation of the unfolded protein response.

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally affect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In certain embodiments, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In one embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In certain embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a cell proliferative disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, or about 0.01 to 25 mg/kg body weight, or about 0.1 to 20 mg/kg body weight, or about 1 to 10 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or can include a series of treatments. In one example, a subject is treated with a compound of the invention in the range of between about 0.1 to 20 mg/kg body weight, one time per week for between about 1 to 10 weeks, or between 2 to 8 weeks, or between about 3 to 7 weeks, or for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In certain embodiments, this term refers to any qualitative or quantitative improved therapeutic property of a compound of the invention, such as reduced toxicity.

The term "cell proliferative disorder" includes disorders involving the undesired or uncontrolled proliferation of a cell. Examples of such disorders include, but are not limited to, tumors (e.g., brain, lung (small cell and non-small cell), ovary, prostate, breast or colon) or other carcinomas or sarcomas (e.g., leukemia, lymphoma).

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-($C_1$-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a cell to proliferate in response to exposure to a compound of the invention, e.g., the inhibition of proliferation of at least a sub-population of cells in an animal such that a desired end result is achieved, e.g., a therapeutic result.

The term "obtaining" as in "obtaining a compound capable of inhibiting CDCP1" is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a cell proliferative disorder.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" of the invention includes all vertebrates, e.g., mammals; e.g., rodents; e.g., mice; and non-mammals, such as non-human primates; e.g., sheep, dog, cow, chickens, amphibians, reptiles, etc.

The term "susceptible to a cell proliferative disorder" is meant to include subjects at risk of developing disorder of cell proliferation, e.g., cancer, i.e., subjects suffering from viral infection with cancer causing viruses, subjects that have been exposed to ionizing radiation or carcinogenic compounds, subjects having a family or medical history of cancer, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention refers to an amount of an agent which is effective, upon single or multiple dose administration to the patient, in inhibiting cell proliferation and/or symptoms of a cell proliferative disorder, or in prolonging the survivability of the patient with such a cell proliferative disorder beyond that expected in the absence of such treatment.

With respect to the nomenclature of a chiral center, terms "d" and "1" configuration are as defined by the IUPAC Recommendations. As to the use of the terms, diastereomer, racemate, epimer and enantiomer will be used in their normal context to describe the stereochemistry of preparations.

2. Compounds of the Invention

In one aspect, the invention provides a compound that inhibits or is capable of inhibiting EGFR, HER2, and/or HER3. In another aspect, the compound inhibits or is capable of inhibiting at least two of EGFR, HER2, and HER3. In another aspect, the compound inhibits or is capable of inhibiting all three of EGFR, HER2, and HER3. In another aspect, the compound is capable of treating HER2-positive breast cancer. In another aspect, the compound is capable of treating breast cancer modulated by EGFR, HER2, and/or HER3.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

3. Uses of the Compounds of the Invention

As described herein below, it has now surprisingly been found that the compounds of the invention and analogs can inactivate EGFR, HER2, and/or HER3, and thereby treat disorders of cell proliferation, including cancer. Thus, compounds of the invention overcome the deficiencies of treating breast cancer with HER2-targeted antibodies (e.g., Trastuzumab and Pertuzumab), which only specifically target the single receptor, HER2, to which 66-88% of HER2-positive tumors exhibit primary resistance.

Thus, in one embodiment, the invention provides methods for treating a subject for a cell proliferative disorder, by administering to the subject an effective amount of a compound of the invention (e.g., a compound of any formula herein or otherwise described herein). A cell proliferative disorder includes cancer. In certain embodiments, the subject is a mammal, e.g., a primate, e.g., a human.

A further aspect presents a method of treating a subject suffering from or susceptible to cancer, including administering to the subject an effective amount of a compound of the invention (e.g., a compound of any formula herein or otherwise described herein) to thereby treat the subject suffering from or susceptible to cancer.

In certain embodiments, the methods of the invention include administering to a subject a therapeutically effective amount of a compound of the invention in combination with another pharmaceutically active compound. Examples of pharmaceutically active compounds include compounds known to treat cell proliferative disorders, e.g., EGFR inhibitors, HER2 inhibitors, trastuzumab, pertuzumab, gefitinib, lapatinib, other anticancer agents cited herein). Other pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

In certain embodiments, the compound of the invention can be used in combination therapy with conventional cancer chemotherapeutics. Conventional treatment regimens for leukemia and for other tumors include radiation, surgery, drugs, or combinations thereof. In addition to radiation, the following drugs, usually in combinations with each other, are often used to treat acute leukemias: vincristine, prednisone, methotrexate, mercaptopurine, cyclophosphamide, and cytarabine. In chronic leukemia, for example, busulfan, melphalan, and chlorambucil can be used in combination. Most conventional anti-cancer drugs are highly toxic and tend to make patients quite ill while undergoing treatment. Vigorous therapy is based on the premise that unless every cancerous cell is destroyed, the residual cells will multiply and cause a relapse.

Determination of a therapeutically effective anti-proliferative amount or a prophylactically effective anti-proliferative amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention is expected to vary from about 0.1 milligram per kilogram of body weight per day (mg/kg/day) to about 100 mg/kg/day.

Compounds determined to be effective for the prevention or treatment of cell proliferative disorders in animals, e.g., dogs, chickens, and rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals.

The identification of those patients who are in need of prophylactic treatment for cell proliferative disorders is well within the ability and knowledge of one skilled in the art. Certain of the methods for identification of patients which are at risk of developing cell proliferative disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a cell proliferative disorder by methods well known in the art (e.g., determining tumor size or screening for tumor markers where the cell proliferative disorder is cancer) and then administering a therapeutically effective amount of an inhibitor of cell proliferation (e.g., a compound of any formula herein or otherwise described herein) according to the invention to the subject. After an appropriate period of time after the administration of the compound (e.g., 1 day, 1 week, 2 weeks, one month, six months), the extent of the cell proliferative disorder is determined again. The modulation (e.g., decrease) of the extent or invasiveness of the cell proliferative disorder indicates efficacy of the treatment. The extent or invasiveness of the cell proliferative disorder may be determined periodically throughout treatment. For example, the extent or invasiveness of the cell proliferative disorder may be checked every few hours, days or weeks to assess the further efficacy of the treatment. A decrease in extent or invasiveness of the cell proliferative disorder indicates that the treatment is efficacious. The method described may be used to screen or select patients that may benefit from treatment with an inhibitor of a cell proliferative disorder.

As used herein, "obtaining a biological sample from a subject," includes obtaining a sample for use in the methods described herein. A biological sample is described above.

Yet another aspect presents a method to identify a compound that inhibits cell proliferation by measuring the compound's ability to inhibit or inactivate EGFR, HER2, and/or HER3. The method may include utilizing a homology model of EGFR, HER2, and/or HER3. Compounds may be computer modeled into or on a EGFR, HER2, and/or HER3 binding site of the homology model to identify EGFR, HER2, and/or HER3 inhibitory compounds. Once potential inhibitory compounds are identified, the compounds may be screened using cellular assays, such as the ones identified below in the Examples and competition assays known in the art. Compounds identified that affect EGFR, HER2, and/or HER3 signaling could be inhibitors or activators (more preferably inhibitors) of EGFR, HER2, and/or HER3 binding and could be useful therapeutic agents.

In another aspect, a compound of the invention is packaged in a therapeutically effective amount with a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In another aspect, the invention provides methods for inhibiting cell proliferation. In one embodiment, a method of inhibiting cell proliferation (or a cell proliferative disorder) according to the invention includes contacting cells with a compound capable of inhibiting EGFR, HER2, and/or HER3 signaling. In another embodiment, a method of inhibiting cell proliferation (or a cell proliferative disorder) according to the invention includes contacting cells with a compound capable of inhibiting EGFR, HER2, and/or HER3 signaling in the cells. In either embodiment, the contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of inhibiting a cell proliferative disorder in a subject include administering an effective amount of a compound of the invention to the subject. The administration may be by any route of administering known in the pharmaceutical arts. The subject may have a cell proliferative disorder, may be at risk of developing a cell proliferative disorder, or may need prophylactic treatment prior to anticipated or unanticipated exposure to conditions capable of increasing susceptibility to a cell proliferative disorder, e.g., exposure to carcinogens or to ionizing radiation.

In one aspect, a method of monitoring the progress of a subject being treated with a compound capable of inhibiting EGFR, HER2, and/or HER3 includes determining the pre-treatment status (e.g., size, growth rate, or invasiveness of a tumor) of the cell proliferative disorder, administering a therapeutically effective amount of a EGFR, HER2, and/or HER3 inhibitor to the subject, and determining the status of the cell proliferative disorder after an initial period of treatment with the EGFR, HER2, and/or HER3 inhibitor, wherein the modulation of the status indicates efficacy of the treatment.

In one aspect, a method of monitoring the progress of a subject being treated with a compound capable of inhibiting EGFR, HER2, and/or HER3 signaling includes determining the pre-treatment status (e.g., size, growth rate, or invasiveness of a tumor) of the cell proliferative disorder, administering a therapeutically effective amount of a compound capable of inhibiting EGFR, HER2, and/or HER3 signaling to the subject, and determining the status (e.g., size, growth rate, or invasiveness of a tumor) of the cell proliferative disorder after an initial period of treatment with the compound capable of inhibiting EGFR, HER2, and/or HER3 signaling, wherein the modulation of the status indicates efficacy of the treatment.

In one aspect, a method of monitoring the progress of a subject being treated with a compound capable of inhibiting EGFR, HER2, and/or HER3 signaling includes determining the pre-treatment status (e.g., size, growth rate, or invasiveness of a tumor) of the cell proliferative disorder, administering a therapeutically effective amount of a compound capable of inhibiting EGFR, HER2, and/or HER3 signaling to the subject, and determining the status (e.g., size, growth rate, or invasiveness of a tumor) of the cell proliferative disorder after an initial period of treatment with the compound capable of inhibiting EGFR, HER2, and/or HER3 signaling, wherein the modulation of status is an indication that the cell proliferative disorder is likely to have a favorable clinical response to treatment with a compound capable of inhibiting EGFR, HER2, and/or HER3 signaling.

The subject may be at risk of a cell proliferative disorder, may be exhibiting symptoms of a cell proliferative disorder, may be susceptible to a cell proliferative disorder and/or may have been diagnosed with a cell proliferative disorder.

The initial period of treatment may be the time in which it takes to establish a stable and/or therapeutically effective blood serum level of the compound capable of inhibiting EGFR, HER2, and/or HER3 signaling, or the time in which it take for the subject to clear a substantial portion of the compound, or any period of time selected by the subject or healthcare professional that is relevant to the treatment.

If the modulation of the status indicates that the subject may have a favorable clinical response to the treatment, the subject may be treated with the compound. For example, the subject can be administered a therapeutically effective dose or doses of the compound.

In another aspect, the invention provides methods for inhibiting EGFR, HER2, and/or HER3 signaling in a cell. The methods include contacting the cell with an effective amount of a compound capable of inhibiting EGFR, HER2, and/or HER3 signaling, such that the signaling of EGFR, HER2, and/or HER3 is reduced The contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, the invention provides methods for identifying an inhibitor of EGFR, HER2, and/or HER3. The methods include contacting EGFR, HER2, and/or HER3 with a compound capable of inhibiting EGFR, HER2, and/or HER3, such that the signaling of EGFR, HER2, and/or HER3 is inhibited.

The EGFR, HER2, and/or HER3 may be within a cell, isolated from a cell, recombinantly expressed, purified or isolated from a cell or recombinant expression system or partially purified or isolated from a cell or recombinant expression system.

The contacting may be in vitro, e.g., by addition of the compound to a solution containing purified EGFR, HER2, and/or HER3, or, if EGFR, HER2, and/or HER3 is present in cells, by adding the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

Kits of the invention include kits for treating a cell proliferative disorder in a subject. The invention also includes kits for downregulating expression of EGFR, HER2, and/or HER3, stabilizing an interaction of EGFR, HER2, and/or HER3, assessing the efficacy of a treatment for a cell proliferative disorder in a subject, monitoring the progress of a subject being treated for a cell proliferative disorder, selecting a subject with a cell proliferative disorder for treatment according to the invention, and/or treating a subject suffering from or susceptible to a cell proliferative disorder. The kit may include a compound of the invention (e.g., a compound of any formula herein or otherwise described herein) and instructions for use. The instructions for use may include information on dosage, method of delivery, storage of the kit, etc. The kits may also include reagents, for example, test compounds, buffers, media (e.g., cell growth media), cells, etc. Test compounds may include known compounds or newly discovered compounds, for example, combinatorial libraries of compounds. One or more of the kits of the invention may be packaged together, for example, a kit for assessing the efficacy of a treatment for a cell proliferative disorder may be packaged with a kit for monitoring the progress of a subject being treated for a cell proliferative disorder according to the invention.

The present methods can be performed on cells in culture, e.g. in vitro or ex vivo, or on cells present in an animal subject, e.g., in vivo. Compounds of the inventions can be initially tested in vitro using primary cultures of proliferating cells, e.g., transformed cells, tumor cell lines, and the like.

Alternatively, the effects of compound of the invention can be characterized in vivo using animals models.

4. Pharmaceutical Compositions

The invention also provides a pharmaceutical composition, comprising an effective amount of a compound of the invention (e.g., a compound capable of inhibiting EGFR, HER2, and/or HER3, a compound capable of stabilizing the interaction between the compound and EGFR, HER2, and/or HER3, or a compound of any formula herein or otherwise described herein) and a pharmaceutically acceptable carrier. In a further embodiment, the effective amount is effective to treat a cell proliferative disorder, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount of a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, or from about 5 percent to about 70 percent, or from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH 5 to pH 7, with a pH of about pH 5.5 being typical.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407, 713; 5,352,456; 5,332,213; 5,336,168; 5,290,561; 5,254, 346; 5,164,189; 5,163,899; 5,088,977; 5,087,240; 5,008, 110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

Examples

The invention is further illustrated by the following examples which are intended to illustrate but not limit the scope of the invention.

DDAs Induce ER Stress—

Figure 1B:
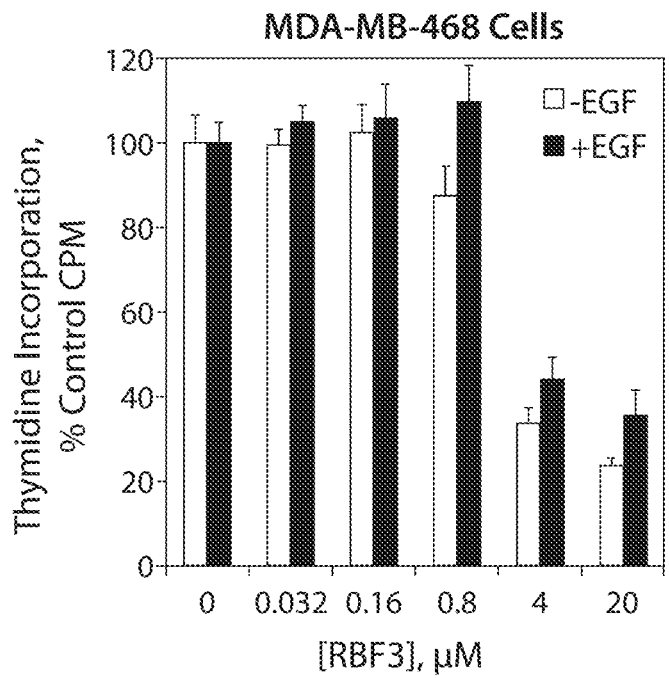
Figure 1C:
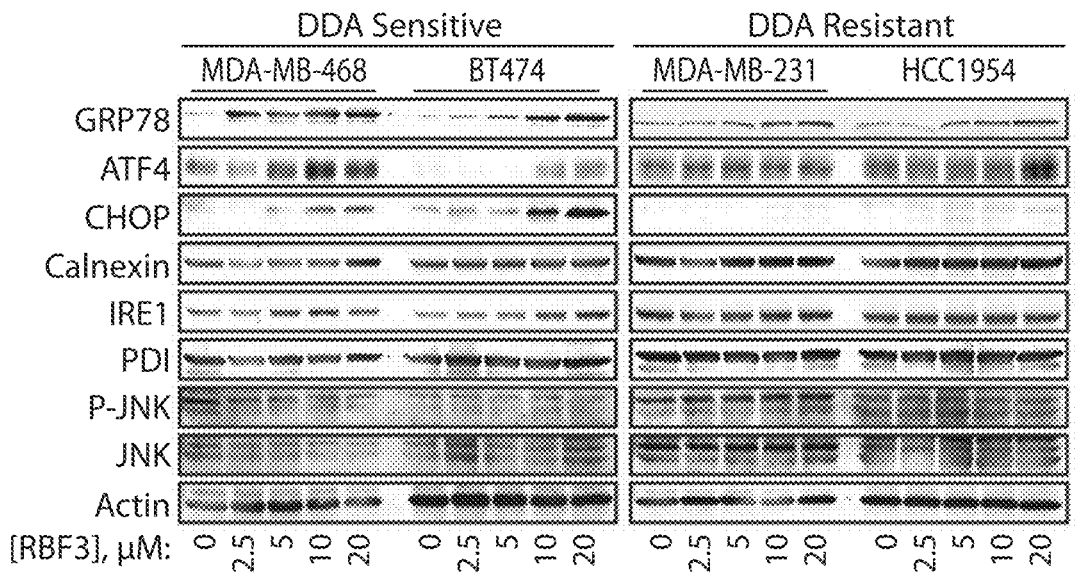
Figure 1D:
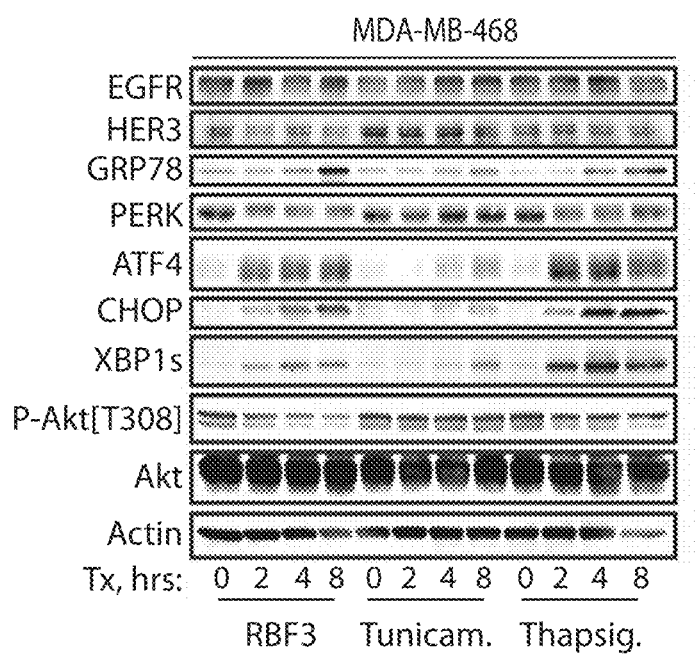
Figure 1E:
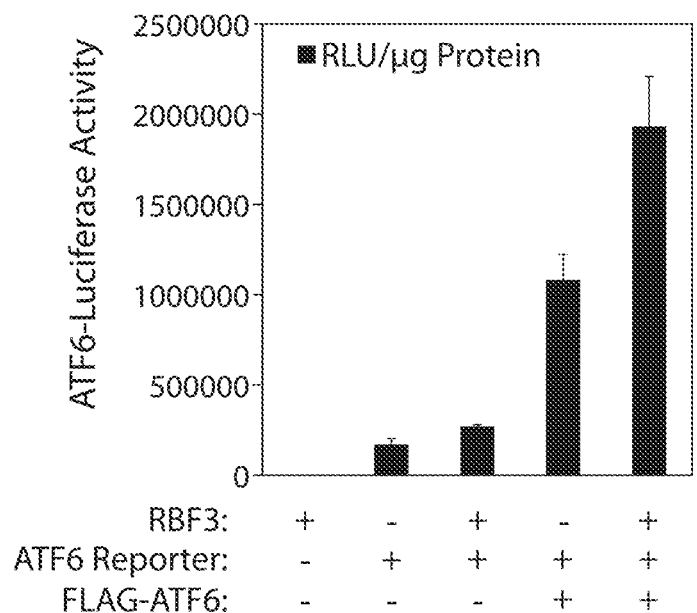
Figure 1F:
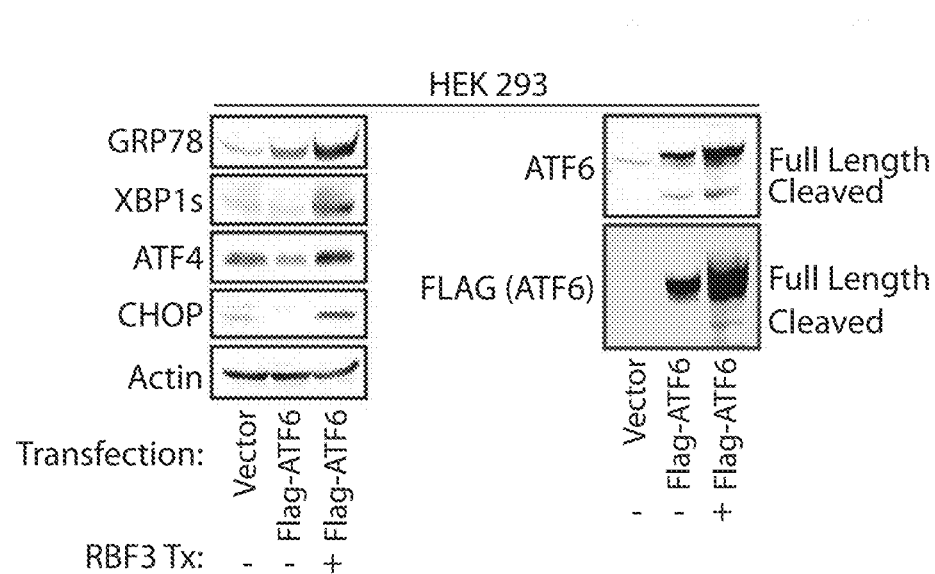

Since disulfide bond formation occurs in the Endoplasmic Reticulum (ER), and HER2$^+$ breast cancers are particularly sensitive to DDAs [33] and ER stress/ERAD [25], we examined whether DDAs activate the Unfolded Protein Response (UPR). In the DDA-sensitive MDA-MB-468, BT474, and SKBR3 lines, DDAs activated ER stress as indicated by GRP78 upregulation (FIG. 1A). The DDA-resistant MDA-MB-231 and HCC1954 lines exhibited high basal GRP78 expression, suggesting that they have adapted to persistent ER stress. DDAs upregulated GRP78 at the lowest concentrations tested, 2.5 µM, in the MDA-MB-468 line. Suppression of MDA-MB-468 cell proliferation commenced between 0.8 and 4 µM, suggesting that inhibition of cell division and activation of ER stress occur over a similar concentration range (FIG. 1B). The ER stress response is mediated by the upstream sensors PERK, IRE1, and ATF6. PERK-dependent activation of an ATF4-CHOP transcriptional axis contributes to cell death in response to unresolvable ER stress [34, 35]. DDA-sensitive cell lines exhibited upregulation of ATF4 and CHOP in a concentration-dependent manner, while the resistant cell lines expressed high basal ATF4 levels and lacked CHOP expression (FIG. 1C). Although the IRE1-Jun kinase axis was previously implicated in ER stress-mediated cell death [36], DDAs did not alter activating Jun kinase (JNK) phosphorylation in any of the cell lines. Comparison of RBF3 with the ER stress inducers tunicamycin and thapsigargin showed that RBF3 elicited ER stress comparably, but was more effective in suppressing Akt phosphorylation (FIG. 1D). The observation that RBF3 upregulates XBP1s demonstrates that RBF3 activates the arms of the ER stress response involving the IRE1-XBP1s and PERK-ATF4-CHOP cassettes. Transcriptional reporter assays in HEK293 cells were performed to evaluate whether DDAs activate the third ER stress sensor, ATF6. RBF3 did not significantly stimulate basal ATF6-luciferase activity, but potentiated the transcriptional activity of ectopically expressed ATF6 (FIG. 1E). Immunoblot analysis of HEK293 cell extracts demonstrated that overexpression of ATF6 increased endogenous GRP78 expression, but did not increase XBP1s, ATF4, or CHOP levels. RBF3 combined with ATF6 overexpression robustly upregulated GRP78 and increased XBP1s, ATF4, and CHOP levels (FIG. 1F). ATF6 activation involves cleavage to release its cytoplasmic domain, which travels to the nucleus to regulate transcription. RBF3 increased the expression of exogenous ATF6, and resulted in higher levels of the cleaved, transcriptionally active form of ATF6. The results in FIG. 1 show that DDAs activate all three branches of UPR.

Ongoing protein synthesis is required for DDA induction of UPR—

Figure 2A:
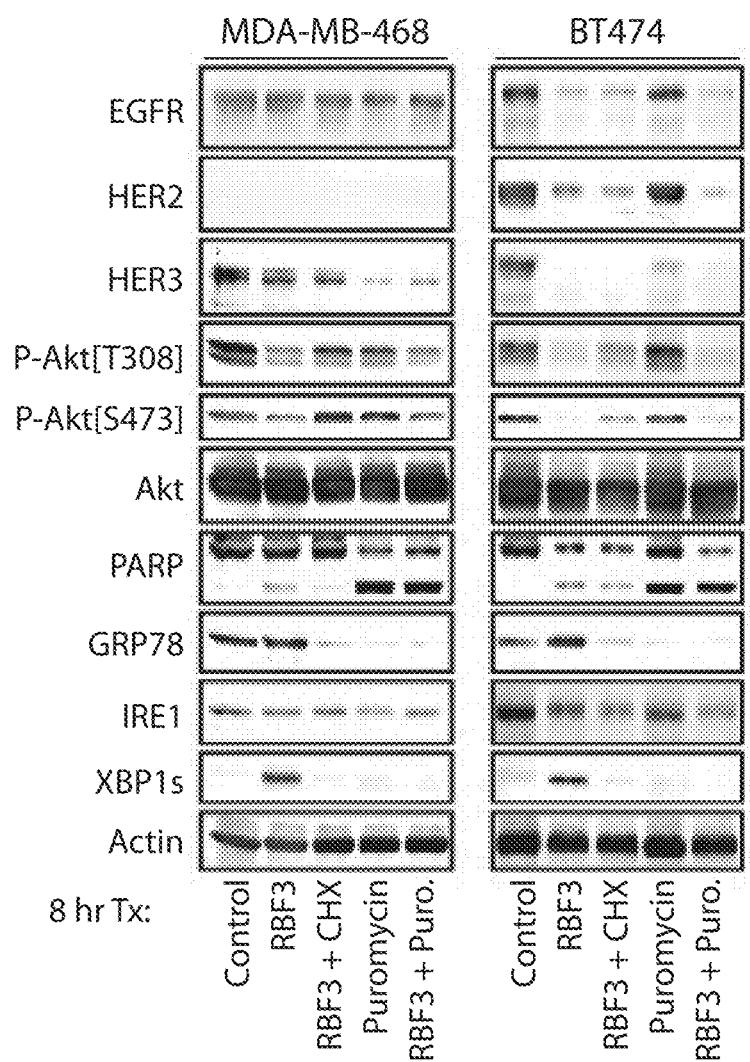
FIGS. 2A-2G. Ongoing protein synthesis is required for DDA induction of UPR, and elevated DDA sensitivity due to forced EGFR or HER2 overexpression correlates with enhanced HER3 downregulation and increased ER stress.
Figure 2B:
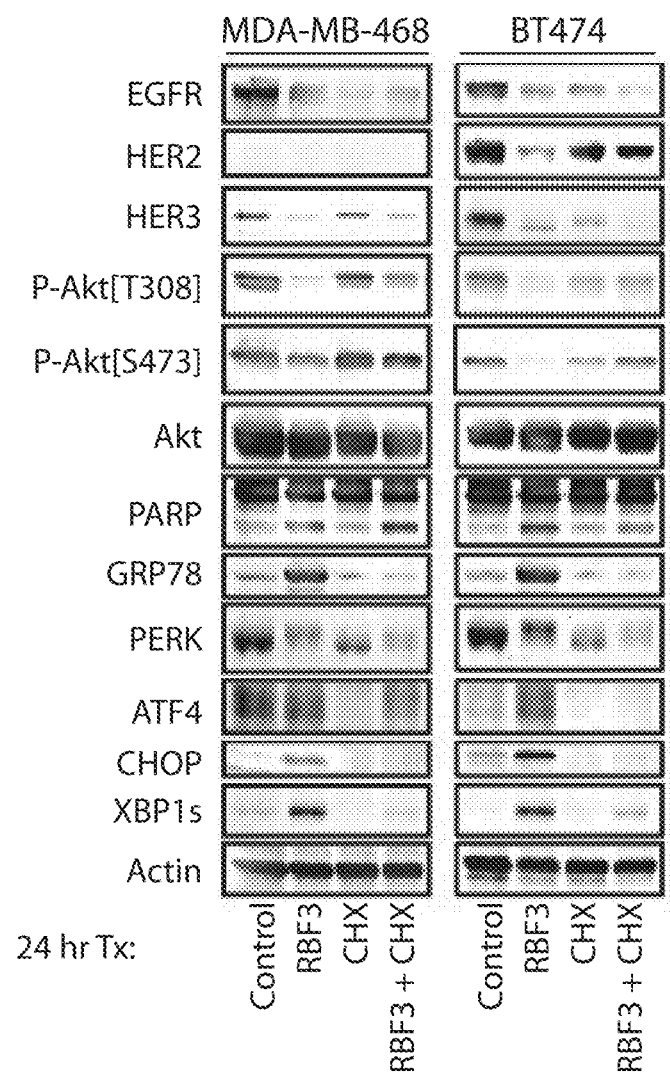
Figure 2C:
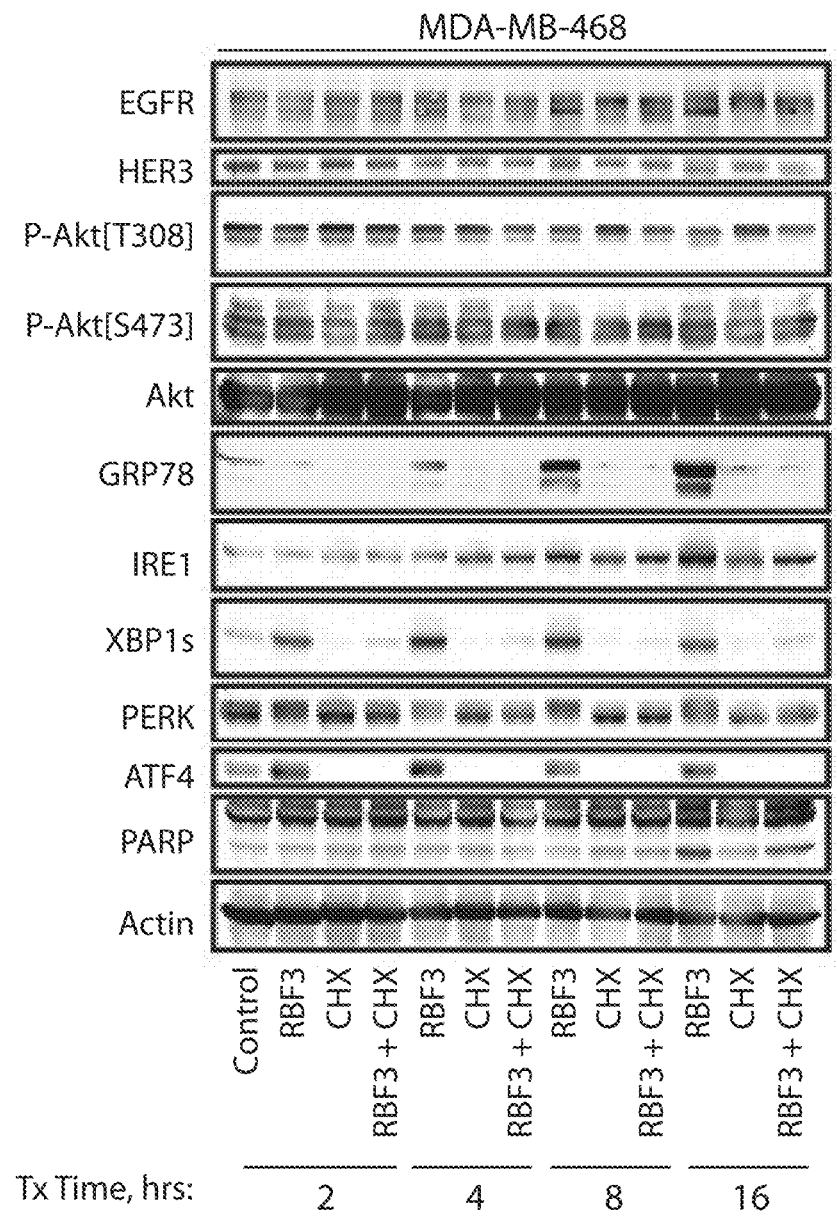
Figure 2D:
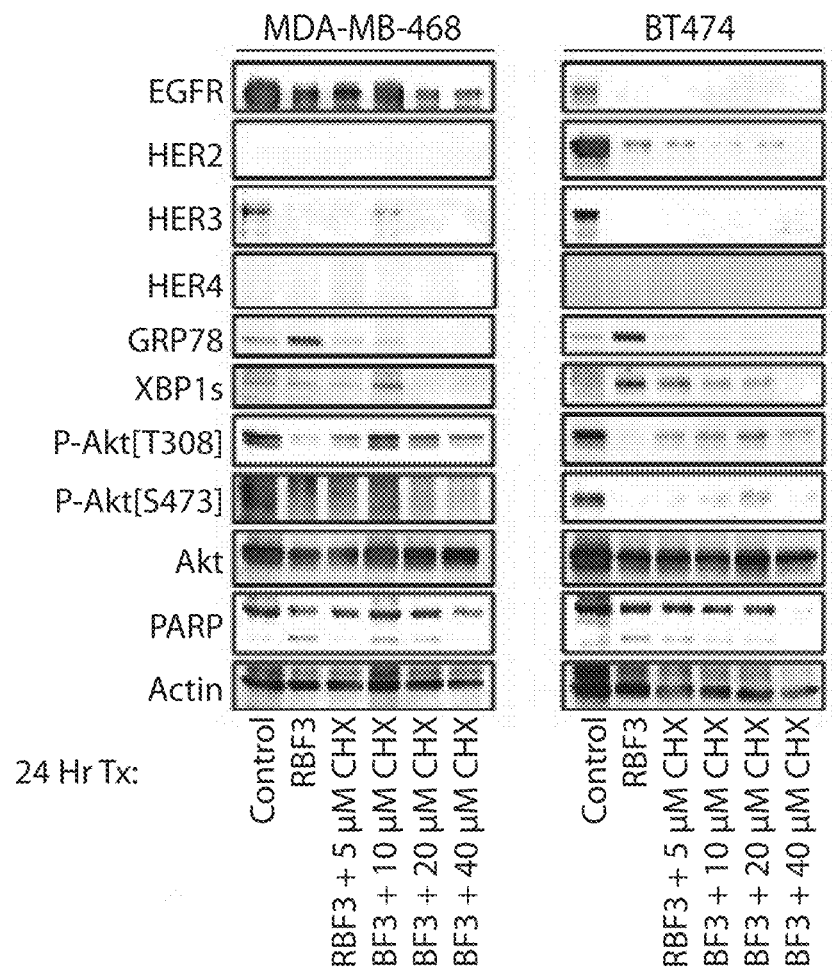

The sensitivity of HER2+ breast cancer cells to ERAD inhibition depends on continued protein synthesis [25]. The protein synthesis inhibitors cycloheximide (CHX) and puromycin function by interfering with the translocation step in protein synthesis and by inducing premature chain termination during translation, respectively. DDA activation of the ER stress response was reduced if protein synthesis was inhibited using either CHX or Puromycin over 8 hours (FIG. 2A). Inhibition of protein synthesis with CHX also partly overcame PARP cleavage and Akt dephosphorylation, suggesting that induction of ER stress may be partially responsible for these DDA responses. In contrast, CHX did not overcome DDA-mediated downregulation of EGFR or HER3. Similar results were obtained after a 24 hour treatment period (FIG. 2B), although CHX blockade of RBF3-induced PARP cleavage was less apparent, and CHX partially restored HER2 expression in BT474 cells. Results at shorter time points (2-16 hrs) showed that CHX rapidly and persistently blocked RBF3-mediated UPR (FIG. 2C). A range of CHX concentrations were tested for their ability to reverse DDA responses. The results indicated that a complicated relationship exists between RBF3 responses and inhibition of protein synthesis (FIG. 2D). A likely explanation for this result is that on the one hand UPR stress is associated with inhibition of protein synthesis through the PERK-eIF2a branch, and would suppress ER stress induced by misfolding of proteins such as HER1-3, while on the other hand, resolution of ER stress requires the synthesis of proteins including ATF4, CHOP, and GRP78. Overall, the results in FIG. 2A-2D indicate that blockade of protein synthesis with CHX suppresses several DDA responses in a time- and concentration-dependent manner.

EGFR or HER2 Overexpression Sensitizes Cancer Cells to DDA Actions—

Figure 2E:
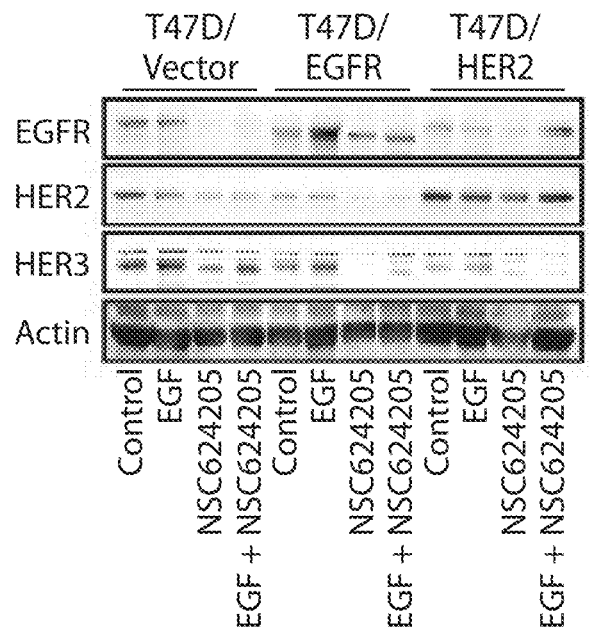
Figure 2F:
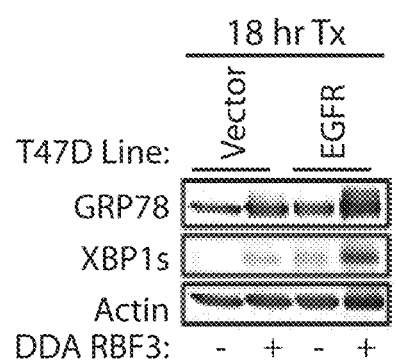
Figure 2G:
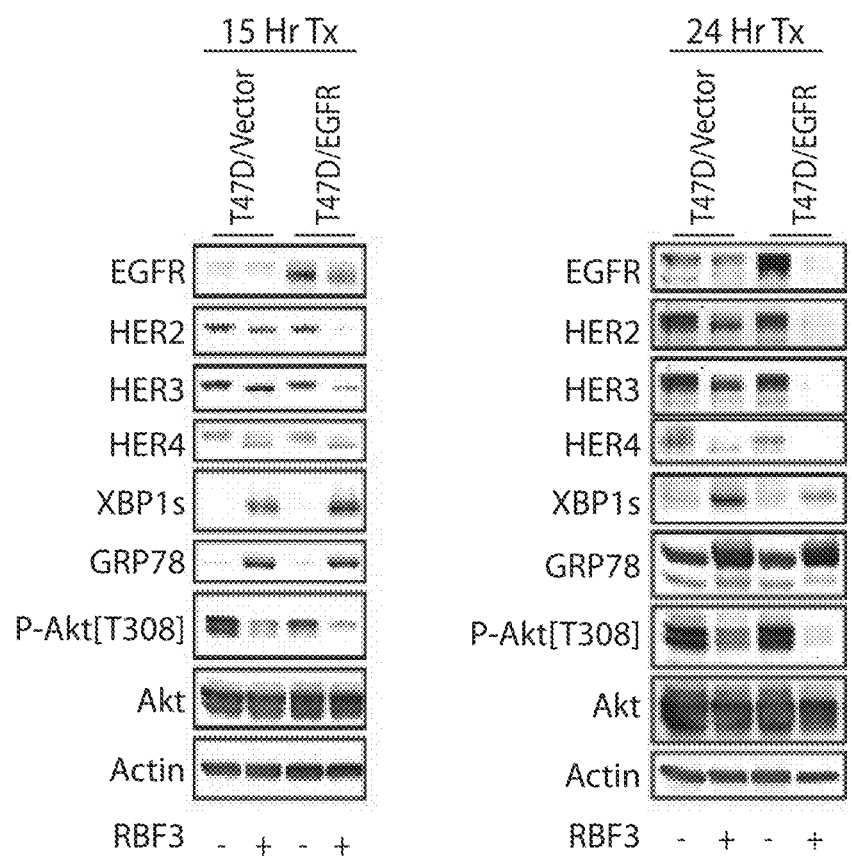

HER3 plays a major role in the survival of HER2+ breast cancers and their resistance to HER2-targeted drugs [20, 21]. It was previously shown that breast cancer cells engineered to overexpress EGFR are sensitized to DDA-induced cell death and Akt dephosphorylation [33], but differential sensitivity to DDA-mediated HER3 downregulation was not examined in that report. T47D cells engineered to overexpress EGFR or HER2 and treated with EGF, the DDA NSC624205, or EGF+NSC624205 showed that EGFR or HER2 overexpression decreased basal HER3 expression (FIG. 2E). This decreased baseline, combined with DDA treatment, reduced HER3 expression to very low levels. EGFR overexpression potentiated ER stress as measured by XBP1s and GRP78 expression at an intermediate (18 hr) time point (FIG. 2F). Analysis after 15 hours showed that RBF3 had largely downregulated HER2 and HER3 in the EGFR overexpressing cells at this time point, while the levels of these proteins was unchanged in the vector control cells (FIG. 2G). The ATF4 and XBP1s UPR markers were higher in the EGFR expressing line compared to the control, while RBF3 induced GRP78 to similar levels in both lines at 15 hours post treatment. Akt dephosphorylation was slightly enhanced in the context of EGFR overexpression at this time point. The differential effects of RBF3 on EGFR-overexpressing versus control cells on HER2, HER3, and phospho-Akt was amplified at 24 hours as compared with 15 and 18 hours. In contrast, at 24 hours after RBF3 treatment XBP1s levels were higher in the control cells than the EGFR overexpressing line. The ER stress response frequently peaks and then becomes weaker over time after ER chaperones have been upregulated, protein synthesis has been suppressed, and protein misfolding becomes resolved. Thus, the differences between time points likely results from the peak of the ER stress response occurring earlier in the EGFR overexpressing cells as compared with the control cells. HER4 was not expressed at detectable levels in the MDA-MB-468 or BT474 cell lines, but HER4 was expressed in the T47D line. RBF3 induced HER4 downregulation at the 24 hour time point, but not at the 15 hour time point.

DDA Effects on HER1-3 and Akt are Separable from Effects on the ER Stress Response—

Figure 3A:
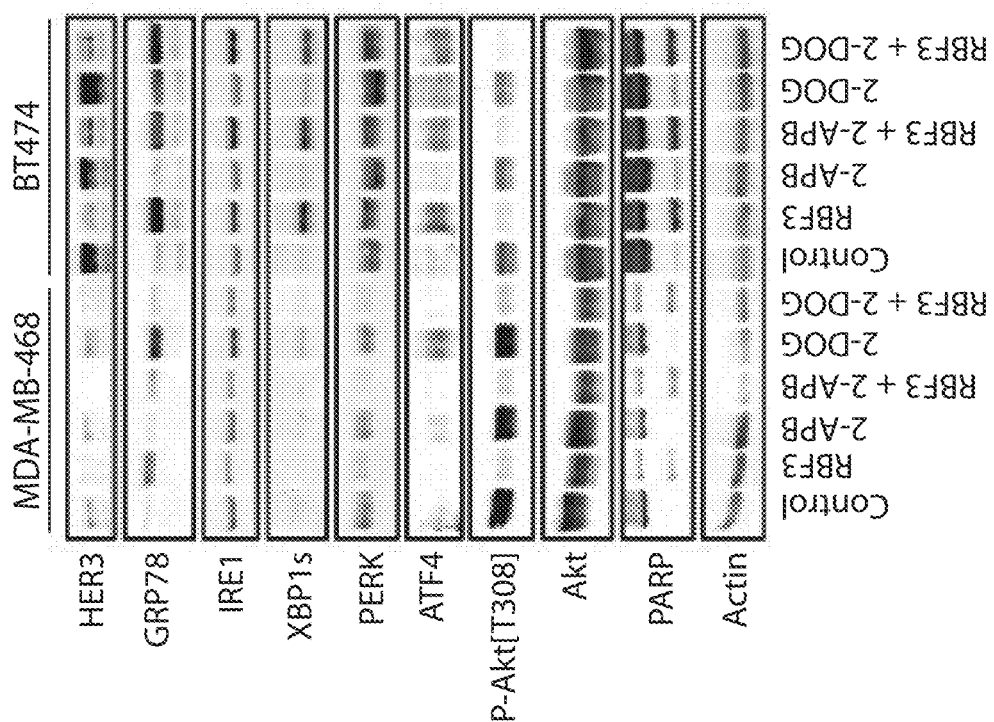
FIGS. 3A-3D. DDA Activation of UPR is separable from effects on HER 1-3 levels and Akt phosphorylation.
Figure 3B:
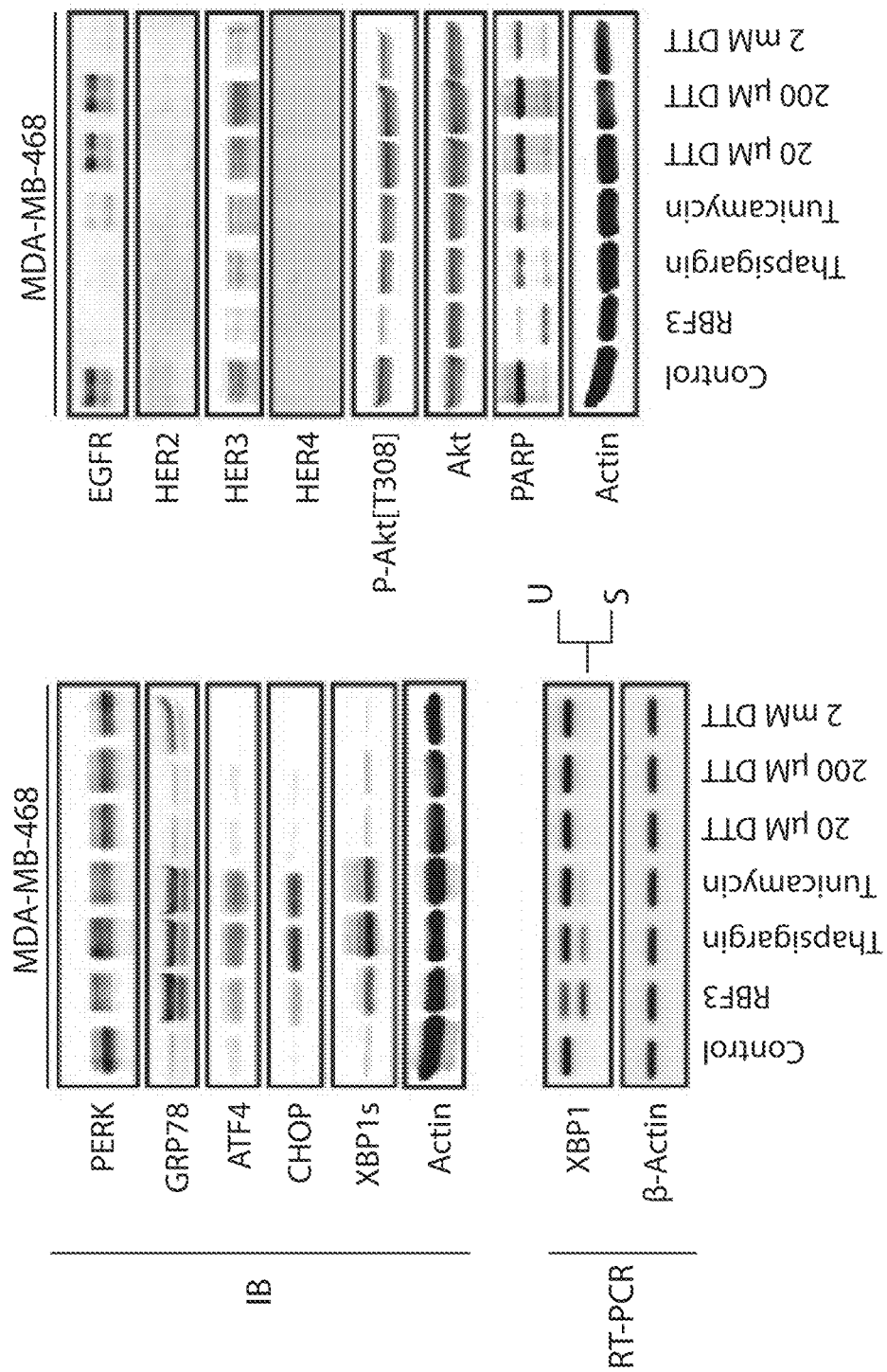

The DDA RBF3 was compared with 2-deoxyglucose (2-DOG), thapsigargin, tunicamycin, and dithiothreitol (DTT) to determine whether downregulation of HER-family receptors, decreased Akt phosphorylation, and induction of cell death is common among all ER stress inducers. 2-DOG strongly activated UPR in both the MDA-MB-468 and BT474 lines, but did not cause downregulation of either HER3 expression or Akt phosphorylation, and did not increase cell death as measured by PARP cleavage (FIG. 3A). Some ER stress responses result from increased cytoplasmic $Ca^{2+}$ mediated through IP3 receptors. To evaluate the role of this mechanism in RBF3 actions, we employed the $IP_3R$ antagonist 2-aminoethoxydiphenyl borate (2-APB). 2-APB reduced RBF3-mediated GRP78 upregulation, but did not alter RBF3-induced downregulation of HER3, Akt dephosphorylation, or PARP cleavage. Comparison of RBF3 with thapsigargin, tunicamycin, or DTT treatment of MDA-MB-468 cells revealed that RBF3 most effectively upregulated GRP78 expression and IRE1-dependent XBP1 mRNA processing, while thapsigargin and tunicamycin elevated ATF4 and CHOP expression more effectively than RBF3 (FIG. 3B). In this cell line, 2 mM DTT only weakly activated the ER stress response as measured by GRP78 upregulation. EGFR was downregulated by all of the ER stressors. HER3 levels were particularly sensitive to 20 μM RBF3 and less so to 2 mM DTT. Of all of the ER stress inducers, only RBF3 induced significant PARP cleavage, and RBF3 most strongly downregulated Akt phosphorylation.

Figure 3C:
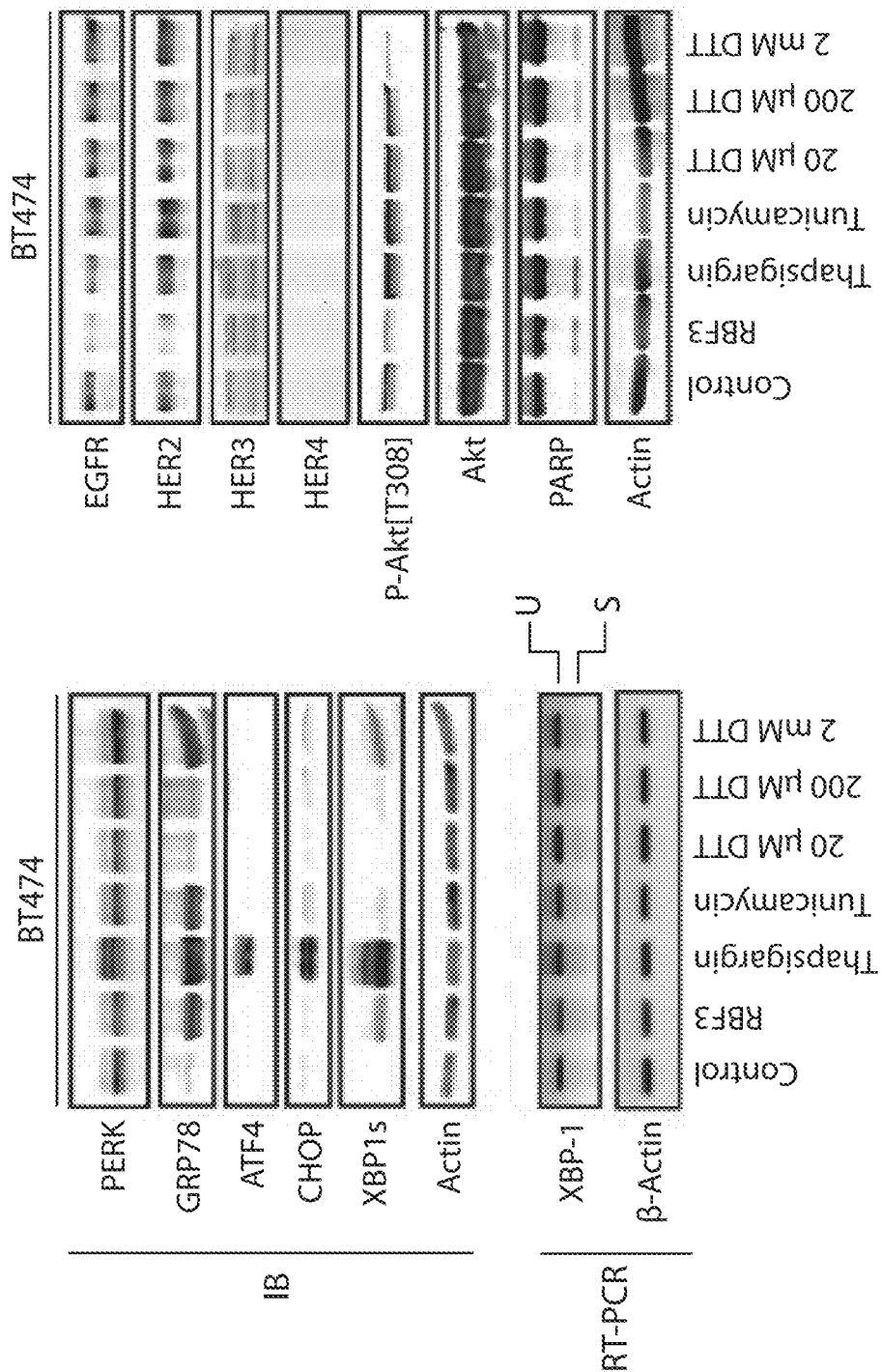

Although BT474 cells responded somewhat differently to the ER stressors than the MDA-MB-468 cells, RBF3 and DTT increased XBP1s and GRP78 expression with little upregulation of ATF4 or CHOP expression (FIG. 3C). This is in contrast to thapsigargin treatment, which strongly upregulated both ATF4 and CHOP, and more strongly decreased PERK electrophoretic mobility, consistent with its increased phosphorylation [37]. Under these conditions, only RBF3 strongly downregulated EGFR and HER2 expression, while both RBF3 and DTT, but none of the other ER stressors, decreased Akt phosphorylation. Taken together, the results in FIGS. 3A-3C demonstrate that RBF3 produces a pattern of ER stress response that is different from that observed with 2-DOG, thapsigargin, and tunicamycin. RBF3 responses were most similar to those seen with DTT, although DTT was applied to the cells at a 100 times higher concentration than RBF3. RBF3 and DTT decrease Akt phosphorylation in both cell lines. RBF3 reduces HER-family receptor expression in both cell lines, while DTT only does so in the MDA-MB-468 line. Thus, the DDA RBF3 is unique when compared to ER stressors 2-DOG, thapsigargin, tunicamycin, and DTT with respect to the spectrum of ER stress responses, Akt dephosphorylation, HER-family receptor downregulation, and cell death induction.

Figure 3D:
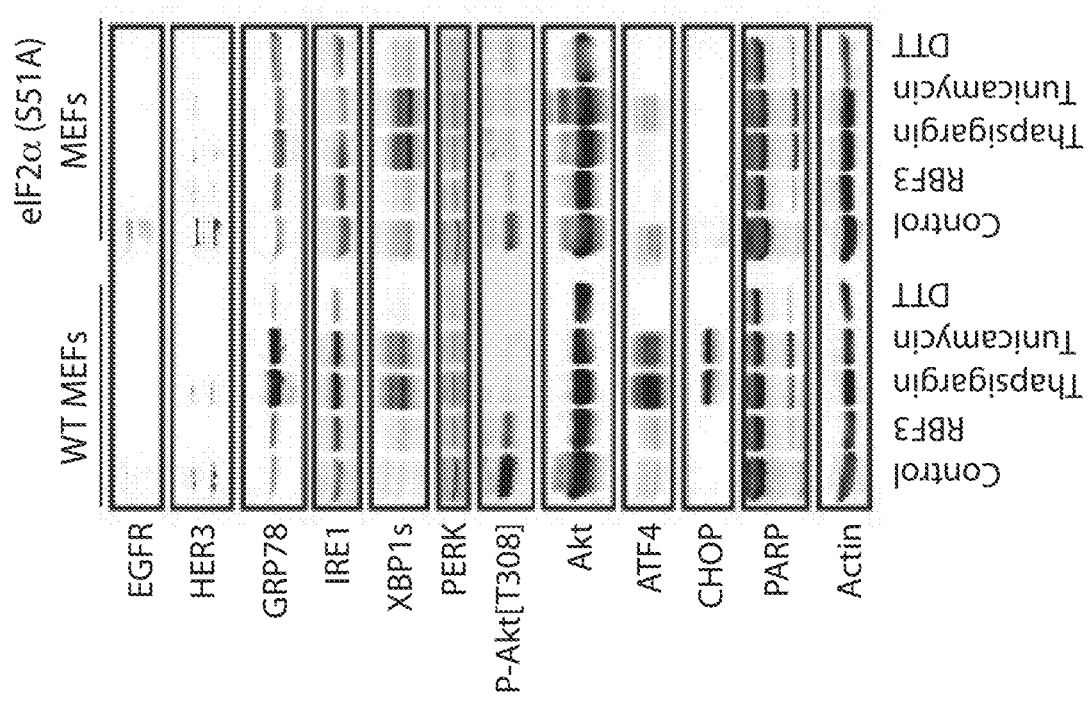

In contrast to the robust effects of RBF3 on the EGFR$^+$ or HER2$^+$ breast cancer cell lines, RBF3 and DTT did not induce an ER stress response in wild type Mouse Embryo Fibroblasts (MEFs) and weakly suppressed Akt phosphorylation and induced PARP cleavage (FIG. 3D). However, thapsigargin and tunicamycin induced a robust UPR, markedly suppressed Akt phosphorylation, and strongly upregulated PARP cleavage. In MEFs in which eIF2a with the PERK phosphorylation site Ser51 mutated to Ala was heterozygously knocked in [38], CHOP, ATF4, and GRP78 upregulation by thapsigargin and tunicamycin was significantly blunted. However, the S51A eIF2a mutation did not affect thapsigargin- or tunicamycin-induced PARP cleavage or XBP1s upregulation. MEFs express very low levels of the HER-family receptors and this may contribute to their relative resistance to thiol-reactive agents such as RBF3 and DTT.

Cooperation Between DDAs and Receptor Tyrosine Kinase Inhibitors—

Since DDAs and receptor tyrosine kinase (RTK) inhibitors such as EGFR-specific Gefitinib and EGFR/HER2-specific Lapatinib block the functions of EGFR and HER2 through distinct mechanisms, we examined whether these two classes of agents cooperate to inactivate mitogenic signaling pathways and activate UPR. Co-treatment with either 2.5 µM Gefitinib or Lapatinib lowered the concentration of RBF3 required to downregulate HER3 levels and Akt phosphorylation (FIG. 4A). Under these conditions, the combination treatments did not alter UPR as measured by GRP78, XBP1s, or ATF4 expression, but Gefitinib, and to a lesser extent Lapatinib, cooperated with RBF3 to upregulate CHOP expression.

Figure 11A:
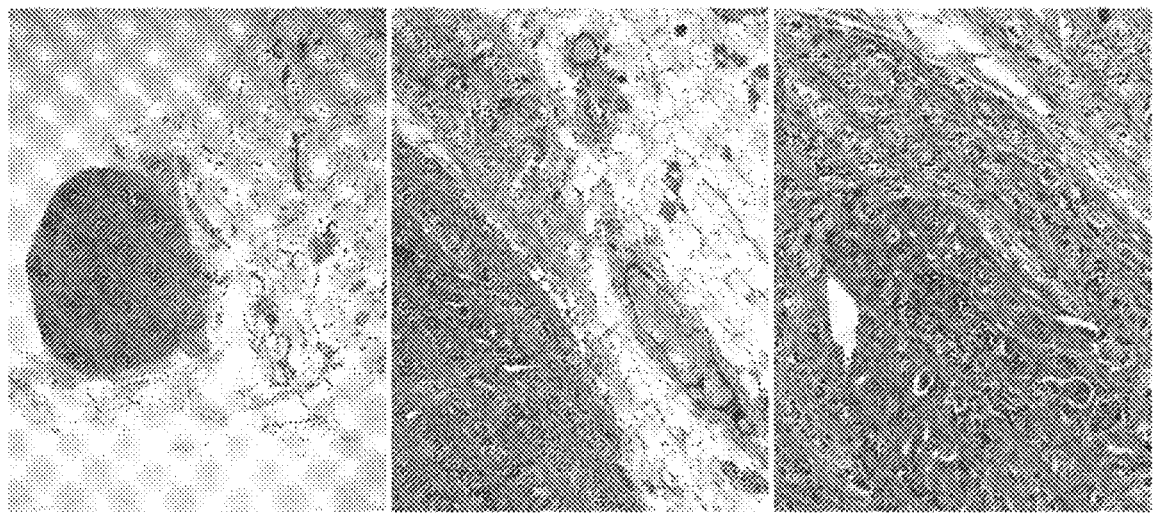
FIGS. 11A-11B. Characterization of the HCI-012 PDX-derived cell line.

The MDA-MB-468 and BT474 cell lines are well characterized models for EGFR and HER2 overexpressing breast cancer, but form highly homogenous tumors with questionable relevance to human breast cancer. Patient-Derived Xenograft (PDX) models are the system of choice for studying the effectiveness of anticancer agents against human breast cancers (reviewed in [39]), but the cellular heterogeneity responsible for their higher clinical relevance renders studies of the mechanisms of drug action on cancer cells difficult. To bridge this gap, we isolated a cell line from the previously described HCI-012 HER2$^+$ and ER−, PR− PDX line [40] using Conditional Cell Reprogramming (CCR) [41, 42]. The HCI-012 cell line formed tumors when injected into the mammary fat pads of immunocompromised NOD-SCID-γ (NSG) mice at 100% efficiency (n=5/5), and the heterogeneous morphology of the resulting tumors was similar to that of the parental xenograft line (FIG. 11A). The HCI-012 cells rapidly initiate cell death if not cultured in the CCR medium (FIG. 11B), consistent with previous reports that the CCR approach maintains reversible immortality of epithelia-derived cell lines in vitro [42]. RBF3 treatment of HCI-012 cells induced cell death (FIG. 4B), which was associated with upregulation of ER stress markers, reduced Akt phosphorylation, but RBF3 had no effect on Erk phosphorylation (FIG. 4C). Lapatinib partially reduced Akt phosphorylation, and strongly suppressed ERK phosphorylation, but did not alter EGFR, HER2, or HER3 levels, nor did it alter the expression of ER stress markers. The combination of RBF3 and Lapatinib suppressed EGFR and HER2 expression and completely abrogated both Akt and Erk phosphorylation. This result suggests that these two agents are complementary in their effects on mitogenic/survival signaling. In the HCI-012 cells, Lapatinib did not influence RBF3 upregulation of the ER stress markers GRP78, ATF4, XBP1s, or CHOP.

DDA Impacts Pathways that Mediate Resistance to HER2- and mTORC1-Targeted Therapeutics—

Figure 4D:
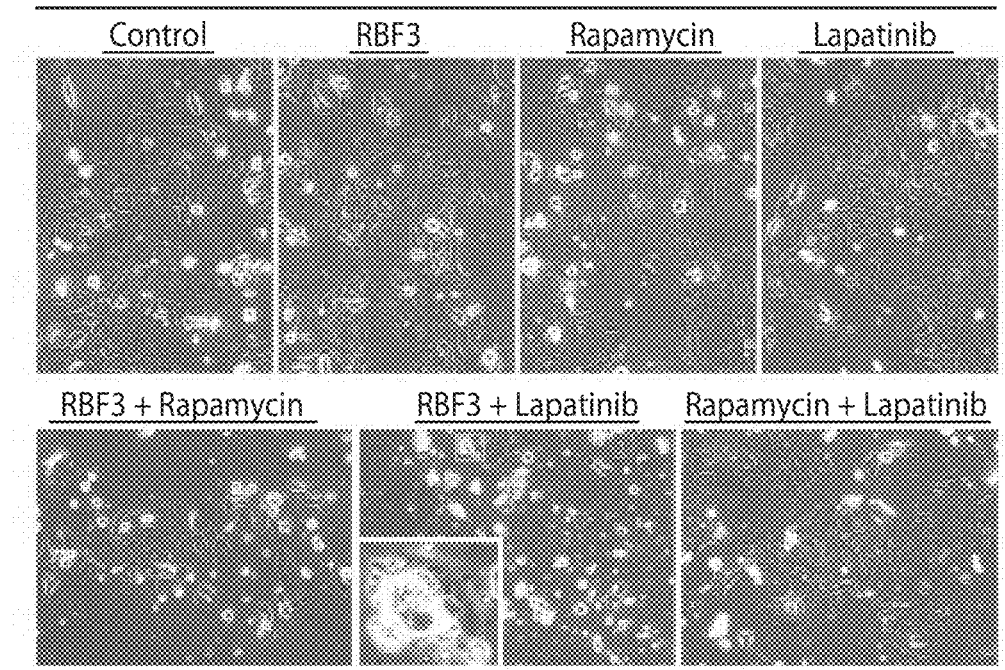
Figure 4E:
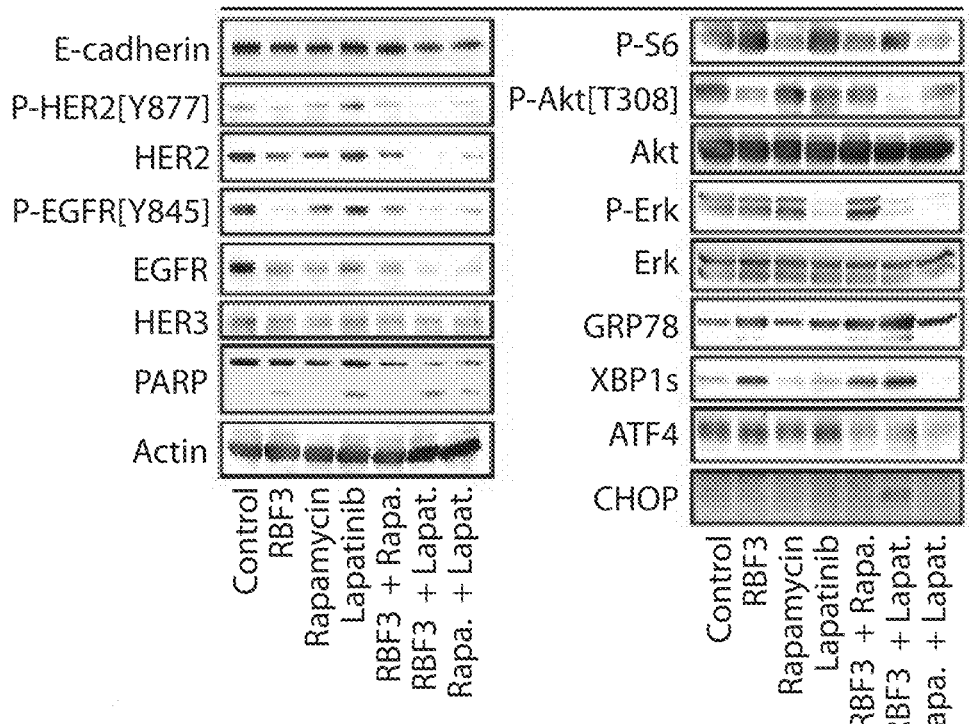
Figure 4F:
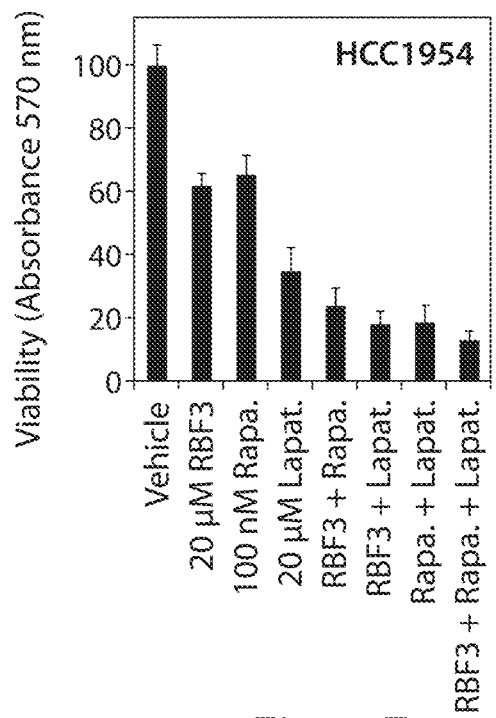

The HCC1954 cell line is a model of Trastuzumab resistant, HER2-positive breast cancer, and resistance is thought to be mediated by the activating Phosphatidylinositol 3-kinase (PI3K) mutation H1047R [43]. Observation of cultures revealed that combining RBF3 and Lapatinib resulted in the highest level of cell death (FIG. 4D). Under these conditions, RBF3 and Lapatinib cooperated to downregulate EGFR and HER2, to increase fractional PARP cleavage, and to suppress Akt phosphorylation (FIG. 4E). The mTORC1 inhibitor rapamycin did not cooperate with RBF3 to produce these effects and antagonized RBF3-mediated Akt dephosphorylation. Lapatinib only weakly potentiated RBF3-induced UPR with respect to GRP78, XBP1s, or ATF4 levels, but cooperated with RBF3 to upregulate CHOP expression. RBF3+Lapatinib was more effective in reducing HCC1954 cell viability than either of the compounds applied individually (FIG. 4F).

Figure 4G:
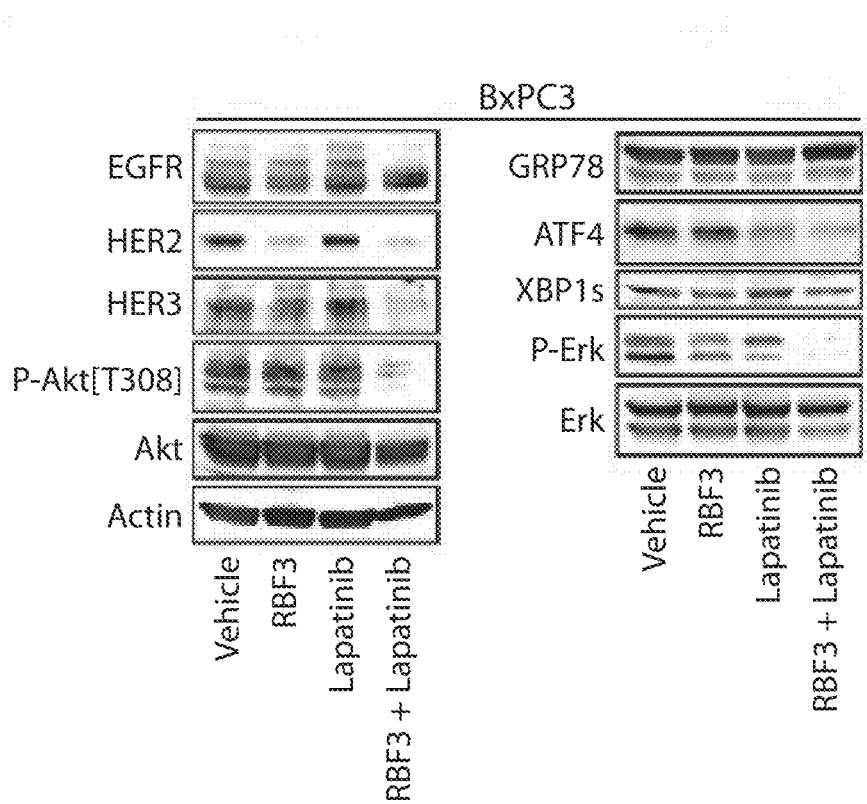
Figure 4H:
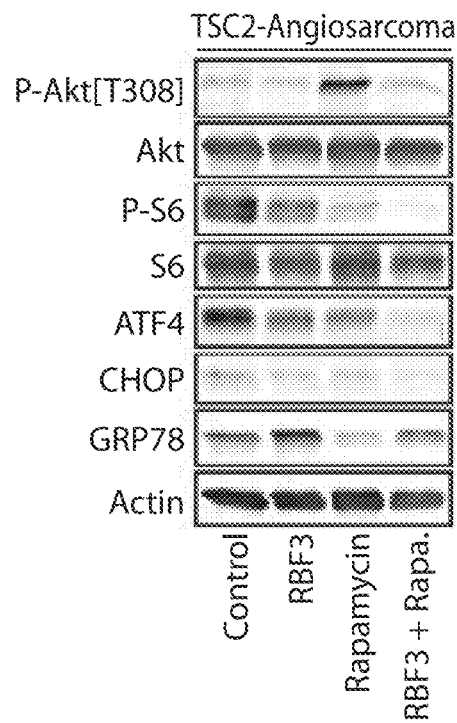
Figure 4I:
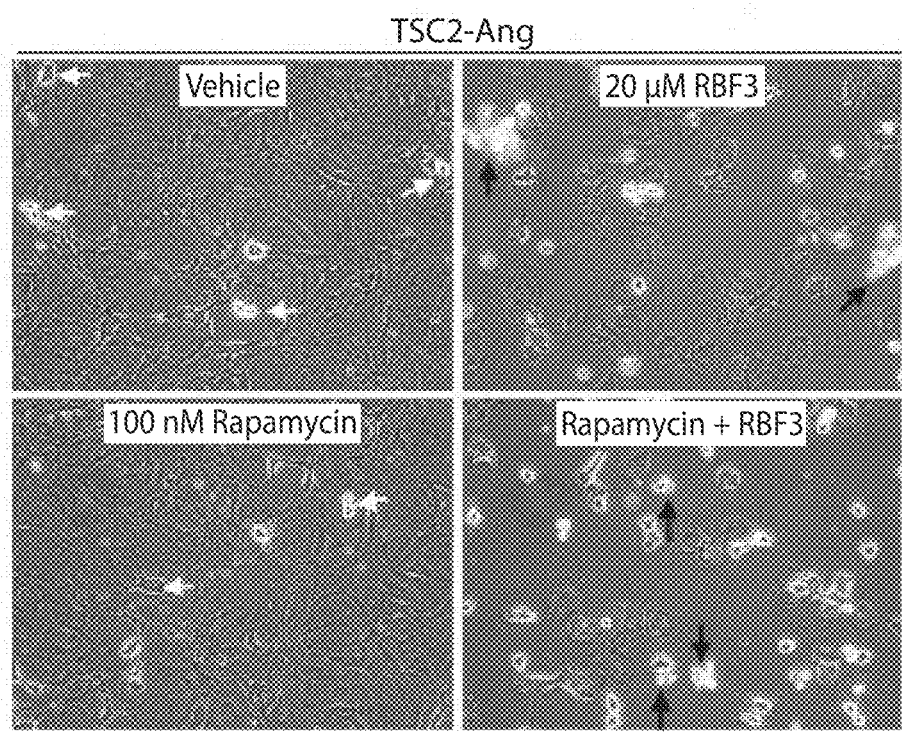

Previous studies demonstrated that in contrast to EGFR or HER2 overexpressing breast cancer lines, the BxPC3 pancreatic cancer cell line is refractory to DDAs [33]. Challenging BxPC3 cells with RBF3 indicated that it reduced HER2 expression, but had little effect on the levels or phosphorylation states of the other proteins examined (FIG. 4G). Lapatinib had no significant effect on HER1-3 expression, or Akt or Erk phosphorylation. However, RBF3+Lapatinib not only downregulated HER2, but also strongly downregulated HER3, and suppressed both Akt and Erk phosphorylation.

mTORC1 inhibitors such as the rapamycin analogs (rapalogs) inadvertently activate the PI3K/Akt axis by removing negative feedback mediated through S6K1 [44, 45]. Since Akt activation might detract from the clinical utility of rapalogs, which are used in immunosuppression, the treatment of human cancers, and the management of Tuberous Sclerosis (TSC) (Reviewed in [46]), the reversal of rapamycin-mediated Akt activation by RBF3 was examined. In TSC, individuals have mutations in the genes coding for the proteins TSC1 or TSC2 and develop benign tumors in multiple tissues in part because the TSC1/TSC2 complex is a GTPase activating protein for the Rheb GTPase responsible for mTORC1 activation (reviewed in [47]). Thus, mTORC1 activation is characteristic of TSC. Rapalogs are FDA-approved for TSC treatment, but activation of Akt could be a significant side effect. To address this point, angiosarcoma cells from a TSC2 knockout mouse (TSC2-Ang1; ATCC CRL-2620) were used as a model system. Treatment of these cells with RBF3 had little effect on ER stress markers, which were high under control conditions (FIG. 4H). Rapamycin strongly increased Akt phosphorylation and co-administration of RBF3 reduced Akt phosphorylation to basal levels. TSC2-Ang1 cell death was only observed upon treatment with RBF3 or RBF3+Rapamycin (black arrows), whereas vehicle and rapamycin treated cells continued to proliferate (white arrows) (FIG. 4I). The combination of RBF3 and rapamycin more effectively suppressed S6 phosphorylation than rapamycin alone. The results in FIG. 4 suggest that DDA combinations with RTK inhibitors might provide improved anticancer actions. Pairing DDAs with rapalogs may both increase mTORC1 inhibition and prevent off-target Akt activation.

Preparation and Characterization of Multivalent DDAs—

Figure 5A:
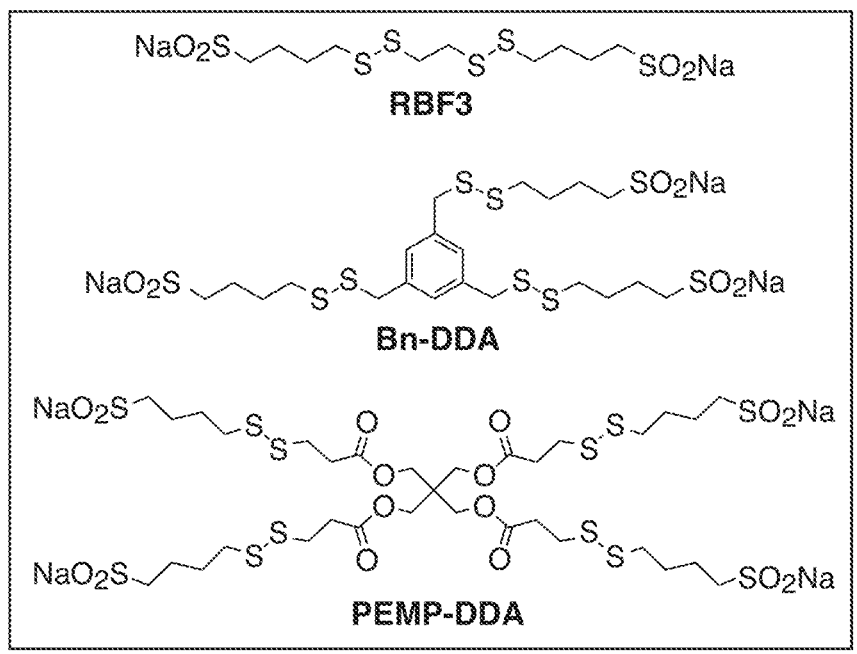
FIGS. 5A-5I. Increasing the number of pharmacophores per DDA molecule improves potency against MDA-MB-468 cells.
Figure 5B:
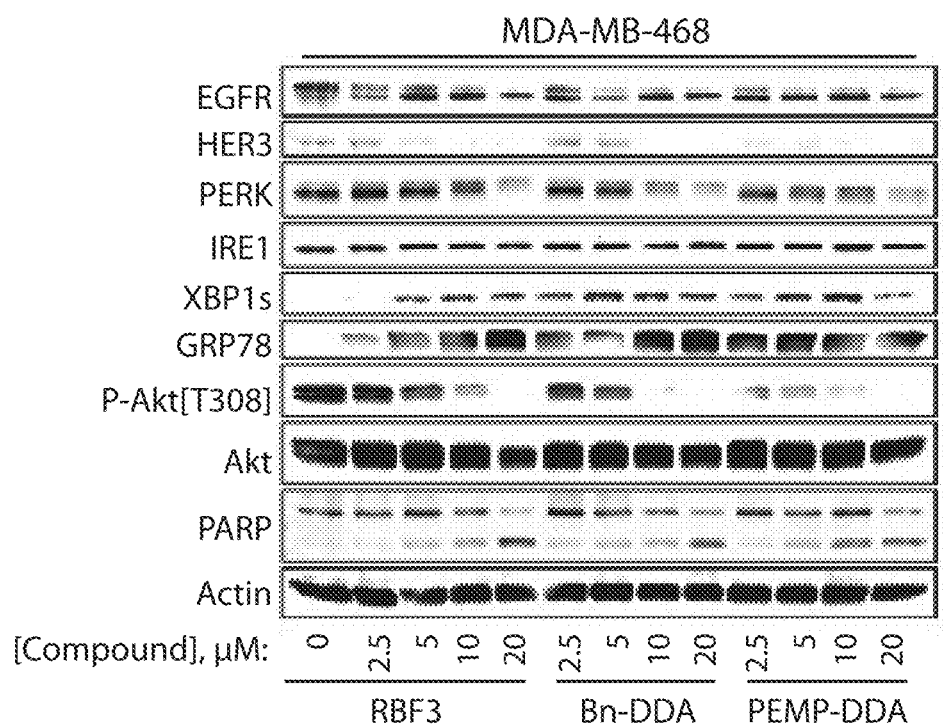
Figure 5C:
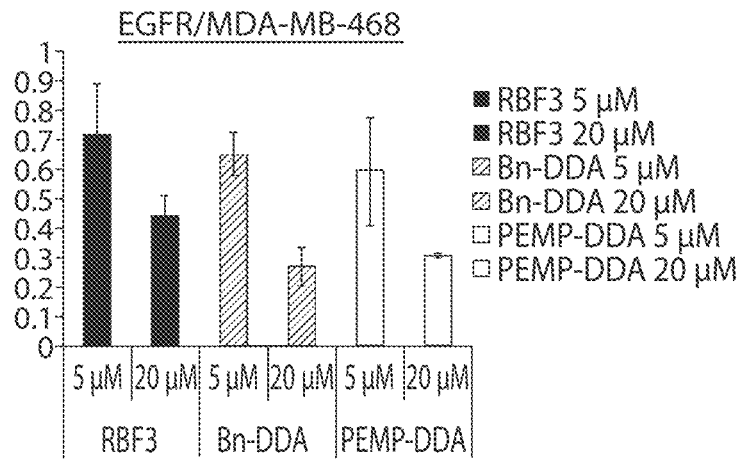
Figure 5D:
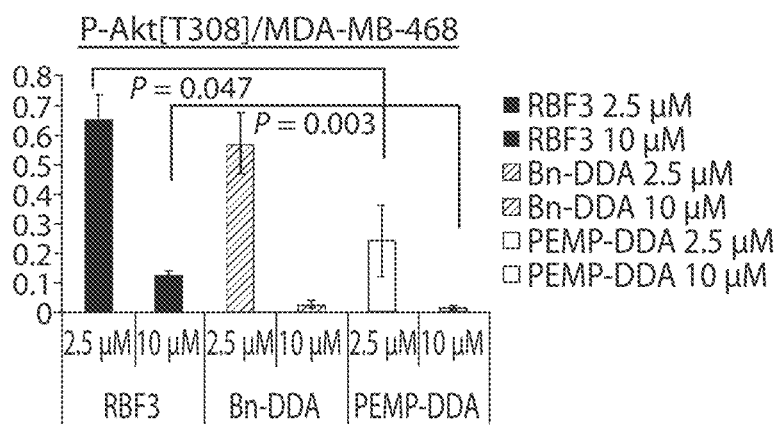
Figure 5E:
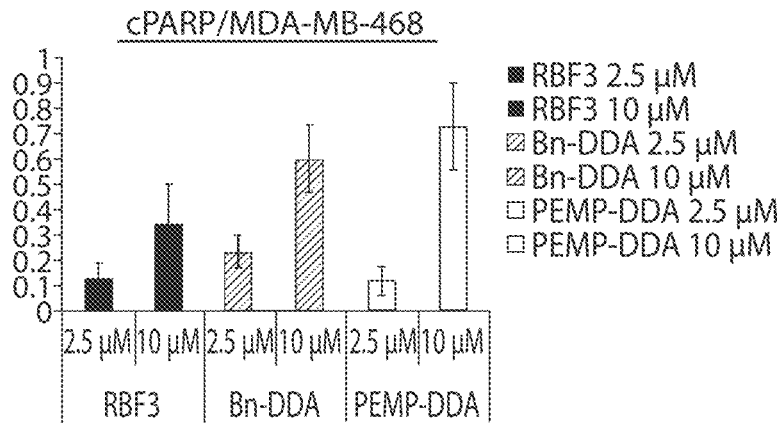
Figure 5F:
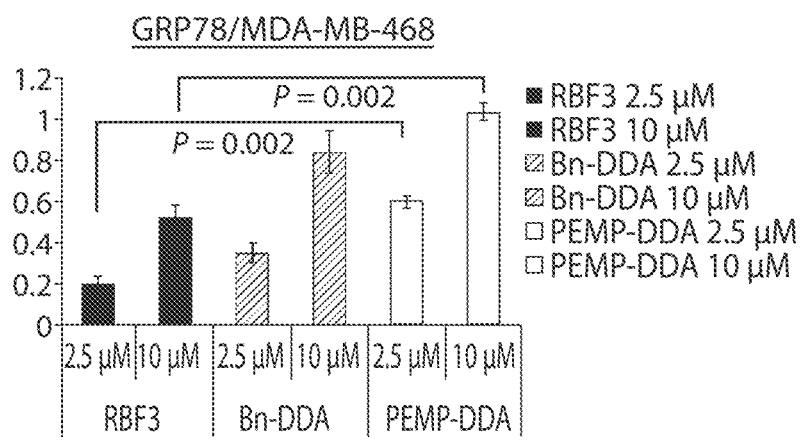
Figure 5G:
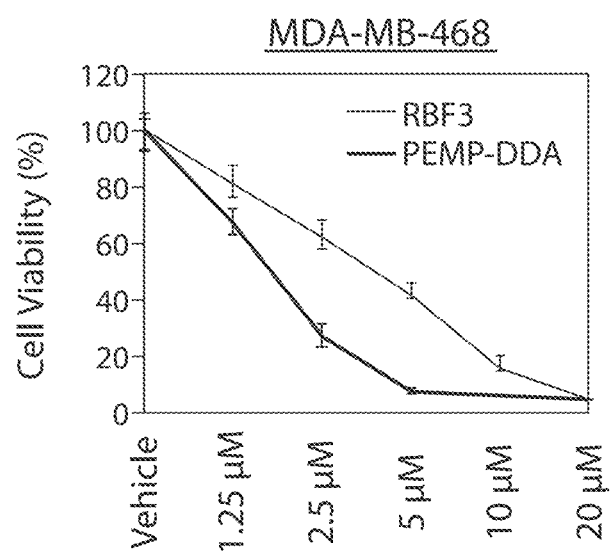

DDA RBF3 contains two repeats of the previously defined pharmacophore [33]. New DDAs, termed Bn-DDA and PEMP-DDA, containing three and four copies of the pharmacophore per molecule, respectively, were synthesized to determine whether they have increased potency over RBF3 (FIG. 5A). Treatment of the DDA sensitive EGFR+ MDA-MB-468 cell line with increasing concentration of each compound indicated that PEMP-DDA decreased Akt phosphorylation and HER3 levels more than RBF3 or Bn-DDA (FIG. 5B). This immunoblot analysis was repeated a total of three times and DDA-induced changes in EGFR, phospho-Akt[Thr308], PARP cleavage (cPARP), and GRP78 levels were plotted in FIGS. 5C, 5D, 5E, and 5F, respectively. The replicate immunoblot analyses are shown in FIGS. 9A-9D. Statistically significant differences are indicated with P-values obtained using Student's unpaired t-test. All bands were normalized to the corresponding Actin loading control before the ratios between drug treatments were calculated. MTT assays with increasing concentrations of RBF3 and PEMP-DDA showed that both reduced cell viability in a concentration-dependent manner (FIG. 5G).

Figure 5H:
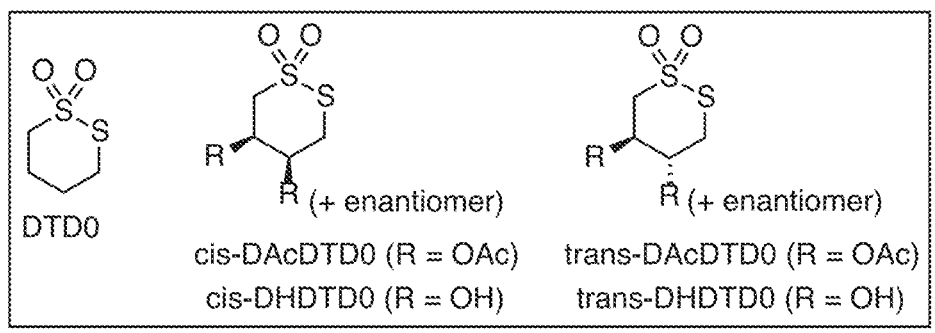
Figure 5I:
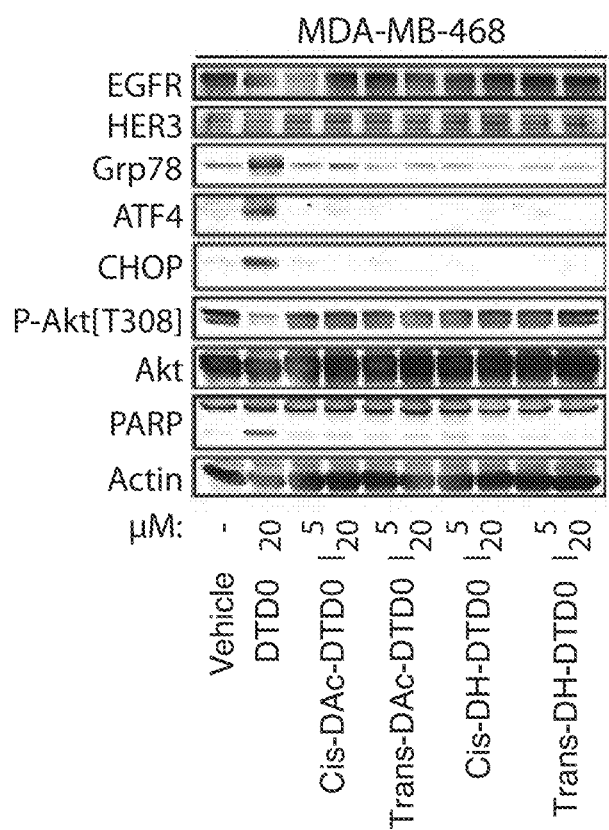
Figure 6A:
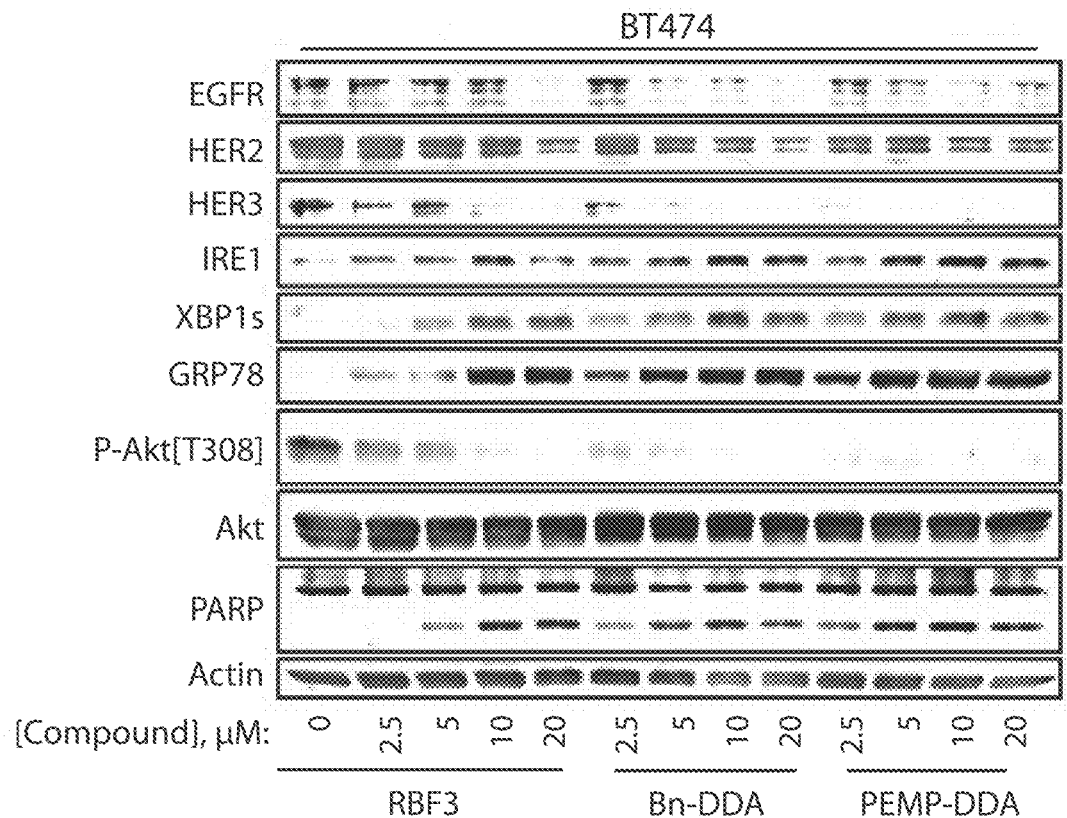
FIGS. 6A-6D. Increasing the number of pharmacophores per DDA molecule improves potency against BT474 cells.
Figure 6B:
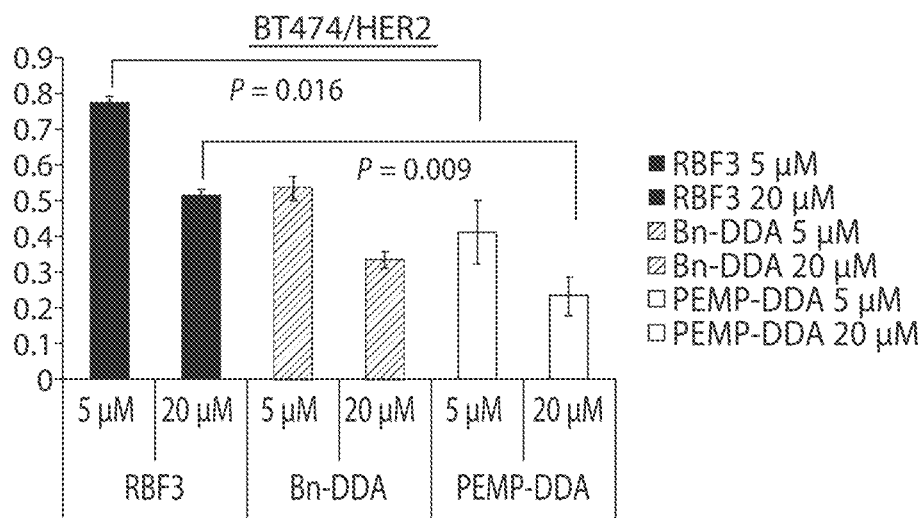
Figure 6C:
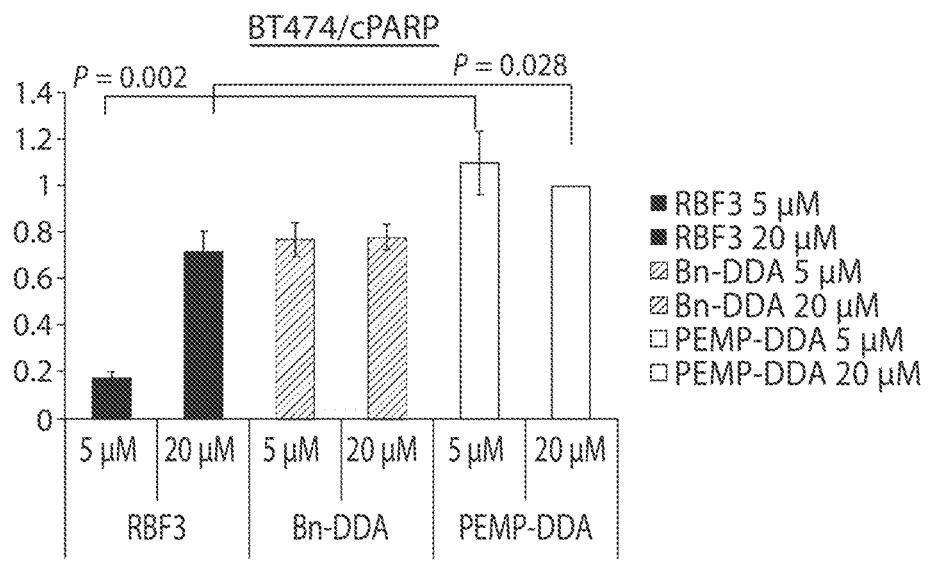
Figure 6D:
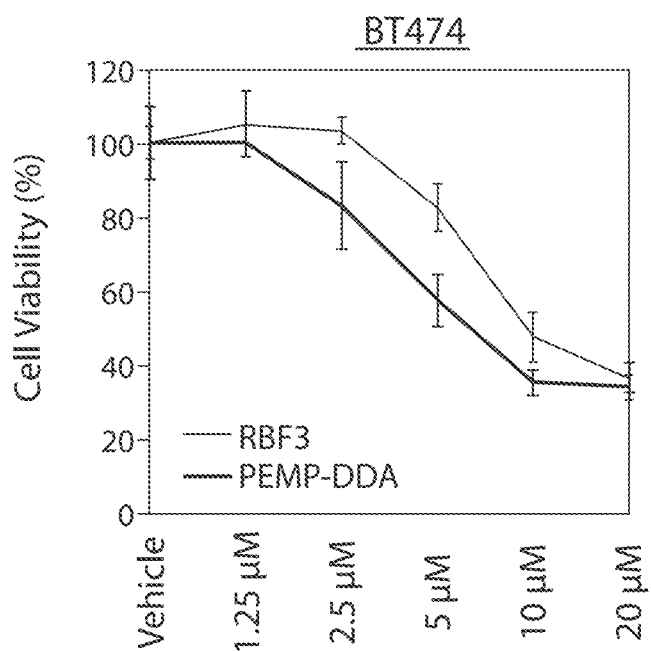

DTDO is a cyclic form of the previously identified DDA pharmacophore [33]. Since the two sulfur atoms of DTDO are involved in DDA chemistry, we examined whether derivatization of the second and third carbon atoms of the four-carbon linker by either hydroxyl or acetyl groups (FIG. 5H) altered DDA actions on cells. DTDO (20 µM) reduced activating Akt phosphorylation, upregulated markers of ER stress, and increased PARP cleavage (FIG. 5I). In contrast, the hydroxylated or acetylated DTDO derivatives with either cis or trans configurations had little or no effect on these endpoints at 20 µM. This result suggests that the cyclic DDAs act through similar mechanisms as the linear forms (e.g., RBF3).

Experiments similar to those carried out with MDA-MB-468 cells in FIG. 5 were carried out with the HER2+, DDA-sensitive BT474 cell line in FIG. 6. All three DDAs decreased EGFR, HER2, and HER3 expression, increased PARP cleavage, reduced Akt phosphorylation and upregulated the ER stress markers GRP78 and XBP1s (FIG. 6A). PEMP reduced HER2 expression (FIG. 6B) and PARP cleavage (FIG. 6C) significantly more than RBF3 at the same drug concentrations. PEMP-DDA also reduced BT474 cell viability more than RBF3 (FIG. 6D).

Figure 10A:
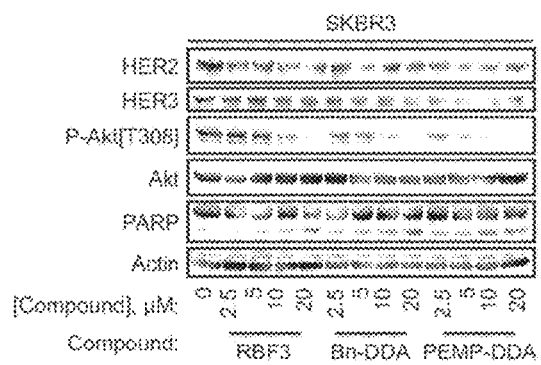
FIGS. 10A-10C. SKBR3 (FIG. 10A), HCC1954 (FIG. 10C), and MDA-MB-231 (FIG. 10B) immunoblot panels.
Figure 10B:
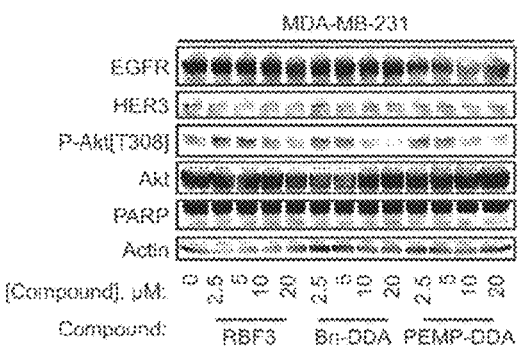
Figure 10C:
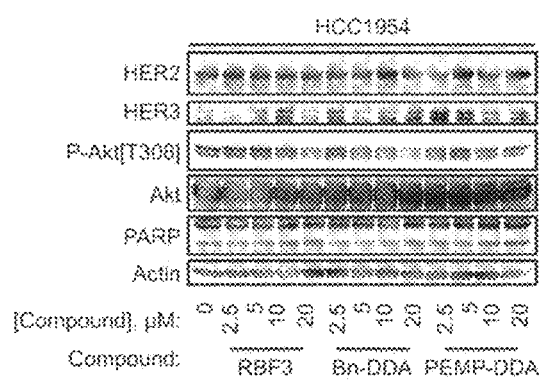

The DDA responsive, HER2+ SKBR3 cell line produced similar responses to bi-, tri-, and tetra-functional DDAs as observed with the MDA-MB-468 and BT474 lines (FIG. 10A). As expected, the DDA-resistant MDA-MB-231 and HCC1954 exhibited ER stress in control samples and did not exhibit a response to any of the DDAs (FIGS. 10B and 10C, respectively).

DDAs are not Toxic to Cardiomyocytes or MCF10/DCIS Cells—

Figure 7A:
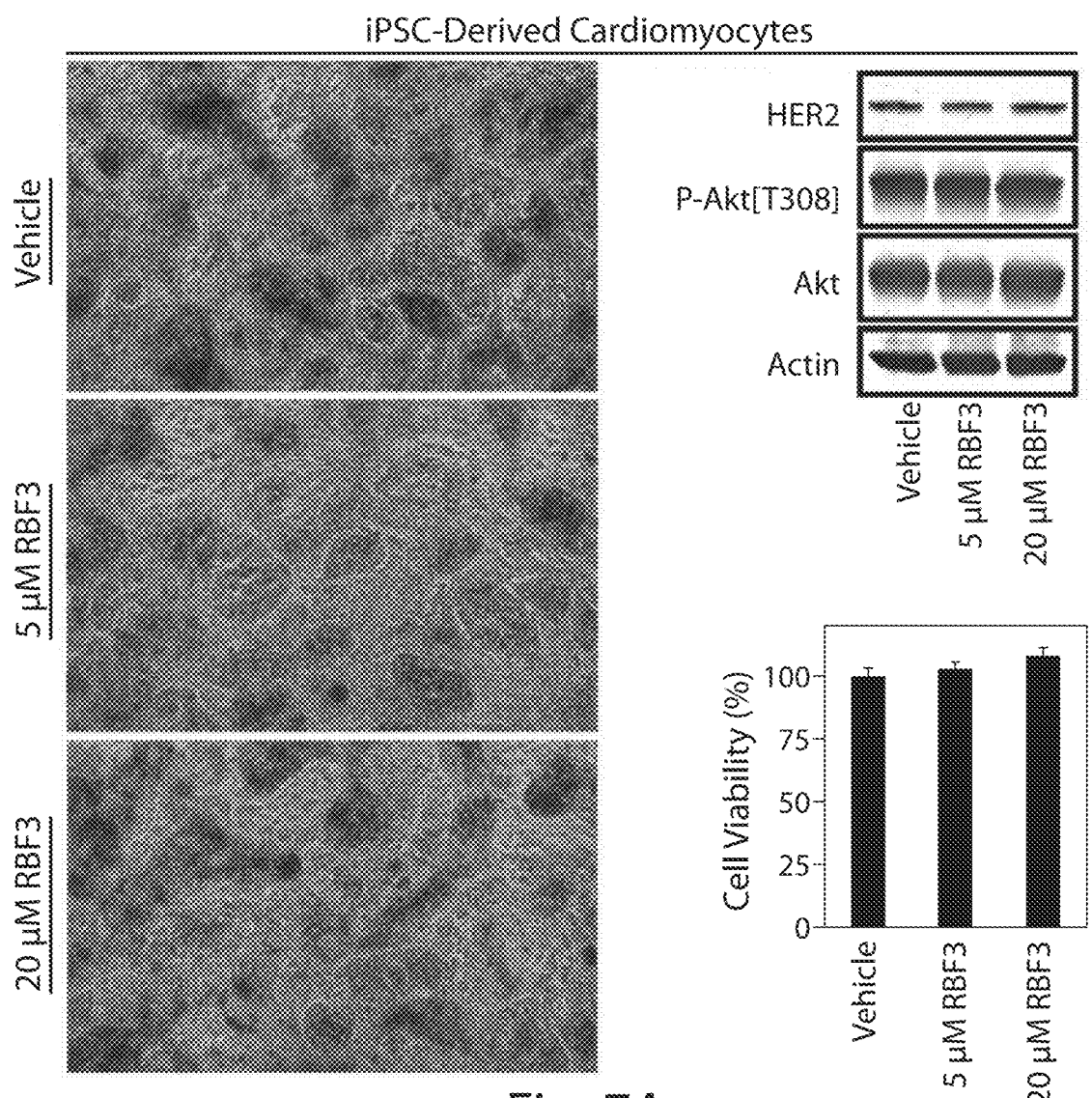
FIGS. 7A-7B. DDAs are not toxic to cardiomyocytes or MCF10/DCIS cells.

Cardiotoxicity is a side effect of the HER2 specific monoclonal antibody Trastuzumab. Therefore we examined whether RBF3 altered the behavior of cardiomyocytes differentiated from human induced Pluripotent Stem Cells (iPSCs) as described previously [48, 49]. Microscopic examination of cardiomyocytes treated for 24 hours with RBF3 did not change appearance (FIG. 7A, left panel) and their rate of beating was not altered. Immunoblot analysis demonstrated that the cardiomyocytes expressed HER2, but RBF3 treatment did not decrease the levels or HER2 or suppress Akt phosphorylation (FIG. 7A, upper right panel). MTT assays showed that RBF3 did not reduce the viability of cardiomyocytes (FIG. 7A, lower right panel).

Figure 7B:
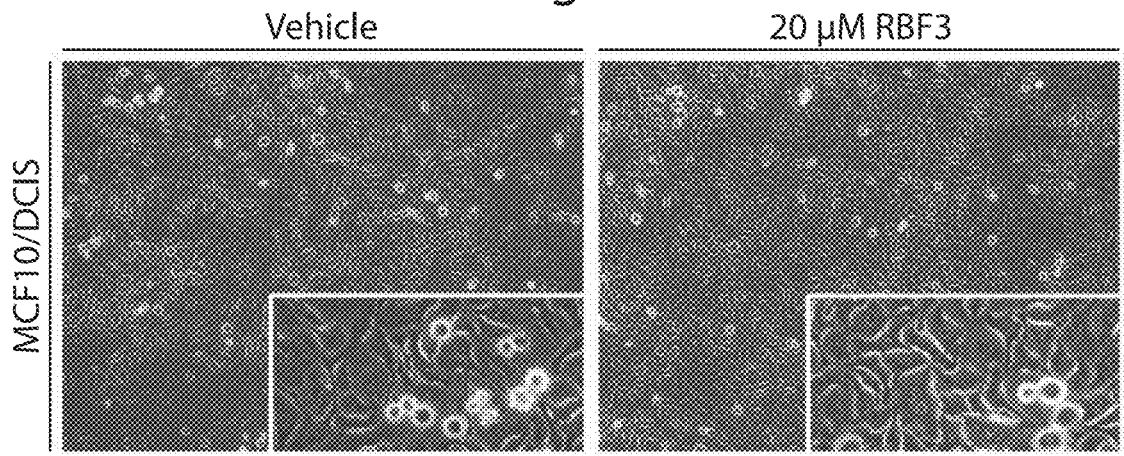

The MCF10/DCIS cell line serves a model of Ductal Carcinoma in situ in which cancer cells aberrantly proliferate, but are unable to invade through the basement membrane to invade locally. MCF10/DCIS cells are considered to express normal levels of EGFR and HER2 [50]. MCF10/DCIS cells treated for 24 hours with 20 µM RBF3 did not die but continued to proliferate (FIG. 7B).

Previous work showed that cancer cell death caused by DDAs correlates with HER1-3 downregulation and Akt dephosphorylation [33]. The results presented here extend these findings by showing that DDAs also activate UPR. We previously demonstrated the ability of DDAs to break disulfide bonds in the model compound oxidized Glutathione (GSSG) [33]. Disulfide bond formation is a critical component of the folding of both integral membrane and secreted proteins, and interference with this process by treatment with reducing agents such as dithiothreitol (DTT) activates UPR [51, 52]. The results in FIG. 1 demonstrate that DDAs activate all three branches of the ER stress response. Interestingly, DDA RBF3 activates UPR at low micromolar concentrations, while millimolar concentrations of DDT are required to induce a similar level of ER stress. It is tempting to speculate that this striking difference in potency relates to the structural uniqueness of DDAs in having a nucleophilic sulfinate group, an electrophilic disulfide group, and the ability of the pharmacophore to interconvert between cyclic and linear forms. Alternately, the bifunctional nature of DDAs may render them more difficult for cells to neutralize than DTT or similar reducing agents.

The observation that DDAs act through mechanisms involving UPR, Akt inactivation, and HER1-3 downregulation raises the question of which of these pathways contributes to DDA anticancer actions, and whether these responses are mechanistically related. A comparison of RBF3 with other ER stress inducers and the use of CHX to block protein synthesis and ER stress provide some insight into these issues. Thapsigargin upregulates ATF4, XBP1s, and CHOP expression more strongly than RBF3 in MDA-MB-468 cells, while RBF3 more effectively suppresses Akt phosphorylation than either tunicamycin or thapsigargin (FIG. 1D). Like 20 µM RBF3, 2 mM DTT induces downregulation of EGFR and HER3 and suppresses Akt phosphorylation, but under these conditions only weakly induces PARP cleavage and GRP78 expression, and does not upregulate ATF4, CHOP, or XBP1s protein expression or XBP1 mRNA splicing (FIG. 3B). Interestingly, 2-DOG strongly induces ER stress in MDA-MB-468 and BT474 cells as measured by upregulation of GRP78 and ATF4, but does not induce PARP cleavage, or suppress Akt phosphorylation (FIG. 3A). Further, 2-DOG does not suppress HER3 expression in either the MDA-MB-468 or BT474 cell lines. This suggests that reduction of HER1-3 receptor expression, suppression of Akt phosphorylation, and increased PARP cleavage relate to the thiol reactivity of RBF3 and DTT rather than to induction of UPR alone. However, results obtained with protein synthesis inhibitors show that while blockade of translation overcomes the ability of RBF3 to activate UPR and partially overcome PARP cleavage, this treatment did not prevent RBF3-mediated downregulation of HER1-3 expression (FIG. 2A-2D). Overall, the results of these experiments obtained with the use of 2-DOG and DTT suggest that the ability of RBF3 to induce cancer cell death results from a combination of UPR activation, HER1-3 downregulation, and decreased Akt phosphorylation.

Ideally, cancer therapeutic agents should be toxic to cancer cells with little or no impact on normal cells. The principles of "oncogene addiction [1, 53]" and "synthetic lethality [54, 55]" are strategies to realize this ideal. These approaches are exemplified by the use of BCR-Abl inhibitors for the treatment of Chronic Myelogenous Leukemia (CML), HER2-directed monoclonal antibodies and tyrosine kinase inhibitors for the treatment of HER2+ breast tumors, and PARP inhibitors for the treatment of BRCA1/2-mutant ovarian cancers. However, these approaches suffer from cancer "escape" from therapy through a variety of mechanisms. Thus, in many cases cancer cures may require multiple drugs to overcome both the driver oncogene and potential resistance mechanisms, or the discovery of multifunctional anticancer drugs that target the appropriate mechanisms.

Breast cancers devoid of Estrogen Receptor (ER−), Progesterone Receptor (PR−), and HER2 expression (HER2−) are termed Triple-Negative Breast Cancers. Currently, no targeted therapies for TNBCs exist. EGFR has been suggested as a therapeutic target for TNBCs [56, 57] and it has been estimated that up to 50% of TNBCs may overexpress EGFR at the protein level [28]. The potential for the use of DDAs against TNBCs is supported by the observation that the EGFR overexpressing MDA-MB-468 TNBC cell line is the most sensitive line to DDAs identified to date.

DDAs are selectively cytotoxic to breast cancer cells that overexpress either HER2 or EGFR and EGFR overexpression potentiates DDA-induced Akt dephosphorylation [33]. In the present study we examined whether EGFR overexpression also potentiates other DDA responses including HER3 downregulation and activation of ER stress. HER3 mediates a number of resistance mechanisms to HER2-targeted therapies through its ability to be phosphorylated by EGFR, IGF-1R, and c-MET [21, 58-61] and activate the PI3K/Akt pathway. In the T47D ER+ breast cancer cell line ectopic expression of either EGFR or HER2 rendered endogenous HER3 more sensitive to downregulation by the DDA NSC624205 (FIG. 2E), and EGFR overexpression sensitizes EGFR, HER2, and HER3 to RBF3-mediated downregulation (FIG. 2G).

A concern with DDAs relates to their ability to break disulfide bonds and potentially alter the function of multiple secreted or membrane proteins. A number of cell types that express normal levels of EGFR and HER2, such as T47D, MCF10/DCIS, MEF lines are unaffected by DDAs. However, T47D cells become responsive to the toxic effects of DDAs upon overexpression of EGFR or HER2 ([33] and herein (FIG. 2E-2G).

Since a side effect of Trastuzumab is cardiotoxicity, the possibility that DDAs might also be cardiotoxic is a concern. The results presented in FIG. 7 indicate that while the cardiomyocytes expressed high levels of HER2, there was no effect of RBF3 on HER2 levels in contrast to what is observed in cancer cells. Further, RBF3 had no effect on the beating of the cardiomyocytes in culture. We speculate that the reason that DDAs do not downregulate HER2 in cardiomyocytes is that in these cells HER2 is expressed at normal levels rather than being overexpressed. Therefore the addition of DDAs does not cause sufficient ER stress to kill cardiomyocytes. This is consistent with the observation that nearly all breast cancers express HER2, but DDAs are only toxic to the lines that exhibit dramatic HER2 or EGFR overexpression.

Figure 8A:
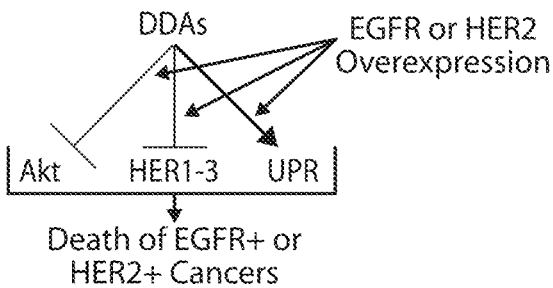
FIGS. 8A-8B. Model for the anticancer actions of DDAs.
Figure 8B:
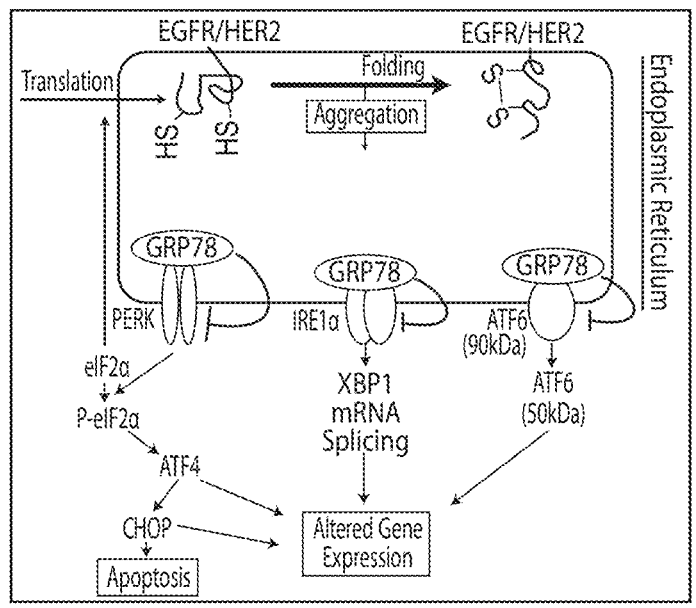
Figure 8B:
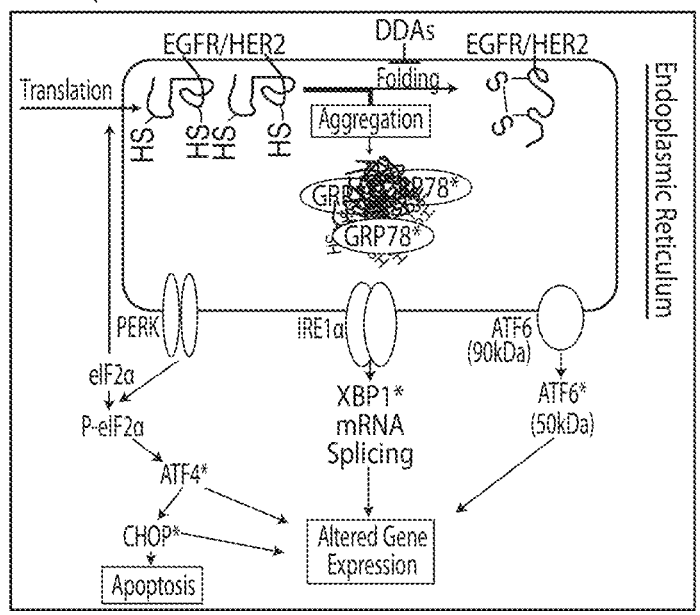
Figure 9A:
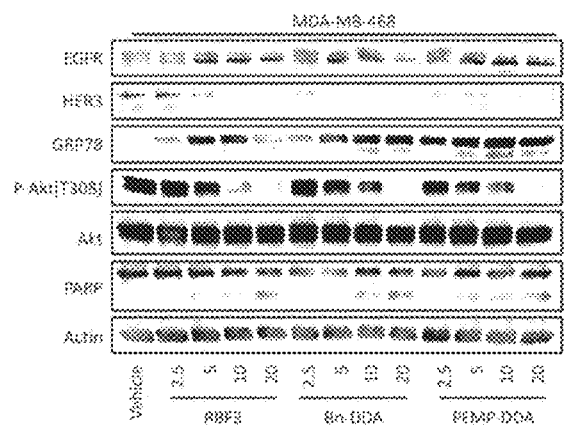
FIGS. 9A-9D. Replicate MDA-MB-468 (FIGS. 9A and 9B) and BT474 (FIGS. 9C and 9D) immunoblot panels.
Figure 9B:
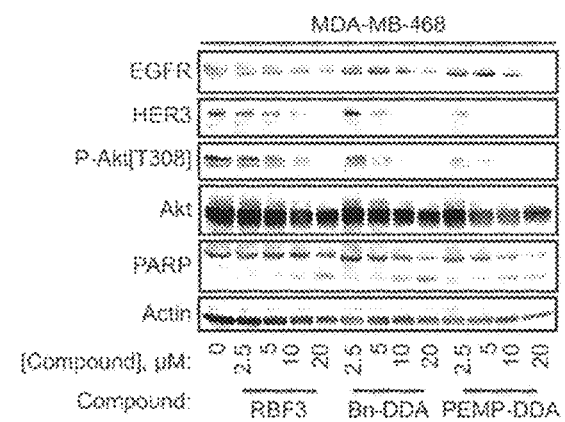
Figure 9C:
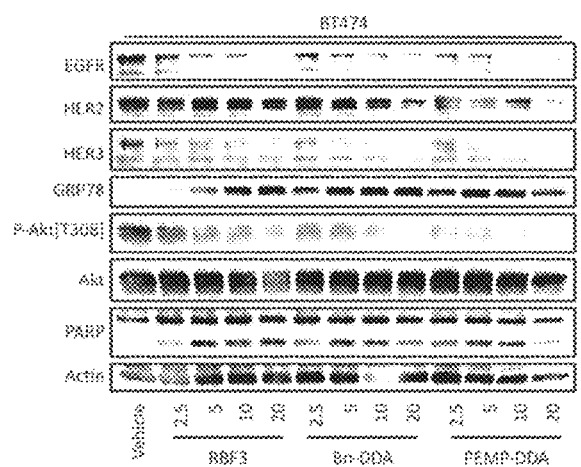
Figure 9D:
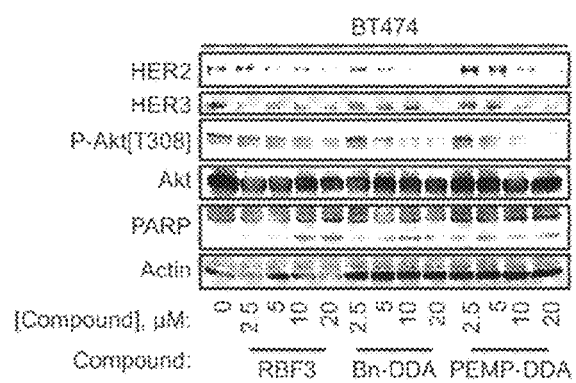

Because of the large number of disulfide bonds in the HER-family receptor cysteine-rich extracellular domains and the ability of DDAs to break disulfide bonds, we hypothesize that overexpression of HER-family receptors such as EGFR selectively exacerbate the ER stress induced by DDAs. Consistent with this expectation, EGFR overexpression in T47D cells potentiated RBF3-induced ER stress and this effect was particularly notable at early time points. We propose the model for DDA action in FIG. 8A where DDAs selectively induce the death of EGFR+ and HER2+ cancers through the suppression of Akt phosphorylation, downregulation of HER1-3 expression, and activation of UPR. DDA induction of UPR and Akt dephosphorylation are potentiated by overexpression of EGFR, or to a lesser extent, HER2. Due to their unique and multifunctional mechanisms of action, DDAs may be well suited for targeting the pathways responsible for resistance to HER2- and EGFR-targeted agents and prove to be complementary to other therapeutic modalities including monoclonal antibodies and receptor tyrosine kinase inhibitors targeting HER-family oncogenes. The high sensitivity of EGFR or HER2 overexpressing cancer cells to DDAs may derive from the large number of disulfide bonds in these proteins combined with the ability of DDAs to prevent the formation of Disulfide bonds in the ER (FIG. 8B). In addition to examining DDA effects on breast tumors with overexpression of wild type EGFR or HER2, in future studies it will be important to determine whether mutants or splice variants of these proteins, such as HER2-delta 16 [62-64] are responsive to DDAs.

Cyclic and linear forms of the DDA pharmacophore can interconvert, and elicit similar cellular responses. Slight structural modifications made to either form of the DDA pharmacophore result in loss of biological activity ([33] and FIG. 5H, 5I), but increasing the number of pharmacophores per molecule elevates DDA potency (FIGS. 5A-5G and FIG. 6A-6D). This suggests a modular lead optimization approach in which improvements are made to the activity of the pharmacophore structure, and the optimized pharmacophore is then appended to a polyvalent scaffold to further increase DDA potency. These efforts are currently ongoing in our laboratories.

Figure 11B:
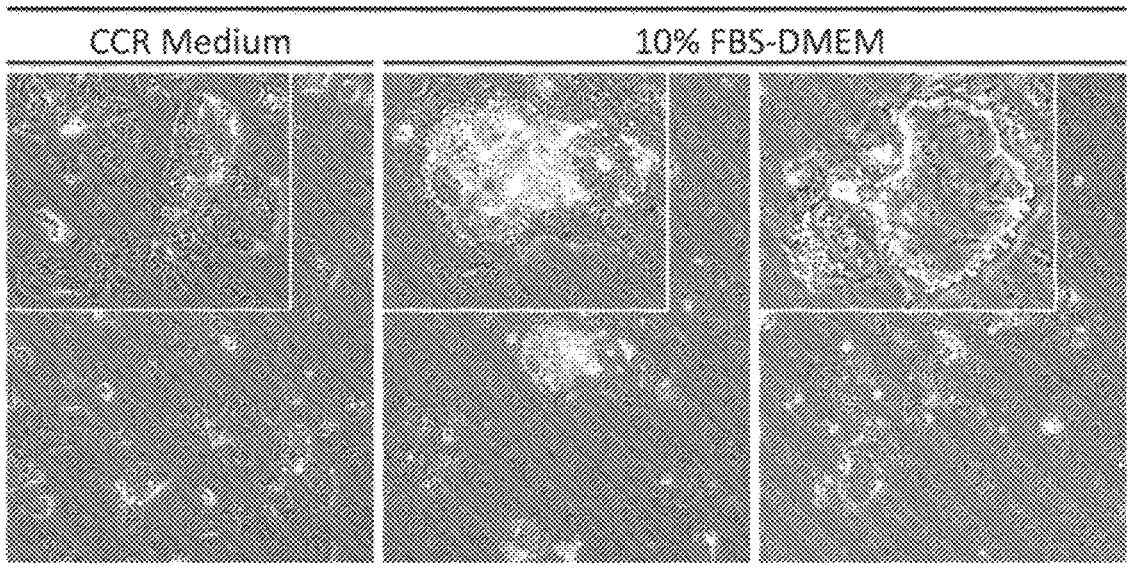
Figure 12A:
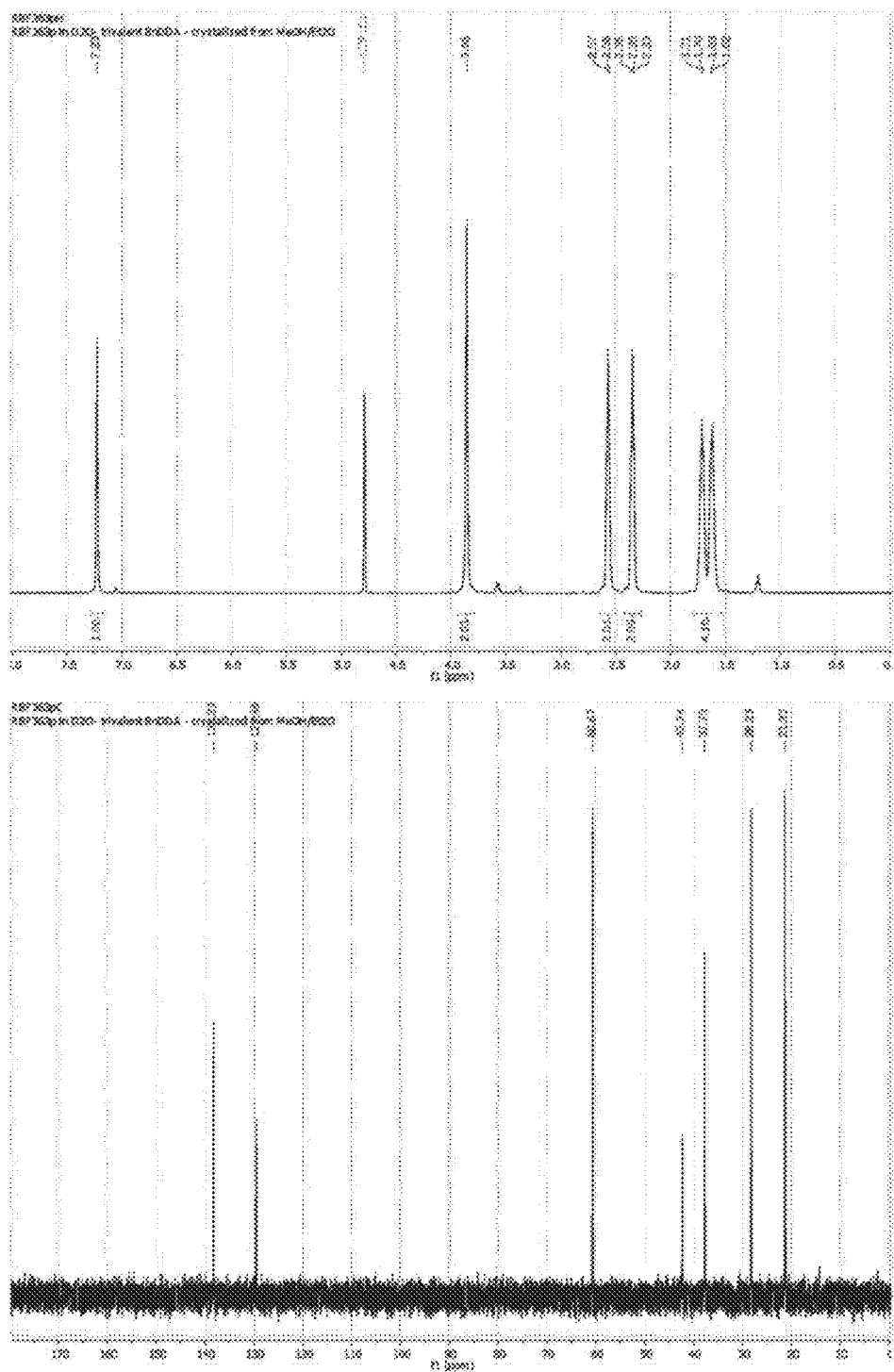
FIGS. 12A-12F. NMR spectra of synthesized DDA compounds.
Figure 12B:
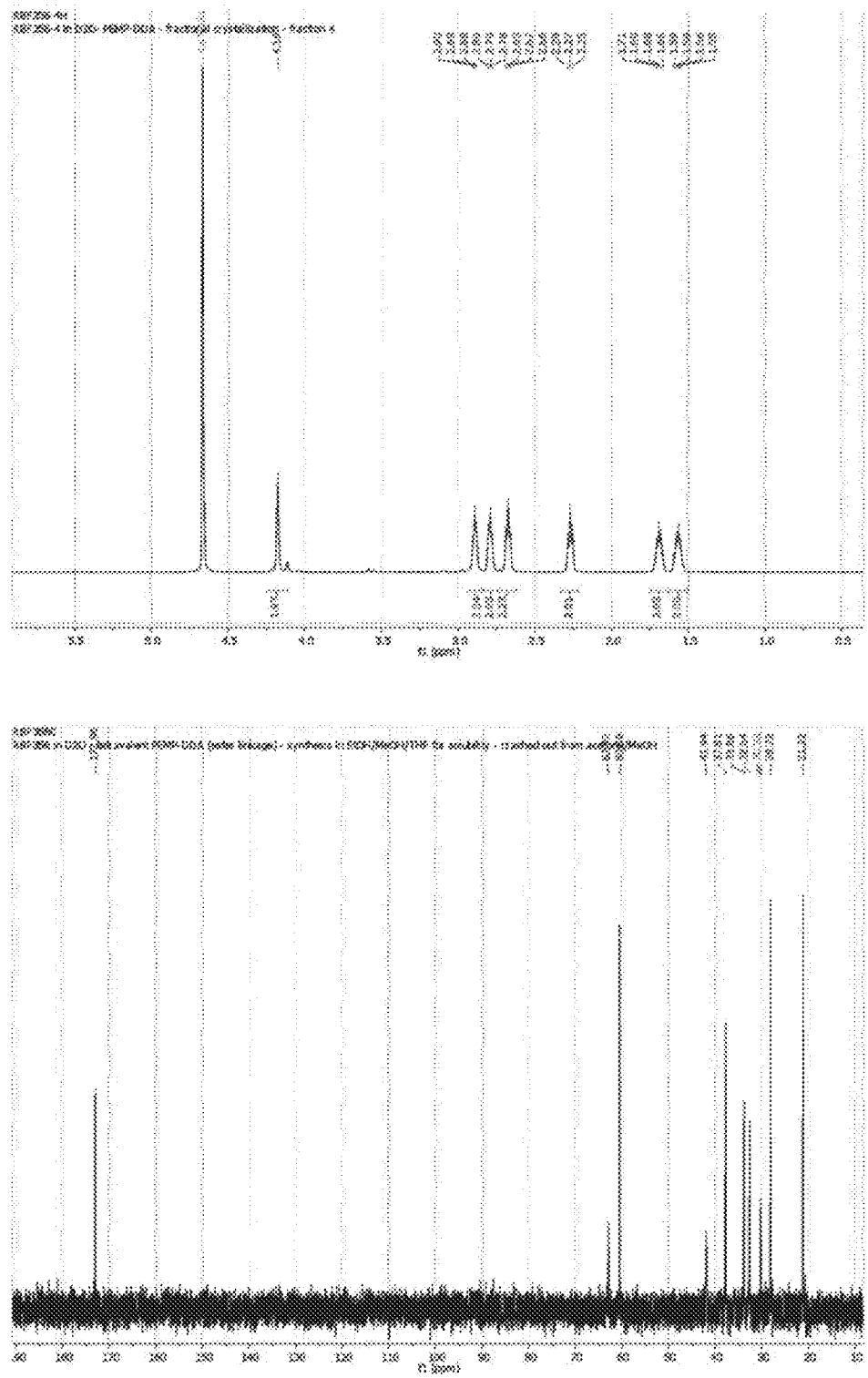
Figure 12C:
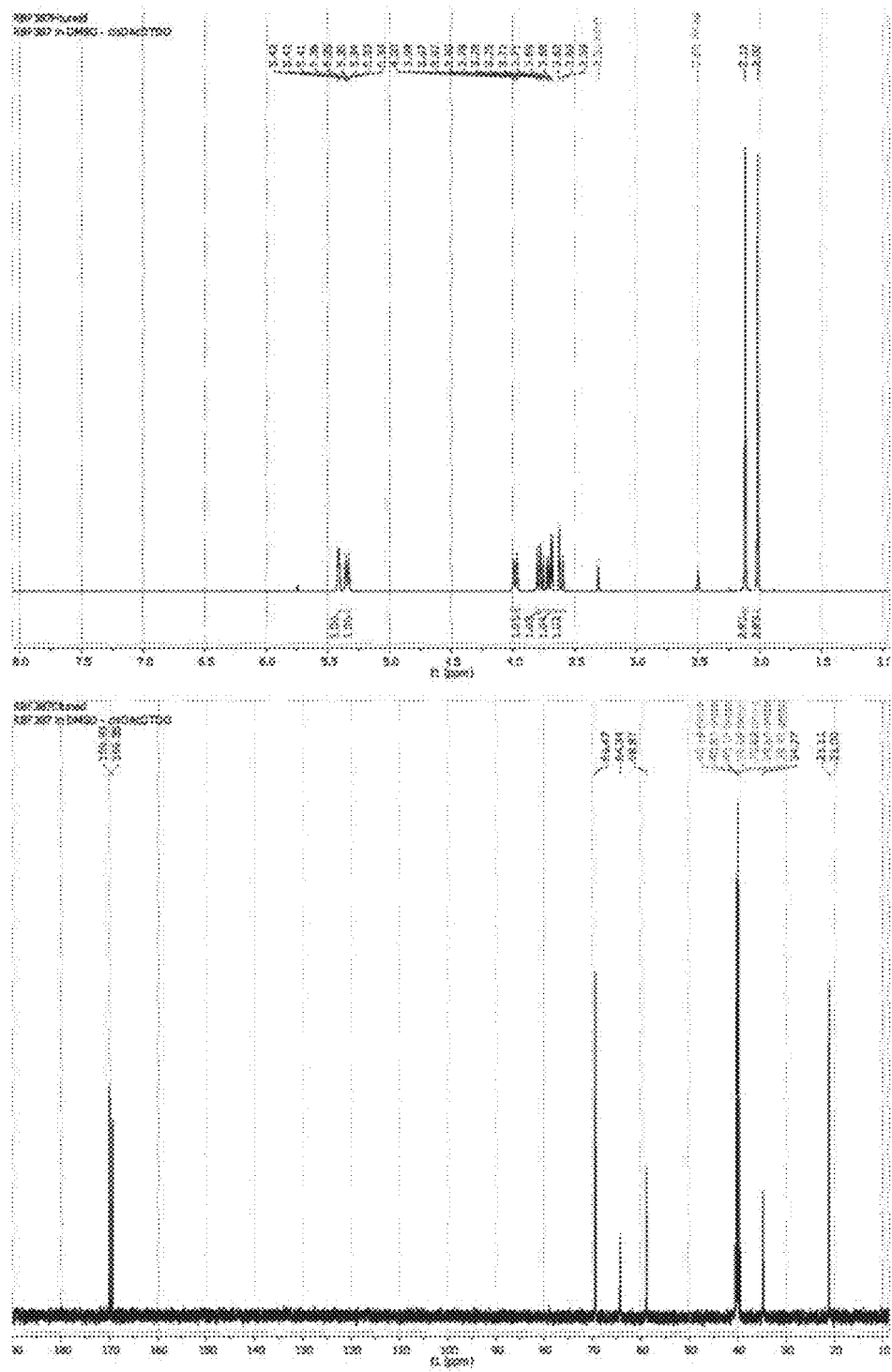
Figure 12D:
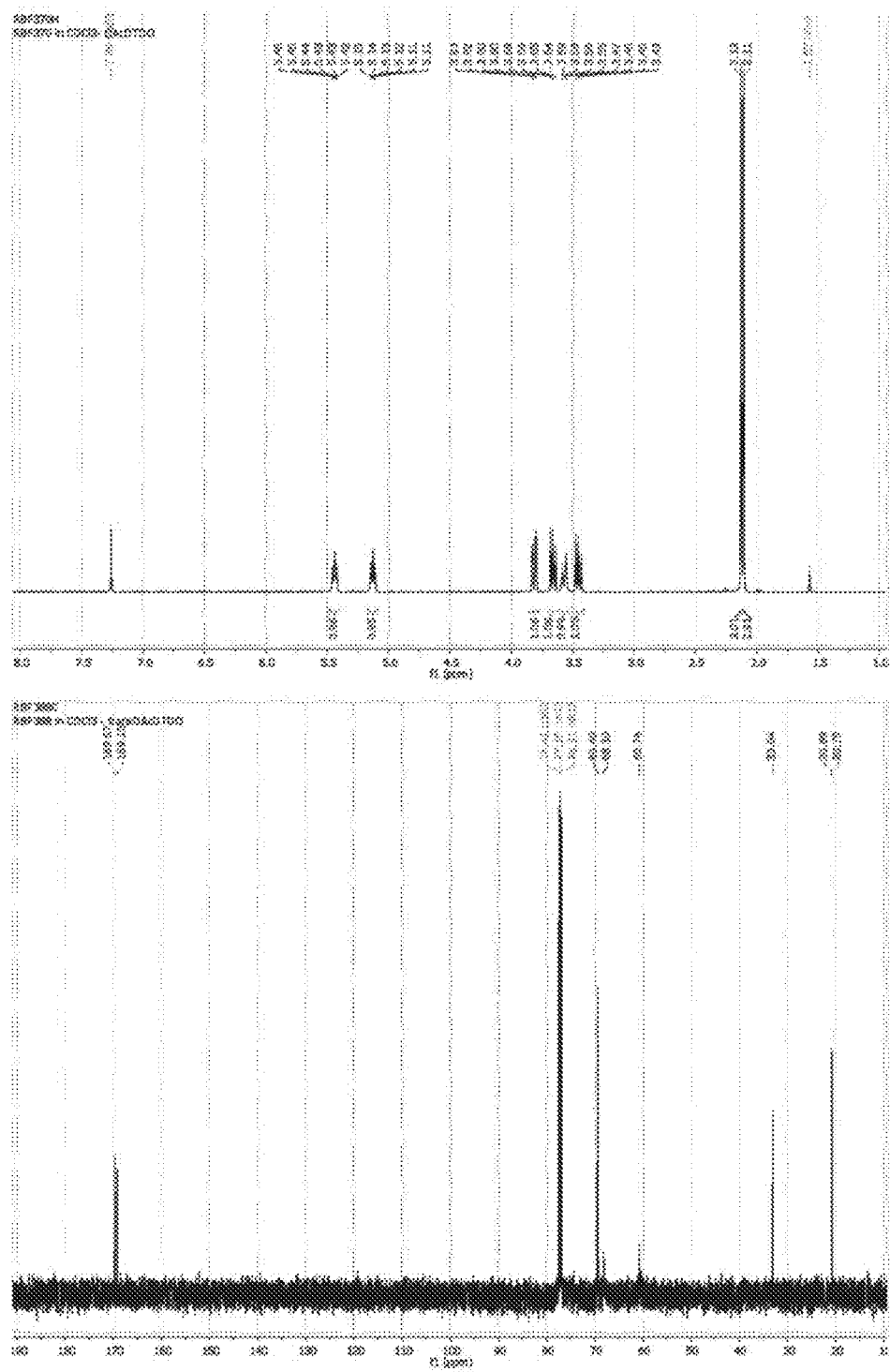
Figure 12E:
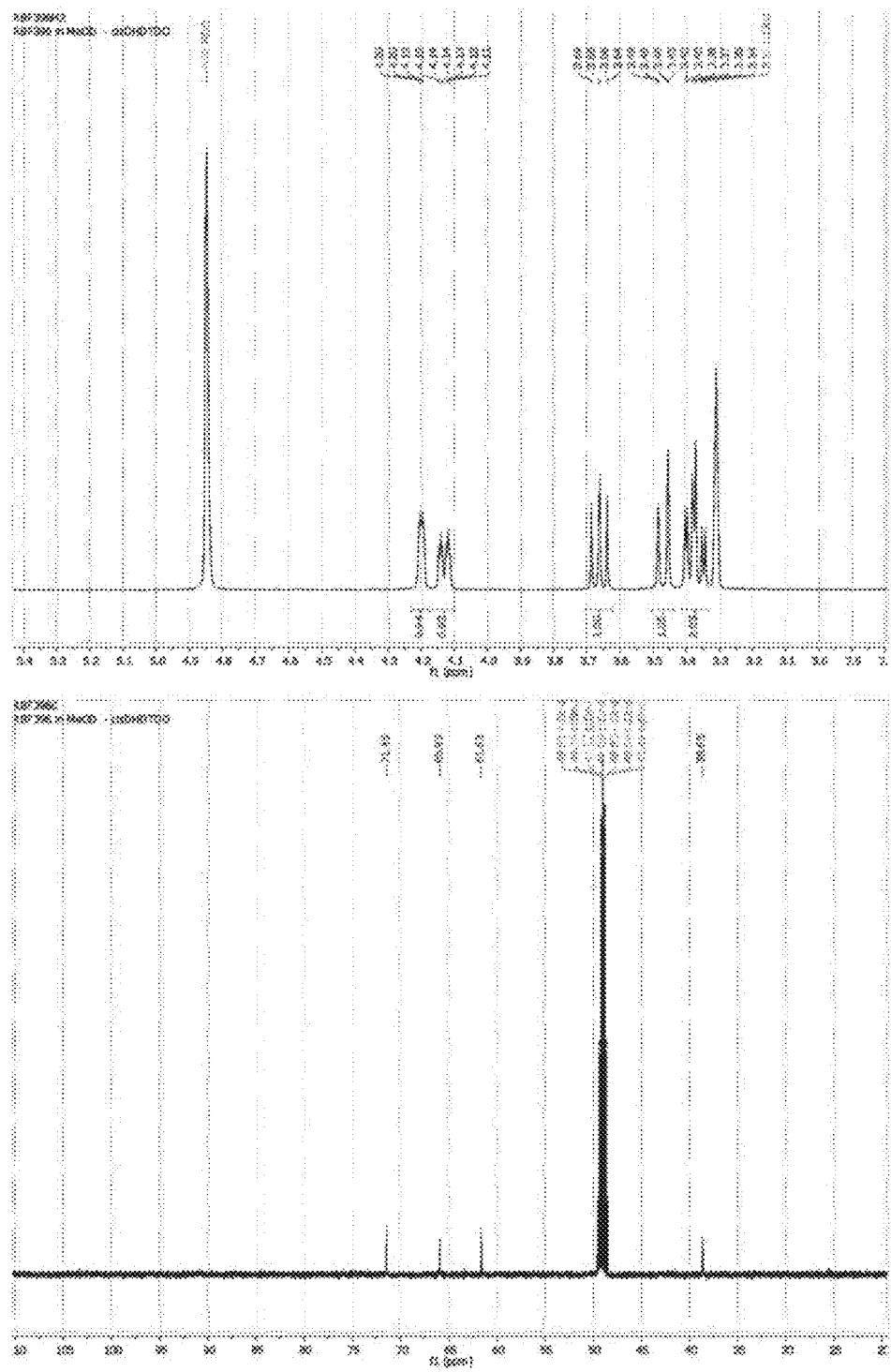
Figure 12F:
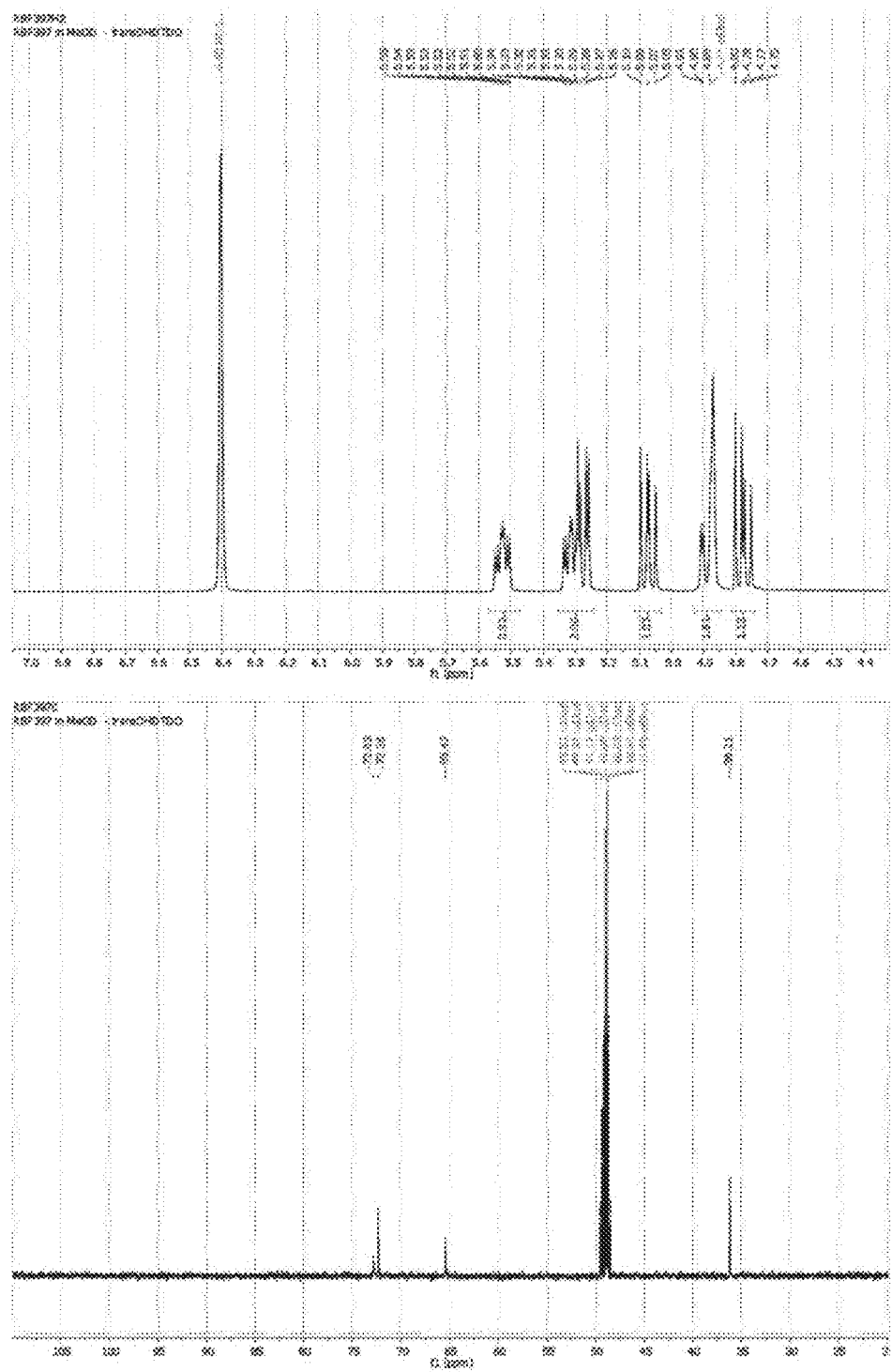

Materials and Methods:
Cell Lines, Construction of Stable Cell Lines, and Recombinant Adenoviruses The following cell lines were purchased from American Type Culture Collection (ATCC) (Manassas, Va.): MDA-MB-468, BT474, T47D, SKBR3, MDA-MB-231, HCC1954, HEK 293, TSC2-Ang1, and BxPC3. The HCI-012 cell line was derived from the HCI-012 Patient-Derived Xenograft tumor line provided by Dr. Alana Welm [40] using conditional cell reprogramming [41, 42, 65]. Characterization of the HCI-012 cell line is shown in FIGS. 11A-11B. Wild type and eIF2α[S51A] homozygous knock-in Mouse Embryo Fibroblasts (MEFs) were described previously [38].

Recombinant retroviruses were prepared and used to produce stable cell lines as described previously [66, 67]. Retroviral vectors encoding EGFR (plasmid 11011, [68]) and HER2 (plasmid 40978 [69]) were from Addgene (Cambridge, Mass.).

Cell Culture, Preparation of Cell Extracts, and Immunoblot Analysis

Cells were grown in Dulbecco's modified Eagle's medium (GE Healthcare Life Sciences Logan, Utah) supplemented with 10% fetal bovine serum (10% FBS-DMEM) in a humidified 37° C. incubator with 5% CO2. Cell lysates were prepared using a buffer containing 1% Triton X100, 20 mM HEPES (pH 7.4), 1 mM EDTA, 1 mM EGTA, 0.1% 3-mercaptoethanol, 5% glycerol, 10 nM microcystin, 200 µM Na3VO4 and 40 mM Na2H2P2O7 as described previously [70].

Immunoblot analysis was carried out using primary antibodies purchased from Santa Cruz Biotechnology (Dallas, Tex.) [Actin, sc-1616-R; ERK, sc-93; JNK, sc-572; P-JNK, sc-6254; Src, sc-18; EGFR, sc-03; GRP78, sc-13539; Phosphotyrosine (PY99), sc-7020], Cell Signaling Technology (Beverly, Mass.) [Akt, #4691; P-Akt[T308], #13038; P-Akt[S473], #9271; ATF4, #11815; CHOP, #2895; P-Src[Y527], #2105; EGFR, #4267; HER2, #2165; HER3, #4754; Calnexin, #2679; #13024; P-Erk, #9101; IRE1α, #3294; XBP1s, #12782; PARP, #9532; PDI, #3501; PERK, #5683; S6, #2212; P-S6, #2211; P-Src[Y416], #6943], BD Transduction Laboratories (San Jose, Calif.) [PAI-1, 612024], Millipore (Temecula, Calif.) [anti-phosphotyrosine (4G10), 05-321], and Sigma-Aldrich (St. Louis, Mo.) [anti-FLAG (M2), F3165]. To quantify immunoblot results, bands were analyzed using ImageJ (imagej.nih.gov/ij/) and each band was normalized to the corresponding Actin loading control band.

EGF (GF001) was obtained from Chemicon International (Temecula, Calif.). Lapatinib (sc-202205) was from Santa Cruz Biotechnology. NSC624205 was a gift from the National Cancer Institute's Developmental Therapeutics Program. The following reagents were purchased from the indicated sources: tunicamycin, 2-deoxyglucose: Sigma-Aldrich (St. Louis, Mo.); 2-aminoethoxydiphenyl borate (2-APB): StressMarq Biosciences (Cadboro Bay, Victoria, Canada); thapsigargin: AdipoGen (San Diego, Calif.); Puromycin, Rapamycin, Cycloheximide: EMD Biosciences (Darmstadt, Germany); Gefitinib, Lapatinib, SAHA: Selleck Chemicals (Houston, Tex.); dithiothreitol: Fisher Scientific (Pittsburgh, Pa.).

Transfection of HEK293 Cells and Luciferase Assays—

Transfections were performed using Lipofectamine Reagent (Invitrogen, Carlsbad, Calif.) according to the manufacturer's instructions. Cells were incubated for 48 hours after transfection, and cell extracts analyzed by luciferase assays, with background readings subtracted from the luciferase assay values. Relative Luminescence Units (RLUs) were normalized to the number of micrograms of protein assayed. The results are presented as the mean of triplicate determinations±standard deviation. The ATF6 Reporter (plasmid 11976 [71]) and FLAG-ATF6a (plasmid 11975 [72]) constructs were obtained from Addgene.

MTT Cell Viability Assays—

Cell viability was evaluated using MTT (3-(4,5-dimethylthiazol-2-yl)-2,5-diphenyltetrazolium bromide) assays carried out based on the manufacturer's instructions (kit CGD1, Sigma-Aldrich, St. Louis, Mo.)

Thymidine Incorporation Assays—

Tritiated thymidine incorporation assays were performed as described previously [73]. Results are presented as the mean±standard deviation of triplicate or quadruplicate determinations.

RT-PCR—

RNA was isolated from MDA-MB-468 and BT474 cells with Trizol Reagent (Invitrogen) according to the manufacturer's instructions, and reverse transcribed to cDNA under the following conditions: 25° C. for 10 min, 42° C. for 30 min, and 95° C. for 5 min. PCR was performed using XBP1 and β-Actin primers. The primers used to amplify XBP1 are as follows: Forward: CCTGGTTGCTGAAGAGGAGG and Reverse: CCATGGGGAGATGTTCTGGAG. The primers used to amplify (3-Actin are as follows: Forward: GGATGCAGAAGGAGATCAC and Reverse: AAGGTGGACAGCGAGGCCAG. Reactions were performed as follows: 96° C. for 5 min followed by 35 cycles of 95° C. for 45 sec, 60° C. for 1 min, and 72° C. for 30 sec. Reaction products were visualized on 3% agarose gels.

Synthesis of DDAs—

DDA synthesis and characterization is presented below and in FIGS. 12A-12F.

Cardiomyocyte Differentiation—

To induce cardiomyocyte differentiation we utilized the PSC Cardiomyocyte Differentiation Kit (ThermoFisher, Grand Island, N.Y.). Briefly, human iPSCs were grown in feeder-free conditions using hES qualified Matrigel (Corning, Auburn, Mich.) and mTeSR1 medium (Stem Cell Technologies, Vancouver, BC, Canada). iPSC colonies were dissociated from one 35 mm dish using Gentle Cell Dissociation Reagent (Stem Cell Technologies) for eight minutes at 37° C. to make a single cell suspension. The cells were divided equally among the wells of a 12-well plate coated with Matrigel using mTeSR1 medium and ROCK inhibitor (10 uM final concentration for the first 24 hours). Medium was changed daily with mTeSR1 until the iPSCs formed a monolayer of approximately 80% confluency. To induce mesoderm differentiation, Cardiomyocyte Differentiation Medium A was added for 48 hours (Days 0-2). For cardiac mesoderm specification, Cardiomyocyte Differentiation Medium B was added for the next 48 hours (Days 2-4). For cardiomyocyte maturation, cells were maintained in Cardiomyocyte Maintenance Medium for the duration of culture (Day 4+), replacing medium every other day. Spontaneous cell contraction began on day 10.

REFERENCES

1. Jonkers J and Berns A. Oncogene addiction: sometimes a temporary slavery. Cancer Cell. 2004; 6:535-538.
2. Weinstein I B and Joe A K. Mechanisms of disease: Oncogene addiction—a rationale for molecular targeting in cancer therapy. Nat Clin Pract Oncol. 2006; 3:448-457.
3. Pagliarini R, Shao W and Sellers W R. Oncogene addiction: pathways of therapeutic response, resistance, and road maps toward a cure. EMBO Rep. 2015; 16:280-296.
4. Baselga J, Tripathy D, Mendelsohn J, Baughman S, Benz C C, Dantis L, Sklarin N T, Seidman A D, Hudis C A, Moore J, Rosen P P, Twaddell T, Henderson I C and Norton L. Phase II study of weekly intravenous trastuzumab (Herceptin) in patients with HER2/neu-overexpressing metastatic breast cancer. Semin Oncol. 1999; 26:78-83.

5. Molina M A, Codony-Servat J, Albanell J, Rojo F, Arribas J and Baselga J. Trastuzumab (herceptin), a humanized anti-Her2 receptor monoclonal antibody, inhibits basal and activated Her2 ectodomain cleavage in breast cancer cells. Cancer Res. 2001; 61:4744-4749.
6. Pegram M D and O'Callaghan C. Combining the anti-HER2 antibody trastuzumab with taxanes in breast cancer: results and trial considerations. Clin Breast Cancer. 2001; 2 Suppl1:S15-19.
7. McKeage K and Perry C M. Trastuzumab: a review of its use in the treatment of metastatic breast cancer overexpressing HER2. Drugs. 2002; 62:209-243.
8. Blumenthal G M, Scher N S, Cortazar P, Chattopadhyay S, Tang S, Song P, Liu Q, Ringgold K, Pilaro A M, Tilley A, King K E, Graham L, Rellahan B L, Weinberg W C, Chi B, Thomas C, et al. First FDA approval of dual anti-HER2 regimen: pertuzumab in combination with trastuzumab and docetaxel for HER2-positive metastatic breast cancer. Clin Cancer Res. 2013; 19:4911-4916.
9. Harbeck N, Beckmann M W, Rody A, Schneeweiss A, Muller V, Fehm T, Marschner N, Gluz O, Schrader I, Heinrich G, Untch M and Jackisch C. HER2 Dimerization Inhibitor Pertuzumab—Mode of Action and Clinical Data in Breast Cancer. Breast Care (Basel). 2013; 8:49-55.
10. O'Sullivan C C and Swain S M. Pertuzumab: evolving therapeutic strategies in the management of HER2-overexpressing breast cancer. Expert Opin Biol Ther. 2013; 13:779-790.
11. Johnston S R and Leary A. Lapatinib: a novel EGFR/HER2 tyrosine kinase inhibitor for cancer. Drugs Today (Barc). 2006; 42:441-453.
12. Montemurro F, Valabrega G and Aglietta M. Lapatinib: a dual inhibitor of EGFR and HER2 tyrosine kinase activity. Expert Opin Biol Ther. 2007; 7:257-268.
13. Tuma R S. Lapatinib moves forward in inflammatory and early HER2-positive breast cancer trials. J Natl Cancer Inst. 2007; 99:348-349.
14. Blackwell K L, Pegram M D, Tan-Chiu E, Schwartzberg L S, Arbushites M C, Maltzman J D, Forster J K, Rubin S D, Stein S H and Burstein H J. Single-agent lapatinib for HER2-overexpressing advanced or metastatic breast cancer that progressed on first- or second-line trastuzumab-containing regimens. Ann Oncol. 2009; 20:1026-1031.
15. Knuefermann C, Lu Y, Liu B, Jin W, Liang K, Wu L, Schmidt M, Mills G B, Mendelsohn J and Fan Z. HER2/PI-3K/Akt activation leads to a multidrug resistance in human breast adenocarcinoma cells. Oncogene. 2003; 22:3205-3212.
16. Nahta R and Esteva F J. HER2 therapy: molecular mechanisms of trastuzumab resistance. Breast Cancer Res. 2006; 8:215.
17. Valabrega G, Montemurro F and Aglietta M. Trastuzumab: mechanism of action, resistance and future perspectives in HER2-overexpressing breast cancer. Ann Oncol. 2007; 18:977-984.
18. Liu L, Greger J, Shi H, Liu Y, Greshock J, Annan R, Halsey W, Sathe G M, Martin A M and Gilmer T M. Novel mechanism of lapatinib resistance in HER2-positive breast tumor cells: activation of AXL. Cancer Res. 2009; 69:6871-6878.
19. Hu S, Fu W, Xu W, Yang Y, Cruz M, Berezov S D, Jorissen D, Takeda H and Zhu W. Four-in-one antibodies have superior cancer inhibitory activity against EGFR, HER2, HER3, and VEGF through disruption of HER/MET crosstalk. Cancer Res. 2015; 75:159-170.
20. Claus J, Patel G, Ng T and Parker P J. A role for the pseudokinase HER3 in the acquired resistance against EGFR- and HER2-directed targeted therapy. Biochem Soc Trans. 2014; 42:831-836.
21. Xia W, Petricoin E F, 3rd, Zhao S, Liu L, Osada T, Cheng Q, Wulfkuhle J D, Gwin W R, Yang X, Gallagher R I, Bacus S, Lyerly H K and Spector N L. An heregulin-EGFR-HER3 autocrine signaling axis can mediate acquired lapatinib resistance in HER2+ breast cancer models. Breast Cancer Res. 2013; 15:R85.
22. Wu Y, Zhang Y, Wang M, Li Q, Qu Z, Shi V, Kraft P, Kim S, Gao Y, Pak J, Youngster S, Horak I D and Greenberger L M. Downregulation of HER3 by a novel antisense oligonucleotide, EZN-3920, improves the antitumor activity of EGFR and HER2 tyrosine kinase inhibitors in animal models. Mol Cancer Ther. 2013; 12:427-437.
23. Dufey E, Urra H and Hetz C. ER proteostasis addiction in cancer biology: Novel concepts. Semin Cancer Biol. 2015; 33:40-47.
24. Liu Y and Ye Y. Proteostasis regulation at the endoplasmic reticulum: a new perturbation site for targeted cancer therapy. Cell Res. 2011; 21:867-883.
25. Singh N, Joshi R and Komurov K. HER2-mTOR signaling-driven breast cancer cells require ER-associated degradation to survive. Sci Signal. 2015; 8:ra52.
26. Milanezi F, Carvalho S and Schmitt F C. EGFR/HER2 in breast cancer: a biological approach for molecular diagnosis and therapy. Expert Rev Mol Diagn. 2008; 8:417-434.
27. Jardines L, Weiss M, Fowble B and Greene M. neu(c-erbB-2/HER2) and the epidermal growth factor receptor (EGFR) in breast cancer. Pathobiology. 1993; 61:268-282.
28. Martin V, Botta F, Zanellato E, Molinari F, Crippa S, Mazzucchelli L and Frattini M. Molecular characterization of EGFR and EGFR-downstream pathways in triple negative breast carcinomas with basal like features. Histol Histopathol. 2012; 27:785-792.
29. Wang K, Ma Q, Ren Y, He J, Zhang Y, Zhang Y and Chen W. Geldanamycin destabilizes HER2 tyrosine kinase and suppresses Wnt/beta-catenin signaling in HER2 overexpressing human breast cancer cells. Oncol Rep. 2007; 17:89-96.
30. Zheng F F, Kuduk S D, Chiosis G, Munster P N, Sepp-Lorenzino L, Danishefsky S J and Rosen N. Identification of a geldanamycin dimer that induces the selective degradation of HER-family tyrosine kinases. Cancer Res. 2000; 60:2090-2094.
31. Li Y P, Chen J J, Shen J J, Cui J, Wu L Z, Wang Z and Li Z R. Synthesis and biological evaluation of geldanamycin analogs against human cancer cells. Cancer Chemother Pharmacol. 2015; 75:773-782.
32. Xiong M P, Yanez J A, Remsberg C M, Ohgami Y, Kwon G S, Davies N M and Forrest M L. Formulation of a geldanamycin prodrug in mPEG-b-PCL micelles greatly enhances tolerability and pharmacokinetics in rats. J Control Release. 2008; 129:33-40.
33. Ferreira R B, Law M E, Jahn S C, Davis B J, Heldermon C D, Reinhard M, Castellano R K and Law B K. Novel agents that downregulate EGFR, HER2, and HER3 in parallel. Oncotarget. 2015; 6:10445-10459.
34. Marciniak S J, Yun C Y, Oyadomari S, Novoa I, Zhang Y, Jungreis R, Nagata K, Harding H P and Ron D. CHOP induces death by promoting protein synthesis and oxidation in the stressed endoplasmic reticulum. Genes Dev. 2004; 18:3066-3077.
35. Yamaguchi H and Wang H G. CHOP is involved in endoplasmic reticulum stress-induced apoptosis by 35. enhancing DR5 expression in human carcinoma cells. J Biol Chem. 2004; 279:45495-45502.
36. Li F, Guo Y, Sun S, Jiang X, Tang B, Wang Q and Wang L. Free cholesterol-induced macrophage apoptosis is mediated by inositol-requiring enzyme 1 alpha-regulated activation of Jun N-terminal kinase. Acta Biochim Biophys Sin (Shanghai). 2008; 40:226-234.
37. Kumar R, Azam S, Sullivan J M, Owen C, Cavener D R, Zhang P, Ron D, Harding H P, Chen J J, Han A, White B C, Krause G S and DeGracia D J. Brain ischemia and reperfusion activates the eukaryotic initiation factor 2alpha kinase, PERK. J Neurochem. 2001; 77:1418-1421.
38. Scheuner D, Song B, McEwen E, Liu C, Laybutt R, Gillespie P, Saunders T, Bonner-Weir S and Kaufman R J. Translational control is required for the unfolded protein response and in vivo glucose homeostasis. Mol Cell. 2001; 7:1165-1176.
39. Whittle J R, Lewis M T, Lindeman G J and Visvader J E. Patient-derived xenograft models of breast cancer and their predictive power. Breast Cancer Res. 2015; 17:17.
40. DeRose Y S, Wang G, Lin Y C, Bernard P S, Buys S S, Ebbert M T, Factor R, Matsen C, Milash B A, Nelson E, Neumayer L, Randall R L, Stijleman I J, Welm B E and Welm A L. Tumor grafts derived from women with breast cancer authentically reflect tumor pathology, growth, metastasis and disease outcomes. Nat Med. 2011; 17:1514-1520.
41. Palechor-Ceron N, Suprynowicz F A, Upadhyay G, Dakic A, Minas T, Simic V, Johnson M, Albanese C, Schlegel R and Liu X. Radiation induces diffusible feeder cell factor(s) that cooperate with ROCK inhibitor to conditionally reprogram and immortalize epithelial cells. Am J Pathol. 2013; 183:1862-1870.
42. Liu X, Ory V, Chapman S, Yuan H, Albanese C, Kallakury B, Timofeeva O A, Nealon C, Dakic A, Simic V, Haddad B R, Rhim J S, Dritschilo A, Riegel A, McBride A and Schlegel R. ROCK inhibitor and feeder cells induce the conditional reprogramming of epithelial cells. Am J Pathol. 2012; 180:599-607.
43. Chakrabarty A, Rexer B N, Wang S E, Cook R S, Engelman J A and Arteaga C L. H1047R phosphatidylinositol 3-kinase mutant enhances HER2-mediated transformation by heregulin production and activation of HER3. Oncogene. 2010; 29:5193-5203.
44. Martin K A, Merenick B L, Ding M, Fetalvero K M, Rzucidlo E M, Kozul C D, Brown D J, Chiu H Y, Shyu M, Drapeau B L, Wagner R J and Powell R J. Rapamycin promotes vascular smooth muscle cell differentiation through insulin receptor substrate-1/phosphatidylinositol 3-kinase/Akt2 feedback signaling. J Biol Chem. 2007; 282:36112-36120.
45. O'Reilly K E, Rojo F, She Q B, Solit D, Mills G B, Smith D, Lane H, Hofmann F, Hicklin D J, Ludwig D L, Baselga J and Rosen N. mTOR inhibition induces upstream receptor tyrosine kinase signaling and activates Akt. Cancer Res. 2006; 66:1500-1508.
46. Sadowski K, Kotulska K and Jozwiak S. Management of side effects of mTOR inhibitors in tuberous sclerosis patients. Pharmacol Rep. 2016; 68:536-542.
47. Sampson J R. Therapeutic targeting of mTOR in tuberous sclerosis. Biochem Soc Trans. 2009; 37:259-264.
48. Bai F, Ho Lim C, Jia J, Santostefano K, Simmons C, Kasahara H, Wu W, Terada N and Jin S. Directed Differentiation of Embryonic Stem Cells Into Cardiomyocytes by Bacterial Injection of Defined Transcription Factors. Sci Rep. 2015; 5:15014.
49. Singh A M, Li F Q, Hamazaki T, Kasahara H, Takemaru K and Terada N. Chibby, an antagonist of the Wnt/beta-catenin pathway, facilitates cardiomyocyte differentiation of murine embryonic stem cells. Circulation. 2007; 115:617-626.
50. Farnie G, Willan P M, Clarke R B and Bundred N J. Combined inhibition of ErbB1/2 and Notch receptors effectively targets breast ductal carcinoma in situ (DCIS) stem/progenitor cell activity regardless of ErbB2 status. PLoS One. 2013; 8:e56840.
51. Kaji E H and Lodish H F. In vitro unfolding of retinol-binding protein by dithiothreitol. Endoplasmic reticulum-associated factors. J Biol Chem. 1993; 268:22195-22202.
52. Braakman I, Helenius J and Helenius A. Manipulating disulfide bond formation and protein folding in the endoplasmic reticulum. EMBO J. 1992; 11:1717-1722.
53. Workman P. Cancer genome targets: RAF-ing up tumor cells to overcome oncogene addiction. Expert Rev Anticancer Ther. 2002; 2:611-614.
54. Kaelin W G, Jr. The concept of synthetic lethality in the context of anticancer therapy. Nat Rev Cancer. 2005; 5:689-698.
55. Garber K. Synthetic lethality: killing cancer with cancer. J Natl Cancer Inst. 2002; 94:1666-1668.
56. Livasy C A, Karaca G, Nanda R, Tretiakova M S, Olopade O I, Moore D T and Perou C M. Phenotypic evaluation of the basal-like subtype of invasive breast carcinoma. Mod Pathol. 2006; 19:264-271.
57. Monaghan P, Clarke C L, Perusinghe N P, Ormerod M G and O'Hare M J. Epidermal growth factor receptor expression on human breast luminal and basal cells in vitro. Epithelial Cell Biol. 1995; 4:52-62.
58. Arteaga C L. HER3 and mutant EGFR meet MET. Nat Med. 2007; 13:675-677.
59. Zhang Z, Wang J, Ji D, Wang C, Liu R, Wu Z, Liu L, Zhu D, Chang J, Geng R, Xiong L, Fang Q and Li J. Functional genetic approach identifies MET, HER3, IGF1R, INSR pathways as determinants of lapatinib unresponsiveness in HER2-positive gastric cancer. Clin Cancer Res. 2014; 20:4559-4573.
60. Jia Y, Zhang Y, Qiao C, Liu G, Zhao Q, Zhou T, Chen G, Li Y, Feng J, Li Y, Zhang Q and Peng H. IGF-1R and ErbB3/HER3 contribute to enhanced proliferation and carcinogenesis in trastuzumab-resistant ovarian cancer model. Biochem Biophys Res Commun. 2013; 436:740-745.
61. Desbois-Mouthon C, Baron A, Blivet-Van Eggelpoel M J, Fartoux L, Venot C, Bladt F, Housset C and Rosmorduc O. Insulin-like growth factor-1 receptor inhibition induces a resistance mechanism via the epidermal growth factor receptor/HER3/AKT signaling pathway: rational basis for cotargeting insulin-like growth factor-1 receptor and epidermal growth factor receptor in hepatocellular carcinoma. Clin Cancer Res. 2009; 15:5445-5456.
62. Wada R, Yagihashi S and Naito Z. mRNA expression of delta-HER2 and its clinicopathological correlation in HER2-overexpressing breast cancer. Mol Med Rep. 2016; 14:5104-5110.
63. Alajati A, Sausgruber N, Aceto N, Duss S, Sarret S, Voshol H, Bonenfant D and Bentires-Alj M. Mammary tumor formation and metastasis evoked by a HER2 splice variant. Cancer Res. 2013; 73:5320-5327.
64. Cittelly D M, Das P M, Salvo V A, Fonseca J P, Burow M E and Jones F E. Oncogenic HER2{Delta} 16 suppresses miR-15a/16 and deregulates BCL-2 to promote endocrine resistance of breast tumors. Carcinogenesis. 2010; 31:2049-2057.
65. Yuan H, Myers S, Wang J, Zhou D, Woo J A, Kallakury B, Ju A, Bazylewicz M, Carter Y M, Albanese C, Grant N, Shad A, Dritschilo A, Liu X and Schlegel R. Use of reprogrammed cells to identify therapy for respiratory papillomatosis. N Engl J Med. 2012; 367:1220-1227.
66. Law M E, Corsino P E, Jahn S C, Davis B J, Chen S, Patel B, Pham K, Lu J, Sheppard B, Norgaard P, Hong J, Higgins P, Kim J S, Luesch H and Law B K. Glucocorticoids and histone deacetylase inhibitors cooperate to block the invasiveness of basal-like breast cancer cells through novel mechanisms. Oncogene. 2013; 32:1316-1329.
67. Law M E, Ferreira R B, Davis B J, Higgins P J, Kim J S, Castellano R K, Chen S, Luesch H and Law B K. CUB domain-containing protein 1 and the epidermal growth factor receptor cooperate to induce cell detachment. Breast Cancer Res. 2016; 18:80.
68. Greulich H, Chen T H, Feng W, Janne P A, Alvarez J V, Zappaterra M, Bulmer S E, Frank D A, Hahn W C, Sellers W R and Meyerson M. Oncogenic transformation by inhibitor-sensitive and -resistant EGFR mutants. PLoS Med. 2005; 2:e313.
69. Greulich H, Kaplan B, Mertins P, Chen T H, Tanaka K E, Yun C H, Zhang X, Lee S H, Cho J, Ambrogio L, Liao R, Imielinski M, Banerji S, Berger A H, Lawrence M S, Zhang J, et al. Functional analysis of receptor tyrosine kinase mutations in lung cancer identifies oncogenic extracellular domain mutations of ERBB2. Proc Natl Acad Sci USA. 2012; 109:14476-14481.
70. Law B K, Chytil A, Dumont N, Hamilton E G, Waltner-Law M E, Aakre M E, Covington C and Moses H L. Rapamycin potentiates transforming growth factor beta-induced growth arrest in nontransformed, oncogene-transformed, and human cancer cells. Mol Cell Biol. 2002; 22:8184-8198.
71. Wang Y, Shen J, Arenzana N, Tirasophon W, Kaufman R J and Prywes R. Activation of ATF6 and an ATF6 DNA binding site by the endoplasmic reticulum stress response. J Biol Chem. 2000; 275:27013-27020.
72. Chen X, Shen J and Prywes R. The luminal domain of ATF6 senses endoplasmic reticulum (ER) stress and causes translocation of ATF6 from the ER to the Golgi. J Biol Chem. 2002; 277:13045-13052.
73. Law B K, Norgaard P, Gnudi L, Kahn B B, Poulson H S and Moses H L. Inhibition of DNA synthesis by a farnesyltransferase inhibitor involves inhibition of the p70(s6k) pathway. J Biol Chem. 1999; 274:4743-4748.

Supplemental Material:

General Methods: Reagents and solvents were purchased from commercial sources and used without further purification unless otherwise specified. $^1$H and $^{13}$C NMR spectra were recorded using commercially obtained (Cambridge Isotope Laboratories) deuterated solvents on a Varian lnova-500 ($^1$H at 500 MHz; $^{13}$C at 126 MHz) spectrometer. Chemical shifts (δ) are given in parts per million (ppm) relative to tetramethylsilane (TMS) and referenced to residual protonated solvent (CDCl$_3$: δ H 7.26 ppm, δ C 77.23 ppm; CD$_3$OD: δ H 4.87 ppm, δ C 49.00 ppm; DMSO-d$_6$: δ H 2.50 ppm, δ C 39.52 ppm; D$_2$O: δ H 4.79 ppm). Coupling constants are given in Hz. Spin multiplicities are presented by the following symbols: s (singlet), bs (broad singlet), d (doublet), t (triplet), q (quartet), p (pentet), and m (multiplet). Electrospray ionization (ESI) or Direct Analysis in Real Time (DART) high resolution mass spectra (HRMS) were recorded on an Agilent 6200 ES1-TOF instrument, operating in positive or negative ion mode as stated, with methanol as the carrier solvent for ESI experiments. Matrix-Assisted Laser Desorption Ionization (MALDI) HRMS were recorded on a Bruker Microflex LRF MALDI TOF instrument, with a matrix mixture of DHB/analyte 1:1.

RBF3 and DTDO were synthesized as described in our previous publication (1). NMR spectra of the synthesized compounds are shown in FIGS. 12A-12F.

A. Bn-DDA:

To a stirring solution of benzene-1,3,5-triyltrimethanethiol (150 mg, 0.693 mmol) and DTDO (475 mg, 3.12 mmol) in MeOH/THF 2:1 (6.3 ml) at 0° C., a solution of NaOMe (freshly prepared from 48 mg of Na$^0$ and 1.5 ml of MeOH) was added dropwise over 15 min. The reaction was allowed to stir for an additional 15 min at 0° C. and acetone was added to form a precipitate, which was subsequently collected by filtration and washed with acetone. The crude material was redissolved in a minimal amount of MeOH and acetone was added until turbidity was apparent. The solution was centrifuged, the supernatant was collected, and more acetone was added to induce precipitation. The resulting solid was then collected by filtration, washed with acetone, and dried under vacuum to afford the product (391 mg, 0.529 mmol, 76% yield) as a white solid. $^1$H NMR (D$_2$O, 500 MHz): δ 7.23 (s, 3H), 3.86 (s, 6H), 2.57 (m, 6H), 2.35 (m, 6H), 1.71 (m, 6H), 1.62 (m, 6H). $^{13}$C NMR (D$_2$O, 126 MHz): δ 138.23, 129.46, 60.67, 42.34, 37.75, 28.23, 21.32; HRMS-MAIDI: m/z [M+H]+ calcd for [C$_{21}$H$_{34}$Na$_3$O$_6$S$_9$]$^+$: 738.9529; found: 738.9534.

B.

PEMP-DDA: To a stirring solution of pentaerythritol tetrakis(3-mercaptopropionate) (382 μL, 1.00 mmol) and DTDO (670 mg, 4.40 mmol) in EtOH/THF 3:1 (12 ml) at 0° C., a solution of NaOMe (freshly prepared from 92 mg of Na$^0$ and 3 ml of MeOH) was added dropwise over 15 min. The reaction was allowed to stir for an additional 15 min at 0° C., after which acetone was added to form a precipitate. The precipitate was collected by filtration, washed with acetone, and then redissolved in a minimal amount of MeOH. Acetone was added until turbidity was apparent, the solution was centrifuged, and the supernatant was collected and more acetone was added to induce precipitation. The resulting solid was then collected by filtration, washed with acetone, and dried under vacuum to afford the product (944 mg, 0.796 mmol, 80% yield) as a white solid. $^1$H NMR (D$_2$O, 500 MHz): δ 4.18 (s, 8H), 2.89 (m, 8H), 2.79 (m, 8H), 2.67 (m, 8H), 2.27 (m, 8H), 1.69 (m, 8H), 1.56 (m, 8H); $^{13}$C NMR (D$_2$O, 126 MHz): δ 172.96, 62.92, 60.58, 41.94, 37.81, 33.86, 32.64, 28.22, 21.22; HRMS-ESI: m/z [M-Na]$^-$ calcd for [C$_{33}$H$_{56}$Na$_3$O$_{16}$S$_{12}$]$^-$: 1160.9915; found: 1160.9946.

cis- and trans-DAcDTDO were prepared from dithioerythritol (DTE) and dithiothreitol (OTT) using similar procedures to those described by Field and Khim (2).

C. cis-DAcDTDO:

$^1$H NMR (DMSO-d$_6$, 500 MHz): δ 5.43-5.40 (m, 1H), 5.34 (dt, J=10.9, 3.1 Hz, 1H), 3.98 (dd, J=13.1, 3.4 Hz, 1H), 3.78 (dd, J=13.0, 11.0 Hz, 1H), 3.70 (dd, J=15.1, 5.6 Hz, 1H), 3.65-3.58 (m, 1H), 2.12 (s, 3H), 2.02 (s, 3H); $^{13}$C NMR (DMSO-d$_6$, 126 MHz): δ169.93, 169.35, 69.47, 64.34, 58.87, 34.77, 21.11, 21.00; HRMS-ESI: m/z [M+Na]$^+$ calcd for [C$_8$H$_{12}$NaO$_6$S$_2$]$^+$: 290.9968; found: 290.9972.

D. trans-DAcDTDO:

$^1$H NMR (CDCl$_3$, 500 MHz): δ 5.44 (td, J=8.3, 3.8 Hz, 1H), 5.13 (td, J=8.3, 3.1 Hz, 1H), 3.81 (dd, J=13.6, 3.S Hz, 1H), 3.66 (dd, J=13.6, 8.7 Hz, 1H), 3.61-3.53 (m, 1H), 3.45

(dd, J=14.6, 8.7 Hz, 1H), 2.13 (s, 3H), 2.11 (s, 3H); $^{13}$C NMR (CDCl$_3$, 126 MHz): δ 169.67, 169.15, 69.40, 6S.10, 60.74, 33.04, 20.89, 20.78; HRMS-DART: m/z [M+NH$_4$]$^+$ calcd for [C$_8$H$_{16}$NO$_6$S$_2$]$^+$: 286.0414; found: 286.0428.

cis- and trans-DHDTDO were prepared by a procedure adapted from literature (3): To DAcDTDO (1.00 g, 3.73 mmol) was added 7 M NH$_3$ in MeOH (100 mL) dropwise over 15 min under argon at rt. The solid went into solution as the NH$_3$ solution was added and the solution turned yellow. After 1.5 h, the reaction mixture was concentrated under vacuum, and the crude oil was purified by column chromatography (SiO$_2$, 5% MeOH in CH$_2$Cl$_2$) to give the DHDTDO as a white solid.

E. cis-DHDTDO:

0.560 g (3.04 mmol, 81% yield). $^1$H NMR (CD$_3$OD, 500 MHz): δ 4.23-4.18 (m, 1H), 4.13 (dt, J=11.0, 2.9 Hz, 1H), 3.66 (dd, J=12.7, 11.0 Hz, 1H), 3.47 (dd, J=14.7, 1.2 Hz, 1H), 3.42-3.33 (m, 2H); $^{13}$C NMR (CD$_3$OD, 126 MHz): δ 71.45, 65.93, 61.63, 38.65; HRMS-ESI: m/z [M+Na]$^+$ calcd for [C$_4$H$_8$NaO$_4$S$_2$]$^+$: 206.9756; found: 206.9755.

F. trans-DHDTDO:

0.520 g (2.83 mmol, 76% yield). $^1$H NMR (CD$_3$OD, 500 MHz): δ 3.97 (ddd, J=10.3, 8.6, 4.0 Hz, 1H), 3.79-3.68 (m, 2H), 3.51 (dd, J=13.2, 10.4 Hz, 1H), 3.37-3.29 (m, 1H), 3.22 (dd, J=14.2, 10.2 Hz, 1H); $^{13}$C NMR (CD$_3$OD, 126 MHz): δ 77.83, 77.36, 65.43, 36.21; HRMS-ESI: m/z [M+Na]$^+$ calcd for [C$_4$H$_8$NaO$_4$S$_2$]$^+$: 206.9756; found: 206.9760.

REFERENCES

1. Ferreira R B, Law M E, Jahn S C, Davis B J, Helderman C D, Reinhard M, et al. Novel agents that downregulate EGFR, HER2, and HER3 in parallel. Oncotarget. 2015 April. 30; 6(12):10445-59.
2. Field L, Khim Y H. Organic disulfides and related substances. 33. Sodium 4-(2-acetamidoethyldithio)butanesulfinate and related compounds as antiradiation drugs. J Med Chem. 1972 March; 15(3):312-5.
3. Mayasundari A, Rice W G, Diminnie J B, Baker D C. Synthesis, resolution, and determination of the absolute configuration of the enantiomers of cis-4,5-dihydroxy-1,2-dithiane 1,1-dioxide, an HIV-1NCp7 inhibitor. Bioorg Med Chem. 2003 Jul. 17; 11(14):3215-9.

What is claimed is:

1. A compound of Formula I, or salt thereof:

wherein,
each X is independently S or Se;
each Y is independently S or Se;
each Z is independently S or Se;
each Z$_1$, Z$_2$, and Z$_3$ is independently and
each R$_7$ is independently H, Na, K, optionally substituted alkyl, optionally substituted aryl, or optionally substituted arylalkyl.

2. A compound of Formula II, or salt thereof:

wherein,
each X is independently S or Se;
each Y is independently S or Se;
each Z is independently S or Se;
each Z$_1$, Z$_2$, Z$_3$, and Z$_4$ is independently each R$_7$ is independently H, Na, K, optionally substituted alkyl, optionally substituted aryl, or optionally substituted arylalkyl; and
each n is independently 0, 1, 2 or 3.

3. The compound of claim 1, or salt thereof:
wherein, X is S; Y is S; and Z is S.

4. The compound of claim 1, or salt thereof, wherein, X is S; Y is S; Z is S; and R$_7$ is K or Na.

5. The compound of claim 2, or salt thereof, wherein, n is 1; X is S; Y is S; Z is S; and R$_7$ is K or Na.

6. A compound that is:

sodium 4,4′,4″-((benzene-1,3,5-triyltris(methylene))tris(disulfanediyl))tris(butane-1-sulfinate)

-continued

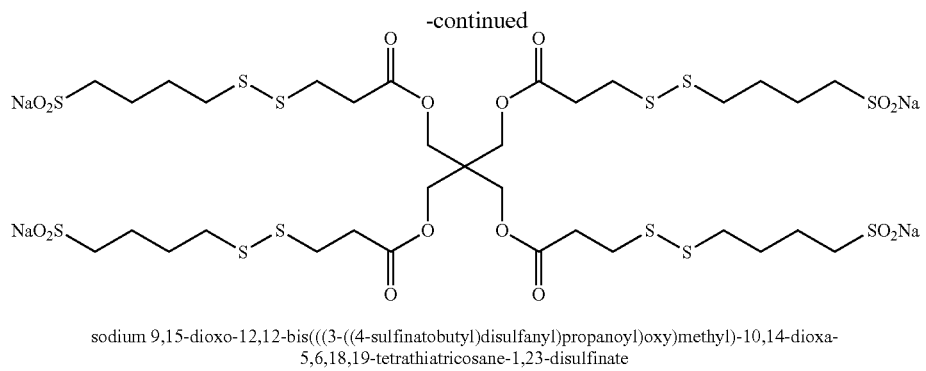

sodium 9,15-dioxo-12,12-bis(((3-((4-sulfinatobutyl)disulfanyl)propanoyl)oxy)methyl)-10,14-dioxa-5,6,18,19-tetrathiatricosane-1,23-disulfinate or salt thereof.

7. A method of treating a subject suffering from cancer comprising administering to the subject in need thereof a therapeutically effective amount of a compound of claim 1, or a salt thereof.

8. The method of claim 7, wherein the cancer is HER2 mediated or breast cancer.

9. The method of claim 8, wherein the breast cancer is HER2-positive breast cancer.

10. The method of claim 8, wherein the breast cancer is mediated by HER2, HER3, and/or EGFR.

11. A method of inhibiting cancer cell proliferation comprising administering to the subject in need thereof a therapeutically effective amount of a compound of claim 1, or a salt thereof.

12. The method of claim 11, wherein the cancer cell is HER2 mediated or a breast cancer cell.

13. The method of claim 12, wherein the breast cancer cell is a HER2-positive breast cancer cell.

14. A method of inhibiting cancer cell metastasis comprising administering to the subject in need thereof a therapeutically effective amount of a compound of claim 1, or a salt thereof.

15. A kit for treating a cell proliferative disorder, the kit comprising a compound of claim 1, or a salt thereof, and instructions for use.

16. A pharmaceutical composition comprising a compound of claim 1, or a salt thereof, and a pharmaceutically acceptable carrier.

17. The composition of claim 16, further comprising an additional therapeutic agent.

18. The composition of claim 17, wherein the additional therapeutic agent is lapatinib or trastuzumab.

19. A method of treating a subject suffering from cancer comprising administering to the subject in need thereof a therapeutically effective amount of a compound of claim 2, or a salt thereof.

20. A method of inhibiting cancer cell proliferation comprising administering to the subject in need thereof a therapeutically effective amount of a compound of claim 2, or a salt thereof.

* * * * *